United States Patent
Olson et al.

(10) Patent No.: US 7,736,649 B2
(45) Date of Patent: *Jun. 15, 2010

(54) METHODS OF INHIBITING HUMAN IMMUNODEFICIENCY VIRUS INFECTION THROUGH THE ADMINISTRATION OF SYNERGISTIC COMBINATIONS OF ANTI-CCR5 MONOCLONAL ANTIBODIES, FUSION INHIBITORS, AND CD4-GP120 BINDING INHIBITORS

(75) Inventors: William C. Olson, Ossining, NY (US); Paul J. Maddon, Scarsdale, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 5 days.

This patent is subject to a terminal disclaimer.

(21) Appl. No.: 11/520,556

(22) Filed: Sep. 12, 2006

(65) Prior Publication Data
US 2007/0020280 A1  Jan. 25, 2007

Related U.S. Application Data

(63) Continuation of application No. 09/912,824, filed on Jul. 25, 2001, now Pat. No. 7,138,119, which is a continuation-in-part of application No. PCT/US01/02633, filed on Jan. 26, 2001, and a continuation-in-part of application No. 09/663,219, filed on Sep. 15, 2000, now abandoned.

(60) Provisional application No. 60/266,738, filed on Feb. 6, 2001.

(51) Int. Cl.
A61K 39/395 (2006.01)
A61K 39/21 (2006.01)
C12P 21/08 (2006.01)

(52) U.S. Cl. ............ 424/154.1; 424/188.1; 530/388.75

(58) Field of Classification Search ................ None
See application file for complete search history.

(56) References Cited

U.S. PATENT DOCUMENTS

| | | |
|---|---|---|
| 4,886,743 A | 12/1989 | Hood |
| 5,021,409 A | 6/1991 | Murrer |
| 5,071,964 A | 12/1991 | Dustin |
| 5,091,513 A | 2/1992 | Huston |
| 5,126,433 A | 6/1992 | Maddon et al. |
| 5,215,913 A | 6/1993 | Posner |
| 5,225,539 A | 7/1993 | Winter et al. |
| 5,440,021 A | 8/1995 | Chuntharapai |
| 5,449,608 A | 9/1995 | Young |
| 5,504,003 A | 4/1996 | Li |
| 5,603,933 A | 2/1997 | Dwyer et al. |
| 5,668,149 A | 9/1997 | Oroszlan et al. |
| 5,817,767 A | 10/1998 | Allaway et al. |
| 5,854,400 A | 12/1998 | Chang |
| 5,939,320 A | 8/1999 | Littman et al. |
| 5,994,515 A | 11/1999 | Hoxie et al. |
| 6,025,154 A | 2/2000 | Li et al. |
| 6,100,087 A | 8/2000 | Rossi et al. |
| 6,107,019 A | 8/2000 | Allaway et al. |
| 6,258,527 B1 | 7/2001 | Littman et al. |
| 6,258,782 B1 | 7/2001 | Barney et al. |
| 6,261,763 B1 | 7/2001 | Allaway et al. |
| 6,265,184 B1 | 7/2001 | Gray et al. |
| 6,268,477 B1 | 7/2001 | Gray et al. |
| 6,344,545 B1 | 2/2002 | Allaway et al. |
| 6,448,375 B1 | 9/2002 | Samson et al. |
| 6,511,826 B2 | 1/2003 | Li et al. |
| 7,175,988 B2 | 2/2003 | Roschke et al. |

(Continued)

FOREIGN PATENT DOCUMENTS

EP  96870021.1  3/1996

(Continued)

OTHER PUBLICATIONS

Olson, W. C., 1999, Differential inhibition of human immunodeficiency virus type 1 fusion, gp120 binding, and CC-chemokine activity by monoclonal antibodies to CCR5, J. Virol. 73(5):4145-4155.*
Kilby, J. M., et al., 1998, Potent suppression of HIV-1 replication in humans by T-20, a peptide inhibitor of gp41-mediated virus entry, Nat. Med. 4(11):13021307.*
Gauduin, M.-C., et al., 1996, Effective ex vivo neutralization of human immunodeficiency virus type 1 in plasma by recombinant immunoglobulin molecules, J. Virol. 70(4):2586-2592.*
U.S. Appl. No. 09/663,219, filed Sep. 15, 2000, W.C. Olson et al.
U.S. Appl. No. 10/081,128, filed Feb. 22, 2002, W.C. Olson et al.
U.S. Appl. No. 09/212,793, filed Dec. 16, 1998, W.C. Olson et al.
U.S. Appl. No. 08/169,311, filed Dec. 17, 1993, G.P. Allaway et al.
U.S. Appl. No. 08/475,515, filed Jun. 7, 1995, G.P. Allaway et al.
U.S. Appl. No. 08/587,458, filed Jan. 17, 1996, V.W. Litwin et al.

(Continued)

*Primary Examiner*—Jeffrey S. Parkin
(74) *Attorney, Agent, or Firm*—John P. White; Cooper & Dunham LLP

(57) ABSTRACT

This invention provides a composition which comprises an admixture of three compounds, wherein: (a) one compound is an antibody which binds to a CCR5 receptor; (b) one compound retards attachment of HIV-1 to a CD4+ cell by retarding binding of HIV-1 gp120 envelope glycoprotein to CD4 on the surface of the CD4+ cell; and (c) one compound retards gp41 from adopting a conformation capable of mediating fusion of HIV-1 to a CD4+ cell by binding noncovalently to an epitope on a gp41 fusion intermediate; wherein the relative mass ratio of any two of the compounds in the admixture ranges from about 100:1 to about 1:100, the composition being effective to inhibit HIV-1 infection of the CD4+ cell. This invention also provides a method of inhibiting HIV-1 infection of a CD4+ cell which comprises contacting the CD4+ cell with an amount of the composition of the subject invention effective to inhibit HIV-1 infection of the CD4+ cell so as to thereby inhibit HIV-1 infection of the CD4+ cell.

23 Claims, 32 Drawing Sheets

U.S. PATENT DOCUMENTS

| | | | |
|---|---|---|---|
| 6,528,625 B1 | 3/2003 | Wu et al. |
| 6,548,636 B2 | 4/2003 | Dragic et al. |
| 6,692,745 B2 | 2/2004 | Olson et al. |
| 6,692,938 B2 | 2/2004 | Samson et al. |
| 6,743,594 B1 | 6/2004 | Li et al. |
| 6,759,519 B2 | 7/2004 | Li et al. |
| 6,797,811 B1 | 9/2004 | Gray et al. |
| 6,800,447 B2 | 10/2004 | Samson et al. |
| 6,800,729 B2 | 10/2004 | Li et al. |
| 6,908,734 B2 | 6/2005 | Dragic et al. |
| 6,930,174 B2 | 8/2005 | Samson et al. |
| 6,972,126 B2 | 12/2005 | Allaway et al. |
| 7,060,273 B2 | 6/2006 | Olson et al. |
| 7,118,859 B2 | 10/2006 | Litwin et al. |
| 7,122,185 B2 | 10/2006 | Olson et al. |
| 7,138,119 B2 | 11/2006 | Olson et al. |
| 7,151,087 B2 | 12/2006 | Combadiere et al. |
| 7,160,546 B2 | 1/2007 | Li |
| 7,345,153 B2 | 3/2008 | Litwin et al. |
| 7,501,123 B2 | 3/2009 | Roschke et al. |
| 2001/0000241 A1 | 4/2001 | Li et al. |
| 2002/0045161 A1 | 4/2002 | Allaway et al. |
| 2002/0048786 A1 | 4/2002 | Rosen et al. |
| 2002/0016834 A1 | 5/2002 | Rosen et al. |
| 2002/0061834 A1 | 5/2002 | Rosen et al. |
| 2002/0106374 A1 | 8/2002 | Olson et al. |
| 2002/0146415 A1 | 10/2002 | Olson et al. |
| 2002/0150888 A1 | 10/2002 | Gray et al. |
| 2002/0155429 A1 | 10/2002 | Allaway et al. |
| 2002/0177603 A1 | 11/2002 | Johnson et al. |
| 2003/0003440 A1 | 1/2003 | Lopalco et al. |
| 2003/0023044 A1 | 1/2003 | Li et al. |
| 2003/0044411 A1 | 3/2003 | Olson et al. |
| 2003/0092632 A1 | 5/2003 | Dragic et al. |
| 2003/0096221 A1 | 5/2003 | Littman et al. |
| 2003/0166024 A1 | 9/2003 | Rosen et al. |
| 2003/0166870 A1 | 9/2003 | Wu et al. |
| 2003/0195348 A1 | 10/2003 | Combadiere et al. |
| 2004/0062767 A1 | 4/2004 | Olson et al. |
| 2004/0086528 A1 | 5/2004 | Allaway et al. |
| 2004/0110127 A1 | 6/2004 | Samson et al. |
| 2004/0151719 A1 | 8/2004 | Li et al. |
| 2004/0161739 A1 | 8/2004 | Samson et al. |
| 2004/0228869 A1 | 11/2004 | Olson et al. |
| 2004/0230037 A1 | 11/2004 | Gray et al. |
| 2004/0259785 A1 | 12/2004 | Combadiere et al. |
| 2005/0118677 A1 | 6/2005 | Combadiere et al. |
| 2005/0131042 A1 | 6/2005 | Flentge |
| 2005/0154193 A1 | 7/2005 | Roschke et al. |
| 2005/0260565 A1 | 11/2005 | Gray et al. |
| 2006/0029932 A1 | 2/2006 | Allaway et al. |
| 2006/0140977 A1 | 6/2006 | Allaway et al. |
| 2006/0154857 A1 | 7/2006 | Redfield et al. |
| 2006/0194244 A1 | 8/2006 | Allaway et al. |
| 2006/0233798 A1 | 10/2006 | Olson et al. |
| 2007/0020280 A1 | 1/2007 | Olson |
| 2007/0025983 A1 | 2/2007 | Litwin et al. |
| 2007/0026441 A1 | 2/2007 | Olson et al. |
| 2007/0031408 A1 | 2/2007 | Olson |
| 2007/0048820 A1 | 3/2007 | Allaway |
| 2007/0231327 A1 | 10/2007 | Olson et al. |
| 2007/0274986 A1 | 11/2007 | Olson et al. |

FOREIGN PATENT DOCUMENTS

| | | | |
|---|---|---|---|
| EP | 96870102.9 | | 8/1996 |
| EP | 0815137 | | 12/1996 |
| EP | 1145721 | A2 | 10/2001 |
| EP | 1146055 | A2 | 10/2001 |
| EP | 1146122 | A2 | 10/2001 |
| EP | 1148126 | A2 | 10/2001 |
| EP | 1148127 | A2 | 10/2001 |
| EP | 1149582 | A2 | 10/2001 |
| EP | 1199360 | A2 | 4/2002 |
| EP | 0883687 | B1 | 10/2004 |
| EP | 1482042 | A1 | 12/2004 |
| WO | WO 92/01451 | | 2/1992 |
| WO | WO 94/19017 | | 9/1994 |
| WO | WO 94/22477 | | 10/1994 |
| WO | WO 97/45543 | | 12/1994 |
| WO | WO 95/16789 | | 6/1995 |
| WO | WO 96/39437 | | 12/1996 |
| WO | WO 96/41020 | | 12/1996 |
| WO | WO 97/22698 | | 6/1997 |
| WO | WO 97/26009 | | 7/1997 |
| WO | WO 97/28258 | | 8/1997 |
| WO | WO 97/32019 | | 9/1997 |
| WO | WO 97/37005 | | 10/1997 |
| WO | WO 97/44055 | | 11/1997 |
| WO | WO 97/44462 | | 11/1997 |
| WO | WO 97/47318 | A | 12/1997 |
| WO | WO 97/47319 | | 12/1997 |
| WO | WO 97/49424 | | 12/1997 |
| WO | WO 98/18826 | * | 5/1998 |
| WO | WO 98/56421 | | 12/1998 |
| WO | WO 00/35409 | | 6/2000 |
| WO | WO 01/55439 | | 8/2001 |
| WO | WO 01/58915 | | 8/2001 |
| WO | WO 01/58916 | | 8/2001 |
| WO | WO 01/64710 | | 9/2001 |
| WO | WO 02/22077 | | 3/2002 |
| WO | WO 02/064612 | | 8/2002 |
| WO | WO 02/068608 | | 9/2002 |
| WO | WO 02/083172 | | 10/2002 |
| WO | WO 03/072766 | | 9/2003 |
| WO | WO 2007/014114 | | 2/2007 |

OTHER PUBLICATIONS

U.S. Appl. No. 08/627,684, filed Apr. 2, 1996, G.P. Allaway et al.
U.S. Appl. No. 08/663,616, filed Jun. 14, 1996, G.P. Allaway et al.
U.S. Appl. No. 08/663,171, filed Jun. 14, 1996, G.P. Allaway et al.
U.S. Appl. No. 08/665,090, filed Jun. 14, 1996, G.P. Allaway et al.
U.S. Appl. No. 08/673,682, filed Jun. 25, 1996, G.P. Allaway et al.
U.S. Appl. No. 08/874,570, filed Jun. 13, 1997, G.P. Allaway et al.
U.S. Appl. No. 08/874,618, filed Jun. 13, 1997, G.P. Allaway et al.
U.S. Appl. No. 09/118,415, filed Jul. 17, 1998, V.W. Litwin et al.
U.S. Appl. No. 09/724,105, filed Nov. 28, 2000, G.P. Allaway et al.
U.S. Appl. No. 60/358,886, filed Feb. 22, 2002, W.C. Olson et al.
U.S. Appl. No. 60/014,532, filed Apr. 2, 1996, G.P. Allaway et al.
U.S. Appl. No. 60/017,157, filed May 20, 1996, D. Littman et al.
U.S. Appl. No. 60/266,738, filed Feb. 6, 2001, W.C. Olson et al.
U.S. Appl. No. 60/282,380, filed Apr. 6, 2001, W.C. Olson et al.
U.S. Appl. No. 60/019,715, filed Jun. 14, 1996, W.C. Olson et al.
U.S. Appl. No. 60/019,941, filed Jun. 14, 1996, G.P. Allaway et al.
U.S. Appl. No. 60/112,532, filed Dec. 16, 1998, W.C. Olson et al.
U.S. Appl. No. 60/185,667, filed Feb. 29, 2000, T. Dragic et al.
U.S. Appl. No. 60/205,839, filed May 19, 2000, T. Dragic et al.
U.S. Appl. No. 60/267,231, filed Feb. 7, 2001, T. Dragic et al.
U.S. Appl. No. 60/272,203, filed Feb. 28, 2001, T. Dragic et at.
U.S. Appl. No. 60/018,508, filed May 28, 1996, C. Combadiere et al.
PCT International Preliminary Examination Report issued Feb. 15, 2001 for International Application Publication No. WO 00/35409.
PCT International Preliminary Examination Report issued Dec. 24, 2003 for International Application Publication No. WO 02/083172.
PCT Written Opinion issued May 25, 2005 in connection with International Application Publication No. WO 03/072766.
PCT International Preliminary Examination Report issued Oct. 18, 1996 for International Application Publication No. WO 95/16789.
PCT International Preliminary Examination Report issued Sep. 5, 1997 for International Application Publication No. WO 96/41020.
PCT International Preliminary Examination Report issued Jan. 27, 2000 for International Application Publication No. WO 98/56421.

PCT International Preliminary Examination Report issued Jul. 10, 1998 for International Application Publication No. WO 97/37005.
PCT International Search Report issued Oct. 10, 1996 for International Application Publication No. WO 96/41020.
PCT International Search Report issued Mar. 13, 1995 for International Application Publication No. WO 95/16789.
PCT International Search Report issued Jun. 9, 1997 for International Application Publication No. WO 97/26009.
PCT International Preliminary Examination Report issued Feb. 15, 2001 for International Application Publication No. WO 00/35409.
PCT International Preliminary Examination Report issued Dec. 24, 2003 for International Application Publication No. WO 02/083172.
PCT Written Opinion issued May 25, 2005 in connection with International Application Publication No. WO 03/072766.
European Patent Application No. 96870021.1 filed Mar. 1, 1996.
European Patent Application No. 96870102.9 filed Aug. 6, 1996.
European Patent Application Publication No. 1145721 A2 published Oct. 17, 2001.
European Patent Application Publication No. 1146055 A2 published Oct. 17, 2001.
European Patent Application Publication No. 1146122 A2 published Oct. 17, 2001.
European Patent Application Publication No. 1148126 A2 published Oct. 24, 2001.
European Patent Application Publication No. 1148127 A2 published Oct. 24, 2001.
Jun. 9, 2005 Notice of Allowance and Allowability in connection with U.S. Appl. No. 10/116,797.
Apr. 25, 2005 Final Office Action in connection with U.S. Appl. No. 10/116,797.
Oct. 6, 2004 Office Action in connection with U.S. Appl. No. 10/116,797.
Sep. 7, 2005 Office Action in connection with U.S. Appl. No. 09/88,938.
Max, E. (1999). "Immunoglobulins: Molecular Genetics", in Fundamental Imunology, 4th edition, W.E. Paul, ed., Lippincott-Raven Publishers, Philadelphia. pp. 142-143.
European Supplementary Search Report issued Sep. 5, 2002 for European Patent Application No. 95905987.4.
European Supplementary Search Report issued Feb. 24, 2000 for European Patent Application No. 96921473.3.
European Supplementary Search Report issued Mar. 6, 2002 for European Patent Application No. 97917856.3.
European Supplementary Partial Search Report issued Feb. 19, 2003 for European Patent Application No. 98931261.6.
European Supplementary Partial Search Report issued Aug. 26, 2004 for European Patent Application No. 97930120.7.
European Supplementary Partial Search Report issued Nov. 8, 2004 for European Patent Application No. 97930120.7.
European Supplementary Partial Search Report issued Sep. 27, 2004 for European Application No. 99966466.
European Supplementary Search Report issued Apr. 21, 2006 for European Application No. 03713632.2.
European Patent Office Communication issued Nov. 11, 2004 in connection with European Patent Application No. 97930120.7.
Canadian Patent Application Publication No. 2216990 published Dec. 27, 1997.
Genbank Sequence Report, Accession Entry X91492 for *H. sapiens* Chem13, submitted Sep. 14, 1995.
Janeway and Travers (1994). Immunobiology, Current Biology Ltd., San Francisco. pp. 10:27-10:42.
Stryer (1988). Biochemistry, 3rd edition. pp. 984-988.
Dec. 17, 2003 Third Party Observations in connection with European Application No. 97904948.3.
Feb. 27, 2004 Third Party Observations in connection with European Application No. 97904948.3.
Abaza, M.S.I. and Astassi, M.Z. (1992). Effects Of Amino Acid Substitutions Outside An Antigenic Site On Protein Binding To . . . J. Prot. Chem., 11(5):433-443.
Alexander, H., et al. (1992). Altering The Antigenicity Of Proteins. Proc. Natl. Acad. Sci., 89:3352-3356.
Alkhatib, et al. (1996). Abstract At 3rd Conference On Retroviruses.

Alkhatib, G., et al. (1996). CC CKR5: A RANTES, MIP-1a, MIP-1β Receptor As A Fusion Cofactor For Macrophage-Tropic HIV-1. Science, 272:1955-1958.
Alkhatib, G., et al. (1997). HIV Co-Receptor Activity Of CCR5 And Its Inhibition By Chemokines: Independence From G Protein Signaling . . . Virology, 234:340-348.
Allan, J. (1997) "Human Immunodeficiency . . . ," in AIDS: Biology, Diagnosis, . . . , 4th edition, De Vita, Jr., et al., eds., Lippincott-Raven Publishers, Philadelphia. pp. 15-27.
Arenzana-Selsdedos, F., et al. (1996). HIV Blocked By Chemokine Antagonist. Nature, 383:400.
Ashorn, P.A., et al. (1990). Human Immunodeficiency Virus Envelope Glycoprotein/CD4 Mediated Fusion Of Nonprimate Cells With Human Cells. J. Virol., 64:2149-2156.
Attanasio, et al. (1991). Anti-Idiotypic Antibody Response To Monoclonal Anti-CD4 Preparations In Nonhuman Primate Species. J. Immunol., 146:507-514.
Baba, et al. (1998). Mechanism of Inhibitory Effect Of Dectran Sulfate And Heparin On Replication Of Human Immunodeficiency Virus In . . . Proc. Natl. Acad. Sci., 85:6132-6135.
Back, D.J. (1999). Pharmacological Issues Relating To Viral Resistance. Infection, 27(Suppl.2):S42-S44.
Balzarini, et al. (1995). Suppression Of The Breakthrough Of HIV-1 In Cell Culture By Thiocarboxanilide Derivatives When Used . . . Proc. Natl. Acad. Sci., 92:5470-5474.
Baulerle and Huttner (1987). Tyrosine Sulfation Is A Trans-Golgi-Specific Protein Modification. Cell. Biol., 105:2655-2663.
Benet, et al. (1990). "Pharmacokinetics: . . . ", in Goodman And Gilman's . . . The Pharmacological Basis of Therapeutics, Gilman, et al., eds., Pergamon Press, New York. pp. 3-32.
Berger, et al. (1996). Abstract No. 002, 8 at Keystone Symposium.
Berger, et al. (1999). Chemokine Receptors As HIV-1 Coreceptors: Roles In Viral Entry, Tropism And Disease. Ann. Rev. Immunol., 17:657-700.
Blanpain, C., et al. (1999). Multiple Charged And Aromatic Residues In CCR5 Amino-Terminal Domain Are Involved In High Affinity Binding . . . J. Biol. Chem., 274:34719-34727.
Bleul, C.C., et al. (1991). The Lymphocyte Chemoattractant SDF-1 Is A Ligand For LESTR/Fusion And Blocks HIV-1 Entry. Nature, 382:829-832.
Brenner, T.J., et al. (1996). Relation Between HIV-1 Syncytium Inhibition Antibodies And Clinical Outcome In Children. Lancet, 337:1001-1005.
Broder, et al. (1993). The Block To HIV-1 Envelope Glycoprotein-Mediated Membrane Fusion In Animal Cells Expressing Human CD4 Can Be Overcome . . . Virol., 193:483-491.
Broder, et al. (1996). HIV And The 7-Transmembrane Domain Receptors. Pathobiology, 64(4):171-179.
Busso, et al. (1991). HIV-Induced Syncytium Formation Requires The Formation Of Conjugates Between Virus-Infected And Uninfected T-Calls in Vitro. AIDS, 5:1425-1432.
Camerini, D., et al. (1990). A CD4 Domain Important For HIV-Mediated Syncytium Formation Lies Outside The Virus Binding Site. Cell, 60(5):747-754.
Cammack, N. (1999). Human Immunodeficiency Virus Type 1 Entry And Chemokine Receptors: A New Therapeutic Target. Antiviral Chemistry And Chemotherapy, 10:53-62.
Chams, et al. (1992). Simple Assay To Screen For Inhibitors Of Interaction Between The Human Immunodeficiency Virus Envelope . . . Antimicrob Agents Chemother., 36(2):262-272.
Charo, et al. (1994). Molecular Cloning And Functional Expression Of Two Monocyte Chemoattractant Protein 1 Receptors Reveals . . . Proc. Natl. Acad. Sci., 91:2752-2756.
Clapham, P.R., et al. (1991). Specific Cell Surface Requirements For The Infection Of CD4-Positive Cells By Human Immunodeficiency . . . Virol., 181:703-715.
Cocchi, F. (1995). Identification Of RANTES, MIP-1alpha and MIP-1beta As The Major HIV-Suppressive Factors Produced By CD8+ T-Cells. Science, 270:1811-1815.
Combadiere, et al. (1995). Cloning and Functional Expression Of A . . . J. Biol. Chem., 270, 16491-16494 (Note—Erratum in: J Biol Chem Dec. 15, 1995;270(50):30235)).

Combadiere, et al. (1996). Cloning And Functional Expression Of CC CKR5, A Human Monocyte CC Chemokine Receptor Selective For MIP-1a, MIP-1β. . . J. Leukos. Biol., 60:147-152.

Cormier, E.G., et al. (2000). Specific Interaction Of CCR5 Amino-Terminal Domain Peptides Containing Sulfotyrosines With HIV-1 . . . Proc. Natl. Acad. Sci., 97:5762-5767.

Crowe, S.M., et al. (1992). Human Immunodeficiency Virus-Infected Monocyte-Derived Macrophages Express Surface Gp120 And Fuse . . . Clin. Immunol Immunopathol., 65(2):143-151.

Cruse, et al. (1995). Illustrated Dictionary Of Immunology, CRC Press, Inc, Boca Raton, FL., 143:QR180.4.C78.

Daar, E.S. (1990). High Concentrations Of Recombinant Soluble CD4 Are Required To Neutralize Primary Human Immunodeficiency Virus Type . . . Proc. Natl. Acad. Sci., 87:6574-6578.

Dalgleish, A.G. (1995). HIV and CD26. Nature Medicine, 1:881-882.

Dean, M., et al. (1996). Genetic Restriction Of HIV-1 Infection And Progression To AIDS By A Deletion Allele Of The CKR5 Structural Gene. Science, 273:1856-1862.

De Clerq, et al. (1992). Potent and Selective Inhibition Of Human Immunodeficiency Virus (HIV)-1 and HIV-2 Replication By A Class Of . . . Proc. Natl. Acad. Sci., 89:5286-5290.

De Clerq, et al. (1994). Highly Potent And Selective Inhibition Of Human Immunodeficiency Virus By The Bicyclam . . . Antimicrobial Agents and Chemotherapy, 38:668-674.

De Clerq, et al. (1995). Antiviral Therapy For Human Immunodeficiency Virus Infections. J. Clin. Microbiol. Rev., 8(2):200-239.

Deng, X., et al. (1999). A Synthetic Peptide Derived From Human Immunodeficiency Virus Type 1 Gp120 Down-Regulates The Expression . . . Blood, 94(4):1165-1173.

Dettin, et al. (2003). CCR5 N-Terminus Peptides Enhance X4 HIV-1 Infection By CXCR4 Up-Regulation. Biochem. Biophys. Res. Commun., 307(3):640-646.

Dikic (1996). Regulation of HIV-1 Infection by Chemokine Receptors. Acta. Med. Croatica, 50:163-168.

Dimitrov, et al. (1991). Initial Stages of HIV-1 Envelope Glycoprotein-Mediated Cell Fusion Monitored By A New Assay Based On . . . AIDS Res. Hum. Retroviruses, 7(10):799-805.

Ditzel, et al. (1998). The CCR5 Receptor Acts As An Alloantigen In . . . Homozygous Individuals: Identification Of Chemokine And HIV-1 . . . Proc. Natl. Acad. Sci., 95(9):5241-5245.

Dragic, et al. (1992). Complementation Of Murine Cells For Human Immunodeficiency Virus Envelope/CD4-Mediated Fusion in Human-Murine . . . J. Virol., 66(8):4794-4802.

Dragic, T.V., et al. (1993). Different Requirements For Membrane Fusion Mediated By The Envelopes Of Human Immunodeficiency Virus Types 1 And 2. J. Virol., 67(4):2355-2359.

Dragic, T.V., et al. (1995). Proteinase-Resistant Factors In Human Erythrocyte Membranes Mediated Cd-4 Dependent Fusion With Cells . . . J. Virol., 69:1013-1018.

Dragic, T.V., et al. (1998). Amino-Terminal Substitutions In The CCR5 Coreceptor Impair Gp120 Binding And Human Immunodeficiency Virus Type 1 Entry. J. Virol., 72(1):279-285.

Dragic, et al. (2000). A Binding Pocket For A Small Molecule Inhibitor Of HIV-1 Entry Within The Transmembrane Helices Of CCR5. Proc. Natl. Acad. Sci., 97(10):5639-5644.

Ebadi, M. (1998). The Pharmacokinetic Basis Of Therapeutics. CRC Desk Reference Of Clinical Pharmacology, pp. 1-7.

Eugen-Olsen, J., et al. (1997). Heterozygosity For A Deletion In The CKR-5 Gene Leads To Prolonged AIDS-Free Survival And Slower CD4 . . . AIDS, 11:305-310.

Fahey, J.L., et al. (1992). Status Of Immune-Based Therapies In HIV Infection And AIDS. Clin. Exp. Immunol., 88:1-5.

Farzan, M., et al. (1998). A Tyrosine-Rich Region In The N-Terminus Of CCR5 Is Important For Human Immunodeficiency Virus Type 1 Entry . . . J. Virol., 72:1160-1164.

Farzan, M., et al. (1999). Tyrosine Sulfation Of The Amino-Terminus Of CCR5 Facilitates HIV-1 Entry. Cell, 96:667-676.

Farzan, M., et al. (2000). A tyrosine-sulfated peptide based on the N terminus of CCR5 interacts with a CD4-enhanced epitope of the HIV-1 . . . J. Biol. Chem., 275:33416-33521.

Feng, et al. (1996). Abstract No. 116,21 at Keystone Symposium.

Flexner, C. and Hendrix, C. (1997). "Pharmacology . . . ", in AIDS: Biology, Diagnosis, . . . , 4th Edition, De Vita V., et al. eds., Lippincott-Raven Publishers. pp. 479-493.

Fouchier, et al. (1994). HIV-1 Macrophage Tropism Is Determined At Multiple Levels Of The Viral Replication Cycle. J. Clin. Invest., 94:1806-1814.

Fox, J.L. (1994). No Winners Against Aids. Bio/Technology, 12:128.

Freed, E.O., et al. (1991). Identification Of Conserved Residues In The Human Immunodeficiency Virus Type 1 Principal . . . AIDS Res. Hum. Retroviruses, 7(10):807-811.

Frazer, J.K. and Capra, J.D. (1999). "Immunoglobulins: . . . ", in Fundamental Immunology, 4th Edition, W.E. Paul, ed., Lippincott-Raven Publishers, Philadelphia. pp. 111-182.

Ghorpade A., et al. (1998). Role Of The Beta-Chemokine Receptors CCR3 And CCR5 In Human Immunodeficiency Virus Type 1 Infection Of Monocytes And . . . J. Virol, 72:3351-3361.

Golding, H., et al. (1992). LFA-1 Adhesion Molecules Are Not Involved In The Arly Stages Of HIV-1 Env-Mediated Cell Membrane Fusion. AIDS Res. Hum. Retroviruses, 8:1593-1598.

Gong, J.H., et al. (1995). Antagonists Of Monocyte Chemoattractant Protein 1 Identified By Modification Of Functionally Critical NH2-Terminal . . . J. Exp. Med., 181:631-640.

Gong, J.H., et al. (1996). RANTES And MCP-3 Antagonists Bind Multiple Chemokine Receptors. J. Biol. Chem., 371:10521-10527.

Graham, et al. (1995). Candidate Aids Vaccines. New Engl. J. Med., 333:1331-1339.

Grene, et al. (2001). Anti-CCR5 Antibodies In Sera Of HIV-Positive Individuals. Human Immunol., 62(2):143-145.

Harouse, J.M., et al. (1991). Inhibition Of Entry Of HIV-1 in Neural Cell Lines By Antibodies Against Galactosyl Ceramide. Science, 253(5017):320-323.

Harrington, R.D. and Geballe, A.P. (1993). Cofactor Requirement For Human Immunodeficiency Virus Type 1 Entry Into A CD4-Expressing Human Cell Line. J. Virol., 67:5939-5947.

Hattori, T., et al. (1989). Involvement Of Tryptase-Related Cellular Protease(S) In Human Immunodeficiency Virus Type 1 Infection. FEBS Letters, 248:48-52.

Haynes, B.F. (1996). Updates On The Issues Of HIV Vaccine Development. Ann. Med., 28:39-41.

He, Jianglin, et al. (1997). CCR3 And CCR5 Are Co-Receptors For HIV-1 Infection Of Microglia. Nature, 385:645-649.

Heath, et al. (1997). Chemokine Receptor Usage By Human Eosinophils. The Importance Of CCR3 Demonstrated Using An . . . J. Clin. Invest., 99:178-184.

Heidenreich, et al. (1995). Application Of Antisense Technology To Therapeutics. Mol. Med. Today, 1:128-133.

Hildreth, et al. (1989). Involvement Of A Leukocyte Adhesion Receptor (LFA-1) In HIV-Induced Syncytium Formation. Science, 244:1075-1078.

Hirata, Y. (1989). Characterization Of IL-6 Receptor Expression By Monoclonal And Polyclonal Antibodies. J. Immun., 2900-2906.

Hirsch, et al. (1997). "Antiretroviral . . . ", in AIDS: Biology, Diagnosis, . . . , 4th Edition, De Vita, Jr., et al. eds., Lippincott-Raven Publishers, Philadelphia. pp. 495-508.

Howard, O.M.Z., et al. (1998). Small Molecule Inhibitor Of HIV-1 Cell Fusion Blocks Chemokine Receptor-Mediated Fusion. J. Leuk. Biol., 64:6-13.

Hwang, S.S., et al. (1991). Identification Of The Envelope V3 Loop As The Primary Determinant Of Cell Tropism In HIV-1. Science, 253:71-74.

Jacobson, J.M., et al. (1993). Passive Immunotherapy In The Treatment Of Advanced Human Immunodeficiency Virus Infection. J. Infect. Dis., 168:298-305.

Jones, S.A., et al. (1997). Chemokine Antagonists That Discriminate Between Interleukin-8 Receptors. J. Biol. Chem., 272:16166-16199.

Karwowska, S., et al. (1991). Passive Immunization For The Treatment And Prevention Of HIV Infection. Biotech. Therap., 2:31-48.

Katinger, H. (1994). Human Monoclonal Antibodies For Passive Immunotherapy Of HIV-1. Antibiot. Chemother., 46:23-37.

Keller, P.M., et al. (1977). A Fluorescence Enhancement Assay Of Cell Fusion. J. Cell Sci., 28:167-177.

Klotman, et al. (1995). Transgenic Models Of HIV-1. AIDS, 9(4):313-324.

Konigs, C., et al. (2000). Monoclonal Antibody Screening Of Phage-Displayed Random Peptide Library Reveals Mimotopes Of Chemokine . . . Eur. J. Immnol., 30(4):1162-1171.

Konishi, K., et al. (2000). Synthesis Of Peptides Mimicking Chemokine Receptor CCR5 And Their Inhibitory Effects Against HIV-1 . . . Chem. Pharm. Bull., Tokyo, 48(2):308-309.

Koup, R.A., et al. (1996). Defining Antibody Protection Against HIV-1 Transmission In Hu-PBL-SCID Mice. Immunology, 8:263-268.

Levy, J.A. (1996). Controlling HIV Pathogenesis: The Role Of The Non-Cytotoxic Anti-HIV Response of CD8+ Cells. Immunology Today, 17:217-224.

Loetscher, M., et al. (1994). Cloning Of A Human Seven-Transmembrane Domain Receptor, LESTR, That Is Highly Expressed In Leukocytes. J. Biol. Chem., 269:232-237.

Maddon, P.J., et al. (1986). The T4 Gene Encodes The AIDS Virus Receptor And Is Expressed In The Immune System And The Brain. Cell, 47:333-348.

Mateu, M.G., et al. (1992). Non-Additive Effects Of Multiple Amino Acid Substitutions On Antigen-Antibody Recognition. European J. Immunol., 22(6):1385-1389.

Mellors, J.W. (1996). Closing In On Human Immunodeficiency Virus-1. Nature Medicine, 2(3):274-275.

Mitsuya, H., et al. (1985). "Protection", in Retroviruses in Human Lymphoma Leukemia, Miwa, et al. eds., Japan Sci. Soc. Press, Tokyo/VNU Science Press, Utrecht. pp. 277-288.

Mittler, R.S., et al. (1989). Synergism Between Hiv gp120 And gp120-Specific Antibody In Blocking Human T. Cell Activation. Science, 245:1380-1382.

Moser, B., et al. (1993). Interleukin-8 Antagonists Generated By N-Terminal Modification. J. Biol. Chem., 268:7125-7128.

Mosier, D.E. (1990). Immunodeficient Mice Xenografted With Human Lymphoid Cells: New Models For In-Vivo Studies Of Human . . . J. Clin. Immuno., 10(4):185-191.

Nagasawa, et al. (1994). Molecular Cloning And Structure Of A Pre-B-Cell Growth-Stimulating Factor. Proc. Natl. Acad. Sci., 91:2305-2309.

Nakano, T., et al. (1995). Vascular smooth muscle cell-derived, Gla-containing growth-potentiating factor for Ca2+ mobilizing growth . . . J. Biol. Chem., 270(11):5702-5705.

Neote, et al. (1993). Molecular cloning, functional expression, and signaling characteristics of a C-C chemokine receptor. Cell, 72:415-425.

O'Brien, et al. (1990). HIV-1 Tropism for Mononuclear Phagocytes can be Determined by Regions of gp120 Outside of the CD4-binding domain. Nature, 348:69-73.

Oberg, B and Vrang, L. (1990). Screening for new agents. Eur. J. Clin. Microbiol. Infect. Dis., 9(7):466-471.

Oberlin, E., et al. (1996). The CXC Chemokine SDF-1 is the Ligand for LESTR/fusion and prevents infection by T-cell-line-adapted HIV-1. Nature, 382: 833-835.

Oellerich, M., (1984). Enzyme-Immunoassay: A Review. J. Clin. Chem. Clin. Biochem., 22(12):895-904.

Opperman, (2004). Chemokine Receptor CCR5: Insights Into Structure, Function, And Regulation. Cell. Signal., 16:1201-1210.

Partidos, C., et al. (1992). The Effect Of Orientation Of Epitopes On The Immunogenicty Of Chimeric Synthetic Peptides Representing . . . Molecular Immunology, 29(5):651-658.

Peden, et al. (1991). Changes in Growth Properties On Passage In Tissue Culture Of Viruses Derived From Infectious Molecular Clones . . . Virol., 185:661-672.

Poignard, P., et al. (1999). Neutralizing Antibodies Have Limited Effects On The Control Of Established HIV-1 Infection In-Vivo. Immunity, 10:431-438.

Power, et al. (1995). Molecular Cloning And Functional Expression Of A Novel CC Chemokine Receptor cDNA From A Human Basophilic Cell Line. J. Biol. Chem., 270:1811-1815.

Proudfoot, et al. (1996). Extension Of Recombinant Human RANTES By The Retention Of The Initiating Methionine Produces A Potent Antagonist. J. Biol. Chem., 271:2599-2603.

Proudfoot, et al. (1999). Chemokine Receptors: Future Therapeutic Targets For HIV. Biochem. Pharmacol., 57:451-463.

Proudfoot, et al. (2000). The Strategy Of Blocking The Chemokine System To Combat Disease. Immunol. Rev., 177:246-256.

Queen, et al. (1989). A Humanized Antibody That Binds To The Interleukin 2 Receptor. Proc. Natl. Acad. Sci, 86:10029-10033.

Rabut, G.E., et al. (1991). Alanine Substitutions Of Polar And Nonpolar Residues In the Amino-Terminal Domain Of CCR5 Differently . . . J. Virol., 72:3464-3468.

Raport, C.J., et al. (1996). Molecular Cloning And Functional Characterization Of A Novel Human CC-Chemokine Receptor (CCR5) For . . . J. Biol. Chem., 271:17161-17166.

Raport, C.J., et al. (1996). New Members Of The Chemokine Receptor Gene Family. Journal of Leukocyte Biology, 59:18-23.

Raport, C.J., et al. (1996). AAC50598 submitted to NCBI on Apr. 12, 1996 (CC Chemokine Receptor 5 sequence).

Richman, D.D. (1996). Antiretroviral Drug-Resistance: Mechanisms, Pathogenesis, Clinical Significance. Antivir. Chemother., 4:383-395.

Rodriguez, G., et al. (1995). Mediation Of Human Immunodeficiency Virus Type 1 Binding By Interaction Of Cel Surface Heparin Sulfate . . . J. Virol., 69:2233-2239.

Rucker, et al. (1996). Regions in Beta-Chemokine Receptors CCR5 And CCR2b That Determine HIV-1 Cofactor Specificity. Cell, 87:437-446.

Ruffing, et al. (1998). CCR5 Has An Expanded Ligand-Binding Repertoire And Is The Primary Receptor Used By MCP-2 On Activated T-Calls. Cell. Immunol., 160:160-168.

Rusche, et al. (1988). Antibodies That Inhibit Fusion Of Human Immunodeficiency Virus-Infected Cells Bind A 24-Amino Acid Sequence . . . Proc. Natl. Acad. Sci., 85:3198-3202.

Sagg, M. (1997). "Clinical Spectrum . . . ", in AIDS: Biology, Diagnosis, Treatment and Prevention, De Vita et al., eds., Lippincott-Raven Publishers, Philadelphia. pp. 202-213.

Samson, M., et al. (1996). Molecular Cloning And Functional Expression Of A New Human CC-Chemokine Receptor Gene. Biochem., 35:3362-3367.

Sandberg, J. (1995). Developmental Pharmacology And Toxicology Of Anti-HIV Therapeutic Agents: Dideoxynucleosides. FASEB J., 9:1157-1163.

Sandstorm, E.G. and Kaplan, J.C. (1987). Antiviral Therapy in AIDS: Clinical Pharmacological Properties And Therapeutic Experience To Date. Drugs, 34:372-390.

Sato, et al. (1992). Anti-Cd7 Reagents Inhibit HIV-1 Induced Syncytium Formation. International Conference on AIDS, 81. PA5 PoA 2017.

Sato, et al. (1994). Identification Of CD7 Glycoprotein As An Accessory Molecule in HIV-1 Mediated Syncytium Formation And Cell Free Infection. J. Immunol., 152:5142-5152.

Sato, et al. (1995). A Simple And Rapid Method For Preliminary Evaluation Of In Vivo Efficacy Of Anti-HIV Compounds In Mice. Antivir. Res., 27:151-163.

Scarlatti, et al. (1997). In Vivo Evolution Of HIV-1 Co-Receptor Usage And Sensitivity To Chemokine-Mediated Suppression. Nature Medicine, 3(11):A2581259-1265.

Schanberg, et al. (1995). Characterization Of Human CD7 Transgenic Mice. J. of Immunol., 155:2407-2418.

Schmidtmayerova, H., et al. (1993). Characterization Of HIV1-PAR, a Macrophage-Tropic Strain: Cell Tropism, Virus/Cell Entry And . . . Research in Virology, 144(1):21-26.

Schols, D., et al. (1999). CD26-Processed RANTES(3-68), But Not Intact RANTES, Has Potent Anti-HIV-1 Activity. Antiviral Res., 30:175-187.

Simmons, G., et al. (1997). Potent Inhibition Of HIV-1 Infectivity In Macropages And Lymphocytes By A Novel CCR5 Antagonist. Science, 276:276-279.

Sinangil, et al. (1988). Quantitative Measurement Of Fusion Between Human Immunodeficiency Virus And Cultured Cells Using Membrane Fluorescence Dequenching. FEB 239(1):88-92.

Sommerfelt, M.A., et al. (1995). Intercellular Adhesion Molecule 3, A Candidate Human Immunodeficiency Virus Type 1 Co-Receptor On . . . J. Gen. Virol., 76:1345-1352.

Stein, et al. (1993). Immune-Based Therapeutics: Scientific Rationale And Promising Approaches To The Treatment Of The Human . . . Clin. Infect. Dis., 17:749-771.

Steinberger, P., et al. (2000). Generation And Characterization Of A Recombinant Human CCR5-Specific Antibody. J. Biol. Chem., 275:36073-36078.

Stewart, G.J. (1997). Increased Frequency Of CCR-5Δ32 Heterozygotes Among Long-Term Non-Progressors With HIV-1 Infection. AIDS, 11:1833-1838.

Su, et al. (1996). Preparation Of Specific Polyclonal Antibodies To A C-C Chemokine Receptor, CCR1, And Determination Of CCR1 Expression On . . . J. Leukos. Biol., 60:658-666.

Szabo, et al. (1992). Cd4 Changes Conformation Upon Ligand Binding. J. Immunol. 149(11):3596-3604.

Szabo, G. Jr., et al. (1993). Specific Disengagement Of Cell-Bound Anti-LAM-1 (Anti-Selectin) Antibodies By Aurintricarboxylic Acid. Molecular Immunology, 30(18):1689-1694.

Travis, B.M., et al. (1992). Functional Roles Of The V3 Hypervariable Region Of HIV-1 gp160 In The Processing Of gp160 And . . . Virol. 186:313-317.

Tulip, W.R., et al. (1992). Crystal Structures Of Two Mutant Neraminidase-Antibody Complexes With Amino Acid Substitutions In The Interface. J. Mol. Biol., 227:149-159.

Valentin, et al. (1990). The Leukocyte Adhesion Glycoprotein CD18 Participates In HIV Induced Syncyia Formation In Monocytoid And T Cells. J. of Immunology, 144:934-937.

Vanini, S., et al. (1992). Discrete Regions Of HIV-1 Gp41 Defined By Syncytia-Inhibiting Affinity-Purified Human Antibodies. AIDS, 7:176-174.

Verrier, F.C., et al. (1997). Antibodies To Several Conformation-Dependent Epitopes Of gp120/gp41 Inhibit CCR-5-Dependent Cell-To-Cell . . . Proc. Natl. Acad. Sci., 94:9326-9331.

Vila-Coro, et al. (2000). HIV-1 Infection Through The CCR5 Receptor Is Blocked By Receptor Dimerization. Proc. Natl. Acad. Sci., 97(7):3388-3393.

Wang, et al. (1994). Deletion Of T Lymphocytes In Human CD4 Transgenic Mice Induced By HIV-gp120 and gp120-Specific Antibodies From AIDS . . . Eur. J. Immunol., 24:1553-1557.

Wanda, P.E., and Smith, J.D., (1982). A General Method For Heterokaryon Detection Using Resonance Energy Transfer And A . . . J. Histochem. & Cytochem. 30(12):1297-1300.

Weinhold, K.J., et al. (1989). HIV-1 gp120-Mediated Immune Suppresion And Lymphocyte Destruction In The Absence Of Viral Infection. J. Immunol., 142:3091-3097.

Wells, T.N.C., et al. (1996). Selectivity And Antagonism Of Chemokine Receptors. Journal of Leukocyte Biology, 59:53-60.

Yamagami, et al. (1994). cDNA Cloning And Functional Expression Of Human Monocyte Chemoattractant Protein 1 Receptor. Biochem. Biophys. Res. Commun., 212:1156-1162.

Yarchoan, et al. (1988). "Clinical Aspects Of Infection . . . ", in AIDS: Etiology, Diagnosis, . . . , De Vita, et al., eds., Lippincott-Raven Publishers, Philadelphia. pp. 107-109.

Yarchoan, R. and Broder, S. (1992). Correlations Between The In Vitro And The In Vivo Activity Of Anti-HIV Agents: Implications For . . . J. Enzyme Inhibit., 6-99-11.

Zhang, Y.J., et al. (1994). Structure / Activity Analysis Of Human Monocyte Chemoattractant Protein-1 (MCP-1) By Mutagenesis. J. Biol. Chem., 269:15918-15924.

Feb. 15, 1996 Advisory Action in connection with U.S. Appl. No. 08/169,311.

Sep. 13, 1995 Final Office Action in connection with U.S. Appl. No. 08/169,311.

Nov. 23, 1994 Office Action in connection with U.S. Appl. No. 08/169,311.

Aug. 18, 1994 Office Action in connection with U.S. Appl. No. 08/169,311.

Jul. 16, 1998 Notice of Acceptance in connection with Australian Application No. 14387/95.

Nov. 27, 1996 Examiner's First Report in connection with Australian Application No. 14387/95.

Jul. 5, 2000 Notice of Acceptance in connection with Australian Application No. 62690/96.

Nov. 10, 1998 Examiner's First Report in connection with Australian Application No. 62690/96.

Sep. 14, 2006 Official Action in connection with Canadian Application No. 2,224,003.

Sep. 11, 2006 Communication Pursuant to Article 96(2) EPC in connection with European Application No. 96 921 473.3.

Mar. 8, 2006 Summons to Oral Proceedings Pursuant to Rule 71(1) EPC in connection with European Application No. 96 921 473.3.

Feb. 24, 2005 Provision of a Copy of the Minutes in accordance with Rule 76(4) EPC in connection with European Application No. 96 921 473.3.

Feb. 24, 2005 Decision to Refuse a European Patent Application in connection with European Application No. 96 921 473.3.

Aug. 30, 2004 Summons to Oral Proceedings Pursuant to Rule 71(1) EPC in connection with European Application No. 96 921 473.3.

Dec. 19, 2002 Communication Pursuant to Article 96(2) EPC in connection with European Application No. 96 921 473.3.

Jul. 6, 2001 Communication Pursuant to Article 96(2) EPC in connection with European Application No. 96 921 473.3.

Dec. 20, 1999 Notice of Allowance and Allowability in connection with U.S. Appl. No. 08/973,601.

Aug. 3, 1999 Advisory Action in connection with U.S. Appl. No. 08/973,601.

Mar. 25, 1999 Office Action in connection with U.S. Appl. No. 08/973,601.

Jun. 24, 1998 Office Action in connection with U.S. Appl. No. 08/973,601.

Jan. 11, 2005 Notice of Allowance and Allowability in connection with U.S. Appl. No. 09/412,284.

Dec. 2, 2003 Final Office Action in connection with U.S. Appl. No. 09/412,284.

Feb. 3, 2003 Office Action in connection with U.S. Appl. No. 09/412,284.

Apr. 8, 2002 Advisory Action in connection with U.S. Appl. No. 09/412,284.

Sep. 11, 2001 Final Office Action in connection with U.S. Appl. No. 09/412,284.

Dec. 19, 2000 Office Action in connection with U.S. Appl. No. 09/412,284.

Apr. 18, 2007 Office Action in connection with U.S. Appl.No. 11/258,963.

Dec. 26, 2006 Office Action in connection with U.S. Appl. No. 11/258,963.

Feb. 8, 2007 Office Action in connection with U.S. Appl. No. 09/904,356.

May 2, 2006 Final Office Action in connection with U.S. Appl. No. 09/904,356.

Oct. 12, 2005 Office Action in connection with U.S. Appl. No. 09/904,356.

Jul. 29, 2005 Advisory Action in connection with U.S. Appl. No. 09/904,356.

Nov. 17, 2004 Final Office Action in connection with U.S. Appl. No. 09/904,356.

Jul. 1, 2003 Office Action in connection with U.S. Appl. No. 09/904,356.

Sep. 29, 2003 Advisory Action in connection with U.S. Appl. No. 09/118,415.

Jan. 28, 2003 Final Office Action in connection with U.S. Appl. No. 09/118,415.

Apr. 9, 2002 Office Action in connection with U.S. Appl. No. 09/118,415.

Aug. 14, 2001 Advisory Action in connection with U.S. Appl. No. 09/118,415.

Nov. 24, 2000 Final Office Action in connection with U.S. Appl. No. 09/118,415.

Feb. 11, 2000 Office Action in connection with U.S. Appl. No. 09/118,415.

Aug. 3, 2006 Notice of Allowance and Allowability in connection with U.S. Appl. No. 09/891,062.

Jul. 17, 2006 Notice of Allowability in connection with U.S. Appl. No. 09/891,062.

May 18, 2006 Notice of Allowance and Allowability in connection with U.S. Appl. No. 09/891,062.

Aug. 8, 2005 Office Action in connection with U.S. Appl. No. 09/891,062.

Mar. 21, 2005 Office Action in connection with U.S. Appl. No. 09/891,062.

May 28, 2004 Advisory Action in connection with U.S. Appl. No. 09/891,062.
Sep. 24, 2003 Final Office Action in connection with U.S. Appl. No. 09/891,062.
Dec. 18, 2002 Office Action in connection with U.S. Appl. No. 09/891,062.
Apr. 30, 2007 Notice of Allowance and Allowability in connection with U.S. Appl. No. 11/544,346.
Mar. 3, 1997 Office Action in connection with U.S. Appl. No. 08/627,684.
Jun. 23, 1997 Office Action in connection with U.S. Appl. No. 08/663,616.
Mar. 13, 1997 Office Action in connection with U.S. Appl. No. 08/673,682.
Nov. 28, 2000 Notice of Acceptance in connection with Australian Application No. 26074/97.
Jul. 13, 1999 Examiner's First Report in connection with Australian Application No. 26074/97.
Oct. 23, 2006 Official Action in connection with Canadian Application No. 2,250,829.
May 27, 2005 Official Action in connection with Canadian Application No. 2,250,829.
May 4, 2007 Summons to Attend Oral Proceedings Pursuant to Rule 71(1) EPC in connection with European Application No. 97917856.3.
Jan. 27, 2006 Communication Pursuant to Article 96(2) EPC in connection with European Application No. 97917856.3.
Oct. 21, 2005 Communication Pursuant to Article 115(2) EPC in connection with European Application No. 97917856.3.
Apr. 1, 2005 Communication Pursuant to Article 96(2) EPC in connection with European Application No. 97917856.3.
Aug. 5, 2004 Communication Pursuant to Article 96(2) EPC in connection with European Application No. 97917856.3.
Jan. 27, 2004 Communication Pursuant to Article 96(2) EPC in connection with European Application No. 97917856.3.
May 9, 2003 Communication Pursuant to Article 96(2) EPC in connection with European Application No. 97917856.3.
Mar. 6, 2002 Search Report Communication in connection with European Application No. 97917856.3.
Feb. 27, 2007 Notification of Reasons for Rejection in connection with Japanese Application No. 535610/97 (English translation).
May 19, 2006 Examiner's First Report in connection with Australian Application No. 2004233505.
Jul. 26, 2004 Notice of Acceptance in connection with Australian Application No. 35106/01.
Jul. 5, 2004 Examiner's Second Report in connection with Australian Application No. 35106/01.
Nov. 1, 2002 Examiner's First Report in connection with Australian Application No. 35106/01.
Dec. 4, 2001 Notice of Allowance and Allowability in connection with U.S. Appl. No. 08/831,823.
Jan. 16, 2001 Notice of Allowance and Allowability in connection with U.S. Appl. No. 08/831,823.
Sep. 26, 2000 Advisory Action in connection with U.S. Appl. No. 08/831,823.
Apr. 11, 2000 Final Office Action in connection with U.S. Appl. No. 08/831,823.
Jul. 21, 1999 Final Office Action in connection with U.S. Appl. No. 08/831,823.
Dec. 21, 1998 Office Action in connection with U.S. Appl. No. 08/831,823.
Aug. 17, 1998 Office Action in connection with U.S. Appl. No. 08/831,823.
Jun. 15, 2006 Final Office Action in connection with U.S. Appl. No. 09/888,938.
Sep. 7, 2005 Office Action in connection with U.S. Appl. No. 09/888,938.
Aug. 4, 2004 Office Action in connection with U.S. Appl. No. 09/888,938.
May 5, 2004 Office Action in connection with U.S. Appl. No. 09/888,938.
Jun. 22, 1999 Notice of Allowance and Allowability in connection with U.S. Appl. No. 08/876,078.
Dec 21, 1998 Final Office Action in connection with U.S. Appl. No. 08/876,078.
Mar. 23, 1998 Office Action in connection with U.S. Appl. No. 08/876,078.
Jun. 16, 2006 Communication Pursuant to Article 96(2) EPC in connection with European Application No. 98 931 261.6.
Jun. 17, 2005 Communication Pursuant to Article 96(2) EPC in connection with European Application No. 98 931 261.6.
Oct. 17, 2006 Final Office Action in connection with U.S. Appl. No. 09/460,216.
Feb. 3, 2006 Office Action in connection with U.S. Appl. No. 09/460,216.
Jul. 29, 2005 Advisory Action in connection with U.S. Appl. No. 09/460,216.
Feb. 09, 2005 Final Office Action in connection with U.S. Appl. No. 09/460,216.
Sep. 26, 2003 Advisory Action in connection with U.S. Appl. No. 09/460,216.
Feb. 27, 2003 Final Office Action in connection with U.S. Appl. No. 09/460,216.
Oct. 2, 2001 Office Action in connection with U.S. Appl.No. 09/460,216.
Sep. 9, 2002 Notice of Acceptance in connection with Australian Application No. 81426/98.
Feb. 27, 2002 Examiner's Second Report in connection with Australian Application No. 81426/98.
Feb. 21, 2001 Examiner's First Report in connection with Australian Application No. 81426/98.
Feb. 4, 1997 Office Action in connection with U.S. Appl. No. 08/665,090.
Aug. 29, 2000 Notice of Allowance and Allowability in connection with U.S. Appl. No. 08/874,618.
Nov. 19, 1999 Office Action in connection with U.S. Appl. No. 08/874,618.
May 24, 1999 Final Office Action in connection with U.S. Appl. No. 08/874,618.
Sep. 2, 1998 Office Action in connection with U.S. Appl. No. 08/874,618.
Dec. 13, 2005 Final Office Action in connection with U.S. Appl. No. 09/724,105.
Mar. 23, 2005 Office Action in connection with U.S. Appl. No. 09/724,105.
Sep. 23, 2004 Office Action in connection with U.S. Appl. No. 09/724,105.
May 19, 2004 Office Action in connection with U.S. Appl. No. 09/724,105.
Dec. 19, 2006 Office Action in connection with U.S. Appl. No. 11/400,497.
Aug. 8, 2006 Office Action in connection with U.S. Appl. No. 11/400,497.
May 29, 2001 Notice of Acceptance in connection with Australian Application No. 34026/97.
Sep. 28, 1999 Examiner's First Report in connection with Australian Application No. 34026/97.
Nov. 10, 2006 Official Action in connection with Canadian Application No. 2,257,991.
May 23, 2005 Communications Pursuant to Article 96(2) EPC in connection with European Application No. 97 930 120.7.
Nov. 17, 2004 Communication of partial European search report under Rule 45 EPC in connection with European Application No. 97 930 120.7.
Sep. 9, 2004 Communication of partial European search report under Rule 46(1) EPC in connection with European Application No. 97 930 120.7.
Oct. 17, 2006 Notification of Reasons for Rejection in connection with Japanese Application No. 501895/98 (English translation).
Apr. 5, 2004 Notice of Acceptance in connection with Australian Application No. 21996/00
Feb. 5, 2003 Examiner's First Report in connection with Australian Application No. 21996/00.
Mar. 29, 2006 Examiner's First Report in connection with Australian Application No. 20004205164.

Mar. 29, 2006 Examiner's First Report in connection with Australian Application No. 20004205165.
Mar. 1, 2006 Communication under Rule 51(4) EPC in connection with European Application No. 99 966 466.7.
Jan. 10, 2005 Communication Pursuant to Article 96(2) EPC in connection with European Application No. 99 966 466.7.
Oct. 14, 2004 Communication Pursuant to Article 96(1) and Rule 51(1) EPC in connection with European Application No. 99 966 466.7.
Jan. 18, 2007 Office communication in connection with Mexican Application No. 1006097.
Oct. 13, 2005 Office communication in connection with Mexican Application No. 1006097.
Feb. 6, 2007 Notice of Allowability in connection with U.S. Appl. No. 09/464,902.
Jan. 8, 2007 Notice of Allowance and Allowability in connection with U.S. Appl. No. 09/464,902.
Apr. 19, 2006 Office Action in connection with U.S. Appl. No. 09/464,902.
Oct. 21, 2005 Office Action in connection with U.S. Appl. No. 09/464,902.
Jun. 15, 2005 Advisory Action in connection with U.S. Appl. No. 09/464,902.
Jan. 13, 2005 Final Office Action in connection with U.S. Appl. No. 09/464,902.
Apr. 2, 2004 Office Action in connection with U.S. Appl. No. 09/464,902.
Oct. 21, 2003 Office Action in connection with U.S. Appl. No. 09/464,902.
Sep. 25, 2001 Office Action in connection with U.S. Appl. No. 09/464,902.
Aug. 7, 2006 Office Action in connection with U.S. Appl. No. 09/594,983.
Mar. 24, 2006 Notice of Allowance and Allowability in connection with U.S. Appl. No. 09/594,983.
Jul. 11, 2005 Final Office Action in connection with U.S. Appl. No. 09/594,983.
Aug. 25, 2004 Office Action in connection with U.S. Appl. No. 09/594,983.
Sep. 23, 2003 Notice of Allowability in connection with U.S. Appl. No. 09/594,983.
Dec. 3, 2002 Final Office Action in connection with U.S. Appl. No. 09/594,983.
Mar. 13, 2002 Office Action in connection with U.S. Appl. No. 09/594,983.
Sep. 28, 2001 Office Action in connection with U.S. Appl. No. 09/594,983.
Dec. 19, 2006 Notice of Allowance and Allowability in connection with U.S. Appl. No. 10/763,545.
Jul. 26, 2006 Office Action in connection with U.S. Appl. No. 10/763,545.
Jun. 13, 2006 Office Action in connection with U.S. Appl. No. 10/763,545.
Feb. 16, 2006 Office Action in connection with U.S. Appl. No. 10/763,545.
Feb. 9, 2004 Office action in connection with U.S. Appl. No. 10/116,797.
Apr. 21, 2006 Supplementary European search report under Article 157 (2)(a) in connection with European Application No. 03 713 632.2.
May 16, 2006 Notice of Allowance and Allowability in connection with U.S. Appl. No. 10/371,483.
Oct. 24, 2006 Office Action in connection with U.S. Appl. No. 10/371,483.
Jan. 29, 2007 Examiner's First Report in connection Australian Application No. 2003217674.
Feb. 22, 2007 Communication Pursuant to Article 96(2) EPC in connection with European Application No. 03 713 632.2.
Oct. 12, 2004 Communication Pursuant to Rules 109 and 110 EPC in connection with European Application No. 03 713 632.2.
Mar. 14, 2006 Examination Report in connection with New Zealand Application No. 534947.

Feb. 21, 2003 Official Action in connection with Russian Federation Application No. 2004128252/13(030609) (English Translation).
Sep. 29, 2006 Grant of Patent in connection with Singaporean Application No. 200404610-8.
Aug. 7, 2002 Office Action in connection with U.S. Appl. No. 09/663,219.
Jan. 5, 2006 Notice of Allowance and Allowability in connection with U.S. Appl. No. 09/912,824.
Jan. 26, 2005 Final Office Action in connection with U.S. Appl. No. 09/912,824.
Apr. 20, 2004 Office Action in connection with U.S. Appl. No. 09/912,824.
Jul. 2, 2003 Office Action in connection with U.S. Appl. No. 09/912,824.
Jul. 3, 2006 Notice of Acceptance in connection with Australian Application No. 2001290925.
Jun. 28, 2005 Examiner's First Report in connection with Australian Application No. 2001290925.
May 24, 2006 Supplementary European search report under Article 157(2)(a) EPC in connection with European Application No. 01970984.9.
Feb. 28, 2005 Formalities Examination in connection with European Application No. 01970984.9.
May 2, 2003 Communication Pursuant to Rules 109 and 110 EPC in connection with European Application No. 01970984.9.
Oct. 25, 2005 Notice of Allowance and Allowability in connection with U.S. Appl. No. 09/828,615.
Sep. 13, 2005 Office Action in connection with U.S. Appl. No. 09/828,615.
Mar. 2, 2005 Office Action in connection with U.S. Appl. No. 09/828,615.
Sep. 17, 2004 Final Office Action in connection with U.S. Appl. No. 09/828,615.
Feb. 23, 2004 Final Office Action in connection with U.S. Appl. No. 09/828,615.
Sep. 9, 2003 Advisory Action in connection with U.S. Appl. No. 09/828,615.
Feb. 21, 2003 Final Office Action in connection with U.S. Appl. No. 09/828,615.
Jun. 25, 2002 Office Action in connection with U.S. Appl. No. 09/828,615.
Max, E. "Immunoglobulins: Molecular Genetics" in Fundamental Imunology, 6th edition. W.E. Paul, ed., Lippincott-Raven Publishers, Philadelphia, 2008 pp. 192-236.
Sanders et al. (2002) "The Mannose-Dependent Epitope for Neutralizing Antibody 2G12 on Human Immunodeficiency Virus Type 1 Glycoprotein gp120," Journal of Virology, pp. 7293-7305.
Schroeder et al. (2008) "Immunoglobulins: Structure and Function," Fundamental Immunology, 6th Edition, Chapter 4, pp. 125-151.
Nelson et al. "Efficacy and Safety of Maraviroc plus Optimized Background Therapy in Viremic, ART-experienced Patients Infected with CCR5-tropic HIV-1 in Europe, Australia, and North America: 24-Week results," 14th Annual Conference on Retroviruses and Opportunistic Infections. Feb 28, 2007. Abstract #104aLB. Downloaded Aug 3, 2008 <http://www.retroconference.org/2007/Abstracts/30636.htm>.
Jul. 9, 2008 Office Action issued in connection with U.S. Appl. No. 11/258,963.
Jul. 1, 2008 Office Action issued in connection with U.S. Appl. No. 11/581,944.
Jan. 9, 2008 Final Office Action issued in connection with U.S. Appl. No. 11/258,963.
May 29, 2008 Office Action issued in connection with U.S. Appl. No. 11/259,540.
Nov. 19, 2007 Final Office Action issued in connection with U.S. Appl. No. 09/904,356.
Apr. 9, 2008 Office Action issued in connection with U.S. Appl. No. 11/451,707.
Nov. 2, 2007 Office Action issued in connection with U.S. Appl. No. 11/805,573.
Sep. 21, 2007 Notice of Allowance and Fee(s) Due, including a Notice of Allowability, issued in connection with U.S. Appl. No. 11/544,346, now U.S. Patent No. 7,345,153.

Oct. 4, 2007 Office Action issued in connection with U.S. Appl. No. 11/175,815.
Nov. 16, 2007 Office Action issued in connection with U.S. Appl. No. 09/460,216.
Sep. 12, 2007 Final Office Action issued in connection with U.S. Appl. No. 11/400,497.
Jan. 9, 2008 Office Action issued in connection with U.S. Appl. No. 11/259,540.
May 22, 2008 Office Action issued in connection with U.S. Appl. No. 11/491,330.
Aug. 5, 2008 Final Office Action issued in connection with U.S. Appl. No. 11/175,815.
Aug. 19, 2008 Office Action issued in connection with U.S. Appl. No. 11/804,746.
May 14, 2008 Office Action issued in connection with U.S. Appl. No. 11/400,497.
Mar. 11, 2008 Office Action issued in connection with U.S. Appl. No. 09/888,938.
May 31, 2007 Office Action issued in connection with U.S. Appl. No. 09/888,938.
Aug. 21, 2008 Office Action issued in connection with U.S. Appl. No. 09/904,356.
Sep. 11, 2008 Office Action issued in connection with U.S. Appl. No. 11/805,573.
Apr. 9, 2008 Office Action issued in connection with U.S. Appl. No. 11/316,078.
Notification of Transmittal of the International Search Report and the Written Opinion of the International Searching Authority, Or the Declaration issued Aug. 15, 2008 in connection with PCT International Application No. PCT/US08/05564.
Notification of Transmittal of the International Search Report and the Written Opinion of the International Searching Authority, Or the Declaration issued Jul. 25, 2008 in connection with PCT International Application No. PCT/US06/28565.
Jun. 18, 2008 Communication including Partial European Search Report in connection with European Patent Application No. 07 01 4859.8.
Combadiere, C. et al. (1995) Additions and Corrections to "Cloning and functional expression of a human eosinophil CC chemokine receptor," J. Biol. Chem. 270(28) 16491-16494.
May 15, 2008 Office Action issued in connection with U.S. Appl. No. 11/581,945.
Sep. 19, 2008 Final Office Action issued in connection with U.S. Appl. No. 09/460,216.
Sep. 16, 2008 Communication including a May 29, 2008 Extended European Search report in connection with European Patent Application No. 07014859.8.
Oct. 2, 2008 Communication Pursuant to Article 94(3) EPC and Result of Consultation issued in connection with European Patent Application No. 01970984.9.
Office Action issued Nov. 10, 2008 in connection with U.S. Appl. No. 11/400,497.
Office Action issued Dec. 12, 2008 in connection with U.S. Appl. No. 11/491,330.
Final Office Action issued Dec. 31, 2008 in connection with U.S. Appl. No. 11/581,945.
Final Office Action issued Jan. 9, 2009 in connection with U.S. Appl. No. 11/451,707.
Final Office Action issued Jan. 27, 2009 in connection with U.S. Appl. No. 11/520,556.
Final Office Action issued Jan. 27, 2009 in connection with U.S. Appl. No. 11/259,540.
Simmons, G. et al. (1996) "Primary, syncytium-inducing human immunodeficiency virus type 1 isolates are dual-tropic and most can use either Lestr or CCR5 as coreceptors for virus entry," J. Virol. 70(12):8355-8360.
Valentin, A. et al. (1994) "Dual tropism for macrophages and lymphocytes is a common feature of primary human immunodeficiency virus type 1 and 2 isolates," J. Virol. 68(10):6684-6689.
Final Office Action issued Feb. 4, 2009 in connection with U.S. Appl. No. 11/316,078.
Mar. 25, 2009 Office Action issued in connection with U.S. Appl. No. 11/175,815.

Extended European Search Report, including a European Search Report and a European Search Opinion, issued Apr. 17, 2009 in connection with European Patent Application No. 08168669.3.
May 1, 2009 Final Office Action issued in connection with U.S. Appl. No. 11/258,963.
Notification of Transmittal of the International Search Report and the Written Opinion of the International Searching Authority, or the Declaration issued May 8, 2009 in connection with PCT International Publication No. PCT/US08/08752.
Prado, J. et al. (2002) "Amprenavir-resistant HIV-1 exhibits lopinavir cross-resistance and reduced replication capacity," AIDS, vol. 16, pp. 1009-1017.
Hanna, G. et al. (2000) "Patterns of Resistance Mutations Selected by Treatment of Human Immunodeficiency Virus Type 1 Infection with Zidovudine, Didanosine, and Nevirapine," vol. 181, pp. 904-911.
Greenberg, M. and Cammack, N. (2004) "Resistance to enfuvirtide, the first HIV fusion inhibitor," vol. 54, pp. 333-340.
May 13, 2009 Office Action issued in connection with U.S. Appl. No. 09/904,356.
Jun. 23, 2009 Final Office Action issued in connection with U.S. Appl. No. 11/805,573.
Jun. 26, 2009 Final Office Action issued in connection with U.S. Appl. No. 11/581,944.
Jun. 23, 2009 Final Office Action issued in connection with U.S. Appl. No. 09/460,216.
Jun. 26, 2009 Office Action issued in connection with U.S. Appl. No. 11/520,556.
Jul. 14, 2009 Final Office Action issued in connection with U.S. Appl. No. 11/804,746.
Aug. 7, 2009 Advisory Action issued in connection with U.S. Appl. No. 11/581,945.
Allaway, G.P. et al., (1993) "Synergistic Inhibition Of HIV-1 Envelope-Mediated Cell Fusion By CD4-Based Molecules In Combination With Antibodies To gp120 Or gp41", *AIDS Res Hum Retroviruses* 9:581-587.
Allaway, G.P. et al., (1995) "Expression And Characterization Of CD4-IgG2, A Novel Heterotetramer That Neutralizes Primary HIV Type 1 Isolates", AIDS Res Hum Retrovirus 11:533-539.
Amara, A. et al., (1997) "HIV Coreceptor Downregulation As Antiviral Principle: SDF-1α-Dependent Internalization Of The Chemokine Receptor CXCR4 Contributes To Inhibition Of HIV Replication", *J. Exp. Med*. 186:139-146.
Arthos, J. et al., (1989) "Identification Of The Residues In Human CD4 Critical For The Binding Of HIV", Cell 57:469-481.
Berger, E.A., (1997) "HIV Entry And Tropism: The Chemokine Receptor Connection", AIDS 11(Suppl A):S3-S16.
Bieniasz, P.D. et al., (1997) "HIV-1 Induced Cell Fusion Is Mediated By Multiple Regions Within Both The Viral Envelope And The CCR5 Co-Receptor", EMBO 16:2599-2609.
Brelot, A. et al., (1997) "Role Of The First And Third Extracellular Domains Of CXCR4 In Human Immunodeficiency Virus Coreceptor Activity", J. Virol. 71:4744-4751.
Burkly, L. et al., (1995) "Synergistic Inhibition Of Human Immunodeficiency Virus Type 1 Envelope Glycoprotein-Mediated Cell Fusion And Infection By An Antibody To CD4 Domain 2 In Combination With Anti-gp-120 Antibodies", *J. Virol*. 69:4267-4273.
Burton, D.R. et al., (1994) "Efficient Neutralization Of Primary Isolates Of HIV-1 By A Recombinant Human Monoclonal Antibody", Science 266:1024-1027.
Capon, D.J. et al., (1989) "Designing CD4 Immunoadhesions For AIDS Therapy", Nature 337:525-531.
Chan, D.C. et al., (1998) "Evidence That A Prominent Cavity In The Coiled Coil Of HIV Type 1 gp41 Is An Attractive Drug Target", Proc. Natl. Acad. Sci. 95:15613-15617.
Chan, D.C. et al., (1998) "HIV Entry And Its Inhibition", *Cell* 93:681-684.
Chen, Z. et al., (1997) "Genetically Divergent Strains Of Simian Immunodeficiency Virus Use CCR5 As A Coreceptor For Entry", *J. Virol*. 71(4):2705-2714.
Choe, H. et al., (1996) "The Beta-Chemokine Receptors CCR3 And CCR5 Facilitate Infection By Primary HIV-1 Isolates", *Cell* 85:1135-1148.

Clapham, P.R. et al., (1989) "Soluble CD4 Blocks The Infectivity Of Diverse Strains Of HIV And SIV For T Cells And Monocytes But Not For Brain And Muscle Cells", Nature 337:368-370.

Co. M.S. et al., (1991) "Humanized Antibodies For Antiviral Therapy" Proc. Natl. Acad. Sci. 88:2869-2873.

Connor, R.I. et al., (1997) "Change in Co-Receptor Use Correlates With Disease Progression in HIV-1 Infected Individuals", J. Exp. Med. 185:621-628.

Crump, M.P. et al., (1997) "Solution Structure And Basis For Functional Activity Of Stromal-Cell Derived Factor-1: Disassociation Of CXCR4 Activation From Binding And Inhibition Of HIV-1", EMBO 16:6996-7007.

Cushman, M. et al., (1991) "Preparation And Anti-HIV Activities Of Aurintricarboxylic Acid Fractions And Analogues: Direct Correlation Of Antiviral Potency With Molecular Weight", J. Med. Chem. 34:329-337.

Dalgleish, A.G. et al., (1984) "The CD4 (T4) Antigen Is An Essential Component Of The Receptor For The AIDS Retrovirus" Nature 312:763-766.

De Rossi, A. et al., (1995) "Synthetic Peptides From The Principle Neutralizing Domain Of Human Immunodeficiency Virus Type 1 (HIV-1) Enhance HIV-1 Infection Through A CD4-Dependent Mechanism", Virology 184:187-196.

Deen, K.C. et al., (1988) "A Soluble Form Of CD4(T4) Protein Inhibits AIDS Virus Infection", Nature 331:82-84.

Deng, H. et al., (1996) "Identification Of A Major Co-Receptor For Primary Isolates of HIV-1", Nature 381:661-666.

Donzella, G.A. et al., (1998) "AMD3100, A Small Molecule Inhibitor Of HIV-1 Entry Via The CXCR4 Co-Receptor", Nat. Med. 4:72-77.

Doranz, B.J. et al., (1996) "A Dual-Tropic Primary HIV-1 Isolate That Uses Fusin And Beta-Chemokine Receptors CKR-5, CKR-3 and CKR-2b As Fusion Cofactors", Cell 85:1149-1158.

Doranz, B.J. et al., (1997) "A Small Molecule Inhibitor Directed Against The Chemokine Receptor CXCR4 Prevents Its Use As An HIV-1 Co-Receptor", J. Ex. Med. 186:1395-1400.

Doranz, B.J. et al., (1997) "Two Distinct CCR5 Domains Can Mediate Co-Receptor Usage By Human Immunodeficiency Virus Type 1", J. Virol. 71:6305-6314.

Dragic, T.V. et al., (1996) "HIV-1 Entry Into CD4+Cells Is Mediated By The Chemokine Receptor CC-CKR-5", Nature 381:667-673.

Eckert, D.M. et al., (1999) "Inhibiting HIV-1 Entry: Discovery Of D-Peptide Inhibitors That Target The gp41 Coiled-Coil Pocket", Cell 99:103-115.

Feng, Y. et al., (1996) "HIV-1 Entry Cofactor: Functional Cdna Cloning Of A Seven-Transmembrane, G Protein-Coupled Receptor", Science 272:872-877.

Ferrer, M. et al., (1999) "Selection Of gp-41 Mediated HIV-1 Cell Entry Inhibitors From Biased Combinatorial Libraries Of Non-Natural Binding Elements", Nature Struct. Biol. 6:953-959.

Fouts, T.R. et al., (1997) "Neutralization Of The Human Immunodeficiency Virus Type 1 Primary Isolate JR-FL By Human Monoclonal Antibodies Correlates With Antibody Binding To The Oligomeric Form Of The Envelope Glycoprotein Complex", J. Virol. 71:2779-2785.

Fradd, F. and Mary, M.E. (1989) "AIDS Vaccines: An Investor's Guide By Shearman Lehaman Hutton", p. 10 (Fig. 2).

Furuta, R.A. et al., (1998) "Capture Of An Early Fusion-Active Conformation Of HIV-1 gp41", Nature Struct. Biol. 5(4):276-279.

Gait, M.J and Karn, J., (1995) "Progress In Anti-HIV Structure Based Drug Design", Trends Biotechnol. 13:430-438.

Gauduin, M.C. et al., (1996) "Effective Ex Vivo Neutralization Of Human Immunodeficiency Virus Type 1 In Plasma By Recombinant Immunoglobulin Molecules", J. Virol. 70:2586-2592.

Gauduin, M.C. et al., (1997) "Passive Immunization With A Human Monoclonal Antibody Protects hu-PBL-SCID Mice Against Challenge By Primary Isolates Of HIV-1", Nat. Med. 3:1389-1393.

Hill, C.M. et al., (1998) "The Amino Terminus Of Human CCR5 Is Required For Its Function As A Receptor For Diverse Human And Simian Immunodeficiency Virus Envelope Glycoproteins", Virology 248:357-371.

Jacobson, J. et al., (1999) "Results Of A Phase I Trial Of Single-Dose PRO 542, A Novel Inhibitor Of HIV Entry", Abstracts Of The 39th Interscience Conference On Antimicrobial Agents And Chemotherapy 14.

Ji. H. et al., (1999) "Inhibition Of Human Immunodeficiency Virus Type 1 Infectivity By The gp41 Core: Role Of A Conserved Hydrophobic Cavity In Membrane Fusion", J. Virol 73:8578-8586.

Jiang, S. et al., (1993) "HIV-1 Inhibition By A Peptide", Nature 365: 113.

Kilby, J.M. et al., (1998) "Potent Suppression Of HIV-1 Replication In Humans By T-20, A Peptide Inhibitor Of gp41-Mediated Virus Entry", Nat. Med. 4:1302-1307.

Kwong P.D. et al., (1998) "Structure Of An HIV gp120 Envelope Glycoprotein In Complex With The CD4 Receptor And Neutralizing Human Antibody", Nature 393:648-659.

Laal. S. et al., (1994) "Synergistic Neutralization Of Human Immunodeficiency Virus Type 1 By Combinations Of Human Monoclonal Antibodies", J. Virol 68:4001-4008.

Lacasse, R.A. et al., (1999) "Fusion-Competent Vaccines: Broad Neutralization Of Primary Isolates Of HIV", Science 283:357-362.

Lee, B. et al., (1999) "Epitope Mapping Of CCR5 Reveals Multiple Conformational States And Distinct But Overlapping Structures Involved In Chemokine Coreceptor Function", J. Biol. Chem. 274:9617-9626.

Lehner, T. et al., (2001) "Immunogenicity Of The Extracellular Domains Of C-C Chemokine Receptor 5 And The In Vitro Effects On Simian Immunodeficiency Or HIV Infectivity", J. Immunol. 166(12):7446-7455.

Li, A. et al., (1997) "Synergistic Neutralization Of A Chimeric SIV/HIV Type 1 Virus With Combinations Of Human Anti-HIV Type 1 Envelope Monoclonal Antibodies Or Hyperimmune Globulins", AIDS Res. Hum. Retroviruses 13:647-56.

Li, A.H. et al., (1998) "Synergistic Neutralization Of Simian-Human Immunodeficiency Virus SHIV-Vpu+ By Triple And Quadruple Combination Of Human Monoclonal Antibodies And High-Titer Antihuman Immunodeficiency Virus Type 1 Immunoglobulins", J. Virol. 72:3235-3240.

Litwin, V. et al., (1996) "Human Immunodeficiency Virus Type 1 Membrane Fusion Mediated By A Laboratory-Adapted Strain And A Primary Isolate Analyzed By Resonance Energy Transfer", J. Virol. 70(9):6437-6441.

Mack, M. et al., (1998) "Aminooxypentane-RANTES Induces CCR5 Internalization But Inhibits Recycling: A Novel Inhibitory Mechanisms Of HIV Infectivity", J. Exp. Med. 187:1215-1224.

Mackay, C.R., (1996) "Chemokine Receptors And T Cell Chemotaxis", J. Exp. Med. 84: 799-802.

Markosyan, R.M. et al., (2002) "The Mechanism Of Inhibition Of HIV-1 Entry Env-Mediated Cell-Cell Fusion By Recombinant Cores Of gp41 Ectodomain", Virology 302:174-184.

McKnight, A.D. et al., (1997) "Inhibition of Human Immunodeficiency Virus Fusion By A Monoclonal Antibody To A Coreceptor (CXCR4) Is Both Cell Type And Virus Strain Dependent", J. Virol. 71:1692-1696.

Mohan, P. et al., (1992) "Sulfonic Acid Polymers As A New Class of Human Immunodeficiency Virus Inhibitors", Antiviral Res. 18:139-150.

Nagashima, K.A. et al., (2001) "Human Immunodeficiency Virus Type 1 Entry Inhibitors PRO 542 And T-20 Are Potently Synergistic In Blocking Virus-Cell And Cell-Cell Fusion", J. Infect. Dis. 183:1121-1125.

Olson, W.C. et al., (1999) "Differential Inhibition Of Human Immunodeficiency Virus Type 1 Fusion, gp 120 Binding And CC-Chemokine Activity Of Monoclonal Antibodies To CCR5", J. Virol. 73:4145-4155.

Parren, P.W. et al., (2001) "Antibody Protects Macaques Against Vaginal Challenge With A Pathogenic R5 Simian/Human Immunodeficiency Virus At Serum Levels Giving Complete Neutralization in Vitro", J. Virol. 75:8340-8347.

Posner, M.R. et al., (1993) "Neutralization Of HIV-1 By F105, A Human Monoclonal Antibody To The CD4 Binding Site Of gp120", J. Acq. Immune Defic. Synd. 6:7-14.

Rudikoff, S. et al., (1982) "Single Amino Acid Substitution Altering Antigen-Binding Specificity", Proc. Natl. Acad. Sci. 79:1979-1983.

Schols, D. et al., (1990) "Dextran Sulfate And Other Olyanionic Anti-HIV Compounds Specifically Interact With The Viral gp120 Glycoprotein Expressed By T-Cells Persistently Infected With HIV-1", *Virol.* 175:556-561.

Schols, D. et al., (1991) "Selective Inhibitory Activity Of Polyhydroxycarboxylates Derived From Phenolic Compounds Against Human Immunodeficiency Virus Replication", *J. Acq. Immune Defic. Synd.* 4:677-685.

Strizki, J.M. et al., (1997) "A Monoclonal Antibody (12G5) Directed Against CXCR4 Inhibits Infection With The Dual-Tropic Human Immunodeficiency Virus Type 1 Isolates HIV-1 89.6 But Not The T-Tropic Isolate HIV-1 Hxb", *J. Virol.* 71:5678-5683.

Thali, M. et al., (1992) "Cooperativity Of Neutralizing Antibodies Directed Against The VS And CD4 Binding Regions Of The Human Immunodeficiency Virus gp120 Envelope Glycoprotein", *J. Acq. Immun. Defic. Synd.* 5:591-599.

Tilley, S. A. (1992) "Synergistic Neutralization Of HIV-1 By Human Monoclonal Antibodies Against The V3 Loop And The CD4-Binding Site gp120", *AIDS Research And Human Retroviruses* 80:4:461-467.

Tilley, S. A. et al., (1991) "Potent Neutralization Of HIV-1 By Human And Chimpanzee Monoclonal Antibodies Directed Against Three Distinct Epitope Clusters Of gp120", *Sixieme Colloque Des Cent Gardes* 211-216.

Tremblay, C.L. et al. (2000) "Strong in Vitro Synergy Observed Between The Fusion Inhibitor T-20 And A CXCR4 Blocker AMD-3100.", 7th Conference On Retroviruses And Opportunistic Infections Abstract 500.

Tremblay, C.L. et al., (1999) "Strong in Vitro Synergy Between The Fusion Inhibitor T-20 And The CXCR4 Blocker AMD-3100", *J. Acq. Immun. Defici. Synd.* 25(2)99-102.

Trkola, A. et al., (2001) "Potent, Broad-Spectrum Inhibition Of Human Immunodeficiency Virus Type 1 By The CCR5 Monoclonal Antibody PRO 140", *J. Virol.* 75:579-588.

Trkola, A. et al (1999) "Cross-Clade Neutralization Of Primary Isolates Of Human Immunodeficiency Virus Type 1 By Human Monoclonal Antibodies And Tetrameric CD4-IgG", *J. Virol.* 69:6609-6617.

Trkola, A. et al., (1996) "CD-4 Dependent, Antibody Sensitive Interactions Between HIV-1 And Its Co-Receptor CCR-5", *Nature* 384:184-187.

Trkola, A. et al., (1998) "Neutralization Sensitivity Of Human Immunodeficiency Virus Type 1 Primary Isolates To Antibodies And CD4-based Reagents Is Independent Of Coreceptor Usage", *J. Virol.* 72:1876-1885.

Valenzuela, A. et al., (1997) "Neutralizing Antibodies Against The V3 Loop Of Human Immunodeficiency Virus Type 1 Block The CD4-Dependent And Independent Binding Of Virus To Cells", *J. Virol.* 71(11):8289-8298.

Vijh-Warrier, S. (1996) "Synergistic Neutralization Of Human Immunodeficiency Virus Type 1 By A Chimpanzee Monoclonal Antibody Against The V2 Domain Of gp120 In Combination With Monoclonal Antibodies Against The V3 Loop And The CD4-Binding Site", *J. Virol.* 70:4466-4473.

Vita, C. et al., (1999) "Rational Engineering Of A Miniprotein That Reproduces The Core Of The CD4 Site Interacting With HIV-1 Envelope Glycoprotein", *Proc. Natl. Acad. Sci.* 96:13091-13096.

Wild, C. et al., (1992) "A Synthetic Peptide Inhibitor Of Human Immunodeficiency Virus Replication: Correlation Between Solution Structure And Viral Inhibition", *Proc. Natl. Acad. Sci.* 89:10537-10541.

Wild, C. et al., (1993) "A Synthetic Peptide From HIV-1 gp41 Is A Potent Inhibitor Of Virus Mediated Cell-Cell Fusion", *AIDS Res. Hum. Retroviruses* 9:1051-1053.

Wild, C. et al., (1994) "Peptides Corresponding To A Predictive Alpha-Helical Domain Of Human Immunodeficiency Virus Type 1 gp41 Are Potent Inhibitors Of Virus Infection", *Proc. Natl. Acad. Sci.* 91:9770-9774.

Wild, C. et al., (1995) "The Inhibitory Activity Of An HIV Type 1 Peptide Correlates With Its Ability To Interact With A Leucine Zipper Structure", *AIDS Res. Hum. Retroviruses* 11:323-325.

Wu, L. et al., (1997) "CCR5 Levels and Expression Pattern Correlate With Infectability By Macrophagetropic HIV-1 In Vitro", *J. Exp. Med.* 185(9):1681-1691.

Wu, L. et al., (1997) "Interaction of Chemokine Receptor CCR5 With Its Ligands: Multiple Domains For HIV-1 gp120 Binding And A Single Domain For Chemokine Binding", *J. Exper. Med.* 186(8):1373-1381.

Wu, L. et al., (1996) "CD4-Induced Interaction Of Primary HIV-1 Gp120 Glycoproteins With The Chemokine Receptor CCR-5", *Nature* 384:179-183.

Ylisastigui, L. et al., (1998) "Synthetic Full Length And Truncated RANTES Inhibit HIV-1 Infection Or Primary Macrophages", AIDS 12:977-984.

Pending claims in W.C. Olson et al., U.S. Appl. No. 11/316,078 filed Dec. 21, 2005 (Exhibit 1);.

Pending claims in G.P. Allaway et al., U.S. Appl. No. 11/258,963 filed Oct. 25, 2005 (Exhibit 2);.

Pending claims in W.C. Olson et al., U.S. Appl. No. 11/581,944 filed Oct. 16, 2006 (Exhibit 3);.

Pending claims in W.C. Olson et al., U.S. Appl. No. 11/581,945 filed Oct. 16, 2006 (Exhibit 4);

Pending claims in V.M. Litwin et al., U.S. Appl. No. 11/544,346 filed Oct. 5, 2006 (Exhibit 5);.

Pending claims in W.C. Olson et al., U.S. Appl. No. 09/594,983 filed Jun. 15, 2000 (Exhibit 6);.

Pending claims in W.C. Olson et al., U.S. Appl. No. 09/464,902 filed Dec. 16, 1999 (Exhibit 7);.

Pending claims in G.P. Allaway et al., U.S. Appl. No. 09/460,216 filed Dec. 13, 1999 (Exhibit 8);.

PCT International Application Publication No. WO 95/16789 published Jun. 22, 1995 (Exhibit 9);.

PCT International Application Publication No. WO 97/28258 published Aug. 7, 1997 (Exhibit 10);.

PCT International Application Publication No. WO 97/47318 published Dec. 18, 1997 (Exhibit 11);.

PCT International Application Publication No. WO 01/58915 published Aug. 16, 2001 (Exhibit 12);.

PCT International Application Publication No. WO 01/58916 published Aug. 16, 2001 (Exhibit 13);.

PCT International Application Publication No. WO 96/39437 published Dec. 12, 1996 (Exhibit 14);.

PCT International Application Publication No. WO 97/22698 published Jun. 26, 1997 (Exhibit 15);.

PCT International Application Publication No. WO 97/44055 published Nov. 27, 1997 (Exhibit 16);.

PCT International Application Publication No. WO 97/032019 published Sep. 4, 1997 (Exhibit 17);.

PCT International Application Publication No. WO 94/22477 published Oct. 13, 1994 (Exhibit 18);.

PCT International Application published Feb. 6, 2002; Publication No. WO 92/01451.

PCT International Application published Dec. 19, 1996; Publication No. WO 96/41020.

PCT International Application published Jul. 24, 1997; Publication No. WO 97/26009.

PCT International Application published Oct. 27, 1997; Publication No. WO 97/37005.

PCT International Application published Dec. 18, 1997; Publication No. WO 97/47319.

PCT International Application published Dec. 31, 1997; Publication No. WO 97/49424.

PCT International Application published Dec. 17, 1998; Publication No. WO 98/56421.

PCT International Application published Jun. 22, 2000; Publication No. WO 00/35409.

PCT International Application published Sep. 7, 2001; Publication No. WO 01/64710.

PCT International Application published Sep. 6, 2002; Publication No. WO 02/068608.

PCT International Application published Oct. 24, 2002; Publication No. WO 02/083172.

PCT International Application Publication No. WO 02/22077 published Mar. 21, 2002.

PCT International Application Publication No. WO 03/072766 published Sep. 4, 2003;.

PCT International Application Publication No. WO 97/45543 published Dec. 4, 1994;.
PCT International Application Publication No. WO 98/18826 published May 7, 1998;.
PCT International Application Publication No. WO 01/55439 published Aug. 2, 2001;.
Allaway, G.P. et al., (1993) "Synergistic Inhibition Of HIV-1 Envelope-Mediated Cell Fusion By CD4-Based Molecules In Combination With Antibodies To gp120 Or gp41", *AIDS Res Hum Retroviruses* 9:581-587;.
Allaway, G.P. et al., (1995) "Expression And Characterization Of CD4-IgG$_2$, A Novel Heterotetramer That Neutralizes Primary HIV Type 1 Isolates", *AIDS Res Hum Retrovirus* 11:533-539;.
Amara, A. et al., (1997) "HIV Coreceptor Downregulation As Antiviral Principle: SDF-1α-Dependent Internalization Of The Chemokine Receptor CXCR4 Contributes To Inhibition Of HIV Replication", *J. Exp. Med.* 186:139-146;.
Arthos, J. et al., (1989) "Identification Of The Residues In Human CD4 Critical For The Binding of HIV", *Cell* 57:469-481;.
Berger, E.A., (1997) "HIV Entry And Tropism: The Chemokine Receptor Connection", *AIDS* 11(Suppl A):S3-S16;.
Bieniasz, P.D. et al., (1997) "HIV-1 Induced Cell Fusion Is Mediated By Multiple Regions Within Both The Viral Envelope And The CCR5 Co-Receptor", *EMBO* 16:2599-2609;.
Brelot, A. et al., (1997) "Role Of The First And Third Extracellular Domains of CXCR4 In Human Immunodeficiency Virus Coreceptor Activity", *J. Virol.* 71:4744-4751;.
Burkly, L. et al., (1995) "Synergistic Inhibition Of Human Immunodeficiency Virus Type 1 Envelope Glycoprotein-Mediated Cell Fusion And Infection By An Antibody To CD4 Domain 2 In Combination With Anti-gp-120 Antibodies",*J. Virol.* 69:4267-4273;.
Burton, D.R. et al., (1994) "Efficient Neutralization Of Primary Isolates Of HIV-1 By A Recombinant Human Monoclonal Antibody", *Science* 266:1024-1027;.
Capon, D.J. et al., (1989) "Designing CD4 Immunoadhesions For AIDS Therapy", *Nature* 337:525-531;.
Chan, D.C. et al., (1998) "Evidence That A Prominent Cavity In The Coiled Coil Of HIV Type 1 gp41 Is An Attractive Drug Target", *Proc. Natl. Acad. Sci.* 95:15613-15617;.
Chan, D.C. et al., (1998) "HIV Entry And Its Inhibition", *Cell* 93:681-684;.
Chen, Z. et al., (1997) "Genetically Divergent Strains Of Simian Immunodeficiency Virus Use CCR5 As A Coreceptor For Entry", *J. Virol.* 71(4):2705-2714;.
Choe, H. et al., (1996) "The Beta-Chemokine Receptors CCR3 And CCR5 Facilitate Infection By Primary HIV-1 Isolates", *Cell* 85:1135-1148;.
Clapham, P.R. et al., (1989) "Soluble CD4 Blocks The Infectivity Of Diverse Strains Of HIV and SIV For T Cells and Monocytes But Not For Brain And Muscle Cells", *Nature* 337:368-370;.
Co. M.S. et al., (1991) "Humanized Antibodies For Antiviral Therapy" *Proc. Natl. Acad. Sci.* 88:2869-2873;.
Connor, R.I. et al., (1997) "Change In Co-Receptor Use Correlates With Disease Progression In HIV-1 Infected Individuals", *J. Exp. Med.* 185:621-628;.
Crump, M.P. et al., (1997) "Solution Structure And Basis For Functional Activity of Stromal-Cell Derived Factor-1: Disassociation Of CXCR4 Activation From Binding And Inhibition of HIV-1", *EMBO* 16:6996-7007;.
Cushman, M. et al., (1991) "Preparation And Anti-HIV Activities of Aurintricarboxylic Acid Fractions And Analogues: Direct Correlation Of Antiviral Potency With Molecular Weight", *J. Med. Chem.* 34:329-337;.
Dalgleish, A.G. et al., (1984) "The CD4 (T4) Antigen Is An Essential Component Of The Receptor For The AIDS Retrovirus" *Nature* 312:763-766;.
De Rossi, A. et al., (1995) "Synthetic Peptides From The Principle Neutralizing Domain Of Human Immunodeficiency Virus Type 1 (HIV-1) Enhance HIV-1 Infection Through A CD4-Dependent Mechanism", *Virology* 184:187-196;.
Deen, K.C. et al., (1988) "A Soluble Form Of CD4(T4) Protein Inhibits Aids Virus Infection", *Nature* 331:82-84;.
Deng, H. et al., (1996) "Identification Of A Major Co-Receptor For Primary Isolates Of HIV-1", *Nature* 381:661-666;.
Donzella, G.A. et al., (1998) "AMD3100, A Small Molecule Inhibitor Of HIV-1 Entry Via The CXCR4 Co-Receptor", *Nat. Med.* 4:72-77;.
Doranz, B.J. et al., (1996) "A Dual-Tropic Primary HIV-1 Isolate That Uses Fusin And Beta-Chemokine Receptors CKR-5, CKR-3 And CKR-2b As Fusion Cofactors",*Cell* 85:1149-1158;
Doranz, B.J. et al., (1997) "A Small Molecule Inhibitor Directed Against The Chemokine Receptor CXCR4 Prevents Its Use As An HIV-1 Co-Receptor", *J. Ex. Med.* 186:1395-1400;.
Doranz, B.J. et al., (1997) "Two Distinct CCR5 Domains Can Mediate Co-Receptor Usage By Human Immunodeficiency Virus Type 1", *J. Virol.* 71:6305-6314;.
Dragic, T.V. et al., (1996) "HIV-1 Entry Into CD4+Cells Is Mediated By The Chemokine Receptor CC-CKR-5", *Nature* 381:667673;.
Eckert, D.M. et al., (1999) "Inhibiting HIV-1 Entry: Discovery Of D-Peptide Inhibitors That Target the gp41 Coiled-Coil Pocket", *Cell* 99:103-115;.
Feng, Y. et al., (1996) "HIV-1 Entry Cofactor: Functional CDNA Cloning Of A Seven-Transmembrane, G Protein-Coupled Receptor", *Science* 272:872-877;.
Ferrer, M. et al., (1999) "Selection Of gp-41 Mediated HIV-1 Cell Entry Inhibitors From Biased Combinatorial Libraries Of Non-Natural Binding Elements ", *Nature Struct. Biol.* 6:953-959;.
Fouts, T.R. et al., (1997) "Neutralization Of The Human Immunodeficiency Virus Type 1 Primary Isolate JR-FL By Human Monoclonal Antibodies Correlates With Antibody Binding To The Oligomeric Form Of The Envelope Glycoprotein Complex", *J. Viral.* 71:2779-2785;.
Fradd, F. and Mary, M.E. (1989) "AIDS Vaccines: An Investor's Guide By Shearman Lehaman Hutton", p. 10 (Fig. 2);.
Furuta, R.A. et al., (1998) "Capture Of An Early Fusion-Active Conformation Of HIV-1 gp41", *Nature Struct. Biol.* 5(4):276- 279;.
Gait, M.J and Karn, J., (1995) "Progress In Anti-HIV Structure Based Drug Design", *Trends Biotechnol.*13:430-438;.
Gauduin, M.C. et al., (1996) "Effective Ex Vivo Neutralization Of Human Immunodeficiency Virus Type 1 In Plasma By Recombinant Immunoglobulin Molecules", *J. Virol.* 70:2586-2592;.
Gauduin, M.C. et al., (1997) "Passive Immunization With A Human Monoclonal Antibody Protects hu-PBL-SCID Mice Against Challenge By Primary Isolates Of HIV-1", *Nat. Med.* 3:13891393;.
Hill, C.M. et al., (1998) "The Amino Terminus Of Human CCR5 Is Required for Its Function As A Receptor For Diverse Human And Simian Immunodeficiency Virus Envelope Glycoproteins", *Virology* 248:357-371;.
Jacobson, J. et al., (1999) "Results Of A Phase I Trial of Single-Dose PRO 542, A Novel Inhibitor Of HIV Entry", Abstracts Of The 39th Interscience Conference On Antimicrobial Agents And Chemotherapy 14;.
Ji, H. et al., (1999) "Inhibition Of Human Immunodeficiency Virus Type 1 Infectivity By The gp41 Core: Role Of A Conserved Hydfophobic Cavity In Membrane Fusion", *J. Virol* 73:8578-8586;.
Jiang, S. et al., (1993) "HIV-1 Inhibition By A Peptide", *Nature* 365: 113;.
Kilby, J.M. et al., (1998) "Potent Suppression Of HIV-1 Replication In Humans By T-20, A Peptide Inhibitor Of gp41-Mediated Virus Entry", *Nat. Med.* 4:1302-1307;.
Kwong P.D. et al., (1998) "Structure Of An HIV gp120 Envelope Glycoprotein In Complex With The CD4 Receptor And Neutralizing Human Antibody", *Nature* 393:648-659;.
Laal, S. et al., (1994) "Synergistic Neutralization Of Human Immunodeficiency Virus Type 1 By Combinations Of Human Monoclonal Antibodies", *J. Virol* 68:4001-4008;.
Lacasse, R.A. et al., (1999) "Fusion-Competent Vaccines: Broad Neutralization Of Primary Isolates Of HIV", *Science* 283:357-362;.
Lee, B. et al., (1999) "Epitope Mapping Of CCR5 Reveals Multiple Conformational States And Distinct But Overlapping Structures Involved In Chemokine Coreceptor Function", *J. Biol. Chem.* 274:9617-9626;.
Lehner, T. et al., (2001) "Immunogenicity Of The Extracellular Domains Of C-C Chemokine Receptor 5 And The In Vitro Effects On Simian Immunodeficiency Or HIV Infectivity", *J. Immunol.* 166(12):7446-7455;.

Li, A. et al., (1997) "Synergistic Neutralization Of A Chimeric SIV/HIV Type 1 Virus With Combinations Of Human Anti-HIV Type 1 Envelope Monoclonal Antibodies Or Hyperimmune Globulins", *AIDS Res. Hum. Retroviruses* 13:647-56;.

Li, A.H. et al., (1998) "Synergistic Neutralization Of Simian-Human Immunodeficiency Virus SHIV-Vpu+ By Triple And Quadruple Combination Of Human Monoclonal Antibodies And High-Titer Antihuman Immunodeficiency Virus Type 1 Immunoglobulins", *J. Virol.* 72:3235-3240;.

Litwin, V. et al., (1996) "Human Immunodeficiency Virus Type 1 Membrane Fusion Mediated By A Laboratory-Adapted Strain And A Primary Isolate Analyzed By Resonance Energy Transfer", *J. Virol.* 70(9):6437-6441;.

Mack, M. et al., (1998) "Aminooxypentane-RANTES Induces CCR5 Internalization But Inhibits Recycling: A Novel Inhibitory Mechanisms Of HIV Infectivity", *J. Exp. Med.* 187:1215-1224;.

Mackay, C.R., (1996) "Chemokine Receptors And T Cell Chemotaxis", *J. Exp. Med.* 84: 799-802;.

Markosyan, R.M. et al., (2002) "The Mechanism Of Inhibition Of HIV-1 Entry Env-Mediated Cell-Cell Fusion By Recombinant Cores Of gp41 Ectodomain", *Virology* 302:174-184;.

McKnight, A.D. et al., (1997) "Inhibition Of Human Immunodeficiency Virus Fusion By A Monoclonal Antibody To A Coreceptor (CXCR4) Is Both Cell Type And Virus Strain Dependent", J. Virol. 71:1692-1696;.

Mohan, P. et al., (1992) "Sulfonic Acid Polymers As A New Class Of Human Immunodeficiency Virus Inhibitors", *Antiviral Res.* 18:139-150;.

Nagashima, K.A. et al., (2001) "Human Immunodeficiency Virus Type 1 Entry Inhibitors PRO 542 and T-20 Are Potently Synergistic In Blocking Virus-Cell And Cell-Cell Fusion", *J. Infect. Dis.* 183:1121-1125;.

Olson, W.C. et al., (1999) "Differential Inhibition Of Human Immunodeficiency Virus Type 1 Fusion, gp 120 Binding and CC-Chemokine Activity of Monoclonal Antibodies To CCR5", *J. Virol.* 73:4145-4155;.

Parren, P.W. et al., (2001) "Antibody Protects Macaques Against Vaginal Challenge With A Pathogenic R5 Simian/Human Immunodeficiency Virus At Serum Levels Giving Complete Neutralization *In Vitro* ", *J. Virol.* 75:8340-8347;.

Posner, M.R. et al., (1993) "Neutralization Of HIV-1 By F105, A Human Monoclonal Antibody To The CD4 Binding Site Of gp120", *J. Acq. Immune Defic. Synd.* 6:7-14;.

Rudikoff, S. et al., (1982) "Single Amino Acid Substitution Altering Antigen-Binding Specificity", *Proc. Natl. Acad. Sci.* 79:1979-1983;.

Schols, D. et al., (1990) "Dextran Sulfate And Other Olyanionic Anti-HIV Compounds Specifically Interact With The Viral gp120 Glycoprotein Expressed By T-Cells Persistently Infected With HIV-1", *Virol.* 175:556-561;.

Schols, D. et al., (1991) "Selective Inhibitory Activity Of Polyhydroxycarboxylates Derived From Phenolic Compounds Against Human Immunodeficiency Virus Replication", *J. Acq. Immune Defic. Synd.* 4:677-685;.

Strizki, J.M. et al., (1997) "A Monoclonal Antibody (12G5) Directed Against CXCR4 Inhibits Infection With The Dual-Tropic Human Immunodeficiency Virus Type 1 Isolates HIV-1 89.6 But Not The T-Tropic Isolate HIV-1 Hxb", *J. Virol.* 71:5678-5683;.

Thali, M. et al., (1992) "Cooperativity Of Neutralizing Antibodies Directed Against The VS And CD4 Binding Regions Of The Human Immunodeficiency Virus gp120 Envelope Glycoprotein", *J. Acq. Iminun. Defic. Synd.* 5:591-599;.

Tilley, S. A. (1992) "Synergistic Neutralization Of HIV-1 By Human Monoclonal Antibodies Against The V3 Loop And The CD4-Binding Site gp120", *AIDS Research And Human Retroviruses* 80:4:461-467;.

Tilley, S. A. et al., (1991) "Potent Neutralization Of HIV-1 By Human And Chimpanzee Monoclonal Antibodies Directed Against Three Distinct Epitope Clusters Of gp120", *Sixieme Colloque Des Cent Gardes* 211-216;.

Tremblay, C.L. et al. (2000) "Strong In Vitro Synergy'Observed Between The Fusion Inhibitor T-20 And A CXCR4 Blocker AMD-3100.", 7th Conference On Retroviruses And Opportunistic Infections Abstract 500 (Exhibit 19); 1

Tremblay, C.L. et al., (1999) "Strong In Vitro Synergy Between The Fusion Inhibitor T-20 And The CXCR4 Blocker AMD-3100", *J. Acq. Immun. Defici. Synd.* 25(2)99-102 (Exhibit 20);.

Trkola, A. et al., (2001) "Potent, Broad-Spectrum Inhibition Of Human Immunodeficiency Virus Type 1 By The CCR5 Monoclonal Antibody PRO 140", *J. Virol.* 75:579-588;.

Trkola, A. et al (1999) "Cross-Clade Neutralization Of Primary Isolates Of Human Immunodeficiency Virus Type 1 By Human Monoclonal Antibodies And Tetrameric CD4-IgG", *J. Virol.* 69:6609-6617;.

Trkola, A. et al., (1996) "CD-4 Dependent, Antibody Sensitive Interactions Between HIV-1 And Its Co-Receptor CCR-5", *Nature* 384:184-187;.

Trkola, A. et al., (1998) "Neutralization Sensitivity Of Human Immunodeficiency Virus Type 1 Primary Isolates To Antibodies And CD4-based Reagents Is Independent Of Coreceptor Usage", *J. Virol.* 72:1876-1885;.

Valenzuela, A. et al., (1997) "Neutralizing Antibodies Against The V3 Loop Of Human Immunodeficiency Virus Type 1 Block The CD4-Dependent And Independent Binding Of Virus To Cells", *J. Virol.* 71(11):8289-8298;.

Vijh-Warrier, S. (1996) "Synergistic Neutralization of Human Immunodeficiency Virus Type 1 By A Chimpanzee Monoclonal Antibody Against The V2 Domain Of gp120 In Combination With Monoclonal Antibodies Against The V3 Loop And The CD4-Binding Site", *J. Virol.* 70:4466-4473;.

Vita, C. et al., (1999) "Rational Engineering Of A Miniprotein That Reproduces The Core Of The CD4 Site Interacting With HIV-1 Envelope Glycoprotein", *Proc. Natl. Acad. Sci.* 96:1309113096;.

Wild, C. et al., (1992) "A Synthetic Peptide Inhibitor Of Human Immunodeficiency Virus Replication: Correlation Between Solution Structure And Viral Inhibition", *Proc. Natl. Acad. Sci.* 89:10537-10541;.

Wild, C. et al., (1993) "A Synthetic Peptide From HIV-1 gp41 Is A Potent Inhibitor Of Virus Mediated Cell-Cell Fusion", *AIDS Res. Hum. Retroviruses* 9:1051-1053;.

Wild, C. et al., (1994) "Peptides Corresponding To A Predictive Alpha-Helical Domain Of Human Immunodeficiency Virus Type 1 gp41 Are Potent Inhibitors Of Virus Infection",*Proc. Natl. Acad. Sci.* 91:9770-9774;.

Wild, C. et al., (1995) "The Inhibitory Activity Of An HIV Type 1 Peptide Correlates With Its Ability To Interact With A Leucine Zipper Structure", *AIDS Res. Hum. Retroviruses* 11:323325;.

Wu, L. et al., (1997) "CCR5 Levels And Expression Pattern Correlate With Infectability By Macrophagetropic HIV-1 In Vitro", *J. Exp. Med.* 185(9):1681-1691;.

Wu, L. et al., (1997) "Interaction Of Chemokine Receptor CCR5 With Its Ligands: Multiple Domains For HIV-1 gp120 Binding And A Single Domain For Chemokine Binding", *J. Exper. Med.* 186(8):1373-1381;.

Wu, L. et al., (1996) "CD4-Induced Interaction Of Primary HIV-1 Gp120 Glycoproteins With The Chemokine Receptor CCR-5", *Nature* 384: 179-183;.

Ylisastigui, L. et al., (1998) "Synthetic Full Length And Truncated RANTES Inhibit HIV-1 Infection Or Primary Macrophages", *AIDS* 12:977-984;.

PCT International Preliminary Examination Report issued Jun. 22, 2002 for International Application Publication No. WO 02/22077 (Exhibit 21);.

PCT International Search Report issued Apr. 23, 2002 for International Application Publication No. WO 02/22077 A2 (Exhibit 22), and.

Supplementary European Search Report issued April 27, 2006 for European Patent Application No. 01970984.9 (Exhibit 23).

* cited by examiner

Figure 2

| Percent Inhibition | Combination Index | | | |
|---|---|---|---|---|
| | CD4-IgG2:T-20 Mass Ratio | | | |
| | 25:1 (low) | 25:1 (high) | 5:1 | 1:1 |
| 95 | 0.32 | 0.20 | 0.22 | 0.50 |
| 90 | 0.38 | 0.25 | 0.27 | 0.55 |
| 85 | 0.43 | 0.29 | 0.30 | 0.59 |
| 80 | 0.47 | 0.33 | 0.34 | 0.62 |
| 75 | 0.51 | 0.36 | 0.37 | 0.65 |
| 70 | 0.54 | 0.39 | 0.40 | 0.67 |
| 65 | 0.58 | 0.42 | 0.43 | 0.70 |
| 60 | 0.61 | 0.45 | 0.45 | 0.73 |
| 55 | 0.65 | 0.48 | 0.49 | 0.75 |
| 50 | 0.69 | 0.51 | 0.52 | 0.78 |

Figure 3

| Percent Inhibition | T-20 | | | CD4-IgG2 | | |
|---|---|---|---|---|---|---|
| | Concentration, µg/ml | | Dose Reduction | Concentration, µg/ml | | Dose Reduction |
| | Alone | Combination | | Alone | Combination | |
| 99 | 1.1 | 0.17 | 6.6 | 130 | 4.3 | 29 |
| 95 | 0.21 | 0.044 | 4.9 | 19 | 1.10 | 17 |
| 90 | 0.10 | 0.024 | 4.2 | 7.8 | 0.59 | 13 |
| 70 | 0.025 | 0.0076 | 3.3 | 1.6 | 0.19 | 8.4 |
| 50 | 0.011 | 0.0039 | 2.8 | 0.60 | 0.095 | 6.3 |

Figure 4A

| Percent Inhibition | Combination Index | PRO 542 Concentration, nM Alone | PRO 542 Concentration, nM Mix | PRO 542 Dose Reduction | PA12 Concentration, nM Alone | PA12 Concentration, nM Mix | PA12 Dose Reduction | T-20 Concentration, nM Alone | T-20 Concentration, nM Mix | T-20 Dose Reduction |
|---|---|---|---|---|---|---|---|---|---|---|
| 95 | 0.41 | 10 | 2.1 | 4.8 | 730 | 2.8 | 260 | 94 | 19 | 4.9 |
| 90 | 0.45 | 7.0 | 1.6 | 4.4 | 320 | 2.1 | ~150 | 63 | 14 | 4.5 |
| 70 | 0.47 | 4.1 | 0.92 | 4.5 | 72 | 1.2 | 60 | 30 | 8.1 | 3.7 |
| 50 | 0.48 | 3.1 | 0.66 | 4.7 | 28 | 0.87 | 32 | 19 | 5.8 | 3.3 |

PRO 542, PA12 and T-20 were used in an approximate 1:1:10 molar concentration ratio.

Figure 4B

| Percent Inhibition | Combination Index | PRO 542 Concentration, nM Alone | PRO 542 Concentration, nM Mix | PRO 542 Dose Reduction | PRO 140 Concentration, nM Alone | PRO 140 Concentration, nM Mix | PRO 140 Dose Reduction | T-20 Concentration, nM Alone | T-20 Concentration, nM Mix | T-20 Dose Reduction |
|---|---|---|---|---|---|---|---|---|---|---|
| 95 | 0.40 | 8.5 | 1.9 | 4.5 | 19 | 1.0 | 19 | 140 | 17 | 8.2 |
| 90 | 0.39 | 7.1 | 1.5 | 4.7 | 13 | 0.77 | 17 | 100 | 13 | 7.7 |
| 70 | 0.37 | 5.3 | 0.87 | 6.1 | 7.2 | 0.46 | 16 | 57 | 7.7 | 7.4 |
| 50 | 0.35 | 4.6 | 0.63 | 7.3 | 4.9 | 0.34 | 14 | 40 | 5.6 | 7.1 |

PRO 542, PRO 140 and T-20 were used in an approximate 2:1:20 molar concentration ratio.

Figure 4C

| Percent Inhibition | Combination Index | PRO 542 | | | PRO 140 | | | T-20 | | |
|---|---|---|---|---|---|---|---|---|---|---|
| | | Concentration, nM | | Dose Reduction | Concentration, nM | | Dose Reduction | Concentration, nM | | Dose Reduction |
| | | Alone | Mix | | Alone | Mix | | Alone | Mix | |
| 95 | 0.24 | 61 | 2.5 | 24 | 11.9 | 0.72 | 17 | 156 | 22 | 7.1 |
| 90 | 0.22 | 32 | 1.4 | 23 | 8.4 | 0.40 | 21 | 96 | 13 | 7.4 |
| 70 | 0.19 | 9.8 | 0.50 | 20 | 4.5 | 0.14 | 32 | 40 | 4.5 | 8.9 |
| 50 | 0.18 | 4.7 | 0.26 | 18 | 3.0 | 0.074 | 41 | 23 | 2.3 | 10 |

PRO 542, PRO 140 and T-20 were used in an approximate 4:1:30 molar concentration ratio.

Figure 4D

| Percent Inhibition | Combination Index | PRO 140 Concentration, nM | | Dose Reduction | T-20 Concentration, nM | | Dose Reduction |
|---|---|---|---|---|---|---|---|
| | | Alone | Mix | | Alone | Mix | |
| 95 | 0.56 | 12 | 1.8 | 6.7 | 156 | 55 | 2.8 |
| 90 | 0.55 | 8.4 | 1.1 | 7.4 | 96 | 35 | 2.7 |
| 70 | 0.55 | 4.5 | 0.51 | 8.8 | 40 | 16 | 2.5 |
| 50 | 0.56 | 3.0 | 0.31 | 9.9 | 23 | 10 | 2.4 |

PRO 140 and T-20 were used in an approximate 1:30 molar concentration ratio.

*Triple Combination Synergistically Blocks HIV-1 Entry (1)*

Figure 7

| Percent Inhibition | Combination Index — CD4-IgG2:T-20 Mass Ratio | | | |
|---|---|---|---|---|
| | 25:1 (low) | 25:1 (high) | 5:1 | 1:1 |
| 95 | 0.32 | 0.20 | 0.22 | 0.50 |
| 90 | 0.38 | 0.25 | 0.27 | 0.55 |
| 85 | 0.43 | 0.29 | 0.30 | 0.59 |
| 80 | 0.47 | 0.33 | 0.34 | 0.62 |
| 75 | 0.51 | 0.36 | 0.37 | 0.65 |
| 70 | 0.54 | 0.39 | 0.40 | 0.67 |
| 65 | 0.58 | 0.42 | 0.43 | 0.70 |
| 60 | 0.61 | 0.45 | 0.45 | 0.73 |
| 55 | 0.65 | 0.48 | 0.49 | 0.75 |
| 50 | 0.69 | 0.51 | 0.52 | 0.78 |

Figure 8

| Percent Inhibition | T-20 Concentration, µg/ml | | T-20 Dose Reduction | CD4-IgG2 Concentration, µg/ml | | CD4-IgG2 Dose Reduction |
|---|---|---|---|---|---|---|
| | Alone | Combination | | Alone | Combination | |
| 99 | 1.1 | 0.17 | 6.6 | 130 | 4.3 | 29 |
| 95 | 0.21 | 0.044 | 4.9 | 19 | 1.10 | 17 |
| 90 | 0.10 | 0.024 | 4.2 | 7.8 | 0.59 | 13 |
| 70 | 0.025 | 0.0076 | 3.3 | 1.6 | 0.19 | 8.4 |
| 50 | 0.011 | 0.0039 | 2.8 | 0.60 | 0.095 | 6.3 |

Figure 9

| Assay (virus) | PRO 542:T-20 Molar Ratio | Percent Inhibition | Combination Index | PRO 542 Concentration, nM Alone | PRO 542 Concentration, nM Mix | Dose Reduction | T-20 Concentration, nM Alone | T-20 Concentration, nM Mix | Dose Reduction |
|---|---|---|---|---|---|---|---|---|---|
| Virus-cell fusion (JR-FL) | 1:2 | 95 | 0.14 | 30 | 2.8 | 11 | 120 | 5.1 | 24 |
| | | 90 | 0.18 | 12 | 1.5 | 8.0 | 45 | 2.6 | 17 |
| | | 70 | 0.29 | 2.5 | 0.44 | 5.7 | 8.0 | 0.78 | 10 |
| | | 50 | 0.39 | 0.92 | 0.21 | 4.4 | 2.7 | 0.37 | 7.3 |
| Virus-cell fusion (DH'23) | 1:2 | 95 | 0.36 | 65 | 11 | 5.9 | 123 | 20 | 6.2 |
| | | 90 | 0.45 | 20 | 5.0 | 4.0 | 54 | 8.9 | 6.1 |
| | | 70 | 0.76 | 2.4 | 1.2 | 2.0 | 12 | 2.1 | 5.7 |
| | | 50 | 1.1 | 0.64 | 0.49 | 1.3 | 4.8 | 0.87 | 5.5 |
| Cell-cell fusion (JR-FL) | 1:2 | 95 | 0.36 | 35 | 6.3 | 5.6 | 73 | 11 | 6.6 |
| | | 90 | 0.43 | 14 | 3.2 | 4.4 | 34 | 5.8 | 5.9 |
| | | 70 | 0.61 | 2.9 | 0.94 | 3.1 | 8.5 | 1.7 | 5.0 |
| | | 50 | 0.76 | 1.0 | 0.43 | 2.3 | 3.6 | 0.78 | 4.6 |
| Cell-cell fusion (JR-FL) | 1:10 | 95 | 0.27 | 28 | 1.4 | 20 | 58 | 12 | 4.8 |
| | | 90 | 0.28 | 11 | 0.55 | 20 | 22 | 4.9 | 4.5 |
| | | 70 | 0.31 | 2.3 | 0.11 | 21 | 3.8 | 0.97 | 3.9 |
| | | 50 | 0.34 | 0.84 | 0.039 | 17 | 1.3 | 0.35 | 3.7 |
| Cell-cell fusion (JR-FL) | 1:50 | 95 | 0.33 | 47 | 0.84 | 56 | 120 | 37 | 3.2 |
| | | 90 | 0.34 | 15 | 0.30 | 50 | 42 | 13 | 3.2 |
| | | 70 | 0.36 | 1.8 | 0.045 | 40 | 6.1 | 2.0 | 3.0 |
| | | 50 | 0.38 | 0.49 | 0.014 | 35 | 1.8 | 0.61 | 3.0 |

*HIV-1 Entry Involves at Least Three Steps that Provide Promising Targets for Therapy*

*PRO 542 (CD4-IgG2)*
*attachment inhibitor*

*PRO 140*
*coreceptor inhibitor*

T-20 fusion inhibitor

Synergistic Inhibition of Virus-Cell Fusion with PRO 542 and T-20 (I)

Figure 17

Synergistic Inhibition of HIV-1 Virus-Cell-Fusion with PRO 542 and T-20 (II)

| | Percent Inhibition | Combination Index | Inhibitory Conc., nM | | Dose Reduction | |
|---|---|---|---|---|---|---|
| | | | PRO 542 | T-20 | PRO 542 | T-20 |
| JR-FL (R5) | 95 | 0.14 | 30 | 120 | 11 | 24 |
| | 90 | 0.18 | 12 | 45 | 8.0 | 17 |
| | 70 | 0.29 | 2.5 | 8.0 | 5.7 | 10 |
| | 50 | 0.39 | 0.92 | 2.7 | 4.4 | 7.3 |
| DH123 (R5X4) | 95 | 0.36 | 65 | 123 | 5.9 | 6.2 |
| | 90 | 0.45 | 20 | 54 | 4.0 | 6.1 |
| | 70 | 0.76 | 2.4 | 12 | 2.0 | 5.7 |
| | 50 | 1.1 | 0.64 | 4.8 | 1.3 | 5.5 |

PRO 542 and T-20 were used in a 1:2 molar ratio

HIV-1 Cell-Cell Fusion Assay

Figure 20

Synergistic Inhibition of HIV-1 Cell-Cell Fusion with PRO 542 and T-20 (II)

| Conc. Ratio | Percent Inhibition | Combination Index | Inhibitory Conc, nM | | Dose Reduction (fold) | |
|---|---|---|---|---|---|---|
| | | | PRO 542 | T-20 | PRO 542 | T-20 |
| 1:2 | 95 | 0.32 | 95 | 47 | 17 | 4.9 |
| | 90 | 0.38 | 39 | 22 | 13 | 4.2 |
| | 50 | 0.69 | 3.0 | 2.5 | 6.2 | 2.8 |
| 1:10 | 95 | 0.27 | 28 | 58 | 20 | 4.8 |
| | 90 | 0.28 | 11 | 22 | 20 | 4.5 |
| | 50 | 0.34 | 0.84 | 1.3 | 22 | 3.7 |
| 1:50 | 95 | 0.33 | 47 | 120 | 56 | 3.2 |
| | 90 | 0.34 | 15 | 42 | 50 | 3.2 |
| | 50 | 0.38 | 0.49 | 1.8 | 35 | 3.0 |

Virus: HIV-1$_{JR-FL}$

PRO 140, PRO 542 and T-20 Triple Combination Synergistically Blocks HIV-1 Entry (I)

Figure 22

PRO 140, PRO 542, T-20 Triple Combination Synergistically Blocks HIV-1 Entry (II)

| Percent Inhibition | Combination Index | Inhibitory Conc, nM | | | Dose Reduction (fold) | | |
|---|---|---|---|---|---|---|---|
| | | PRO 140 | PRO 542 | T-20 | PRO 140 | PRO 542 | T-20 |
| 95 | 0.24 | 24 | 61 | 160 | 17 | 12 | 7.1 |
| 90 | 0.22 | 23 | 32 | 96 | 21 | 8.4 | 7.4 |
| 70 | 0.19 | 20 | 9.8 | 40 | 32 | 4.5 | 8.9 |
| 50 | 0.18 | 18 | 4.7 | 23 | 41 | 3.0 | 10 |

Inhibition of HIV-1$_{JR-FL}$ mediated cell-cell fusion with PRO 140, PRO 542 and T-20 used in a 1:3:30 molar ratio.

PRO 542 Does Not Potentiate T-20 Activity in the Absence of Coreceptor

Formation of the Prehairpin Intermediate Requires CD4, Coreceptor and 37 °C (I)

Formation of the Prehairpin Intermediate Requires CD4, Coreceptor and 37 °C (II)

*Possible Mechanism of Synergy: PRO 542 Increases the Half-Life of the T-20 Targ

Figure 29

| Fraction Inhibited | Dose PRO 542, nM (alone) | Dose PRO 542, nM (comb) | Dose T-1249, nM (alone) | Dose T-1249, nM (comb) | Combination Index | Dose Reduction PRO 542 | Dose Reduction T-1249 |
|---|---|---|---|---|---|---|---|
| 0.95 | 87.90 | 13.58 | 37.83 | 1.36 | 0.20 | 6.47 | 27.86 |
| 0.90 | 48.69 | 9.52 | 27.11 | 0.95 | 0.24 | 5.12 | 28.48 |
| 0.85 | 33.78 | 7.64 | 22.06 | 0.76 | 0.27 | 4.42 | 28.87 |
| 0.80 | 25.65 | 6.47 | 18.88 | 0.65 | 0.30 | 3.96 | 29.17 |
| 0.75 | 20.43 | 5.65 | 16.61 | 0.56 | 0.32 | 3.62 | 29.42 |
| 0.70 | 16.75 | 5.01 | 14.85 | 0.50 | 0.34 | 3.34 | 29.64 |
| 0.65 | 13.99 | 4.50 | 13.41 | 0.45 | 0.37 | 3.11 | 29.84 |
| 0.60 | 11.81 | 4.06 | 12.20 | 0.41 | 0.39 | 2.91 | 30.03 |
| 0.55 | 10.05 | 3.68 | 11.13 | 0.37 | 0.41 | 2.73 | 30.21 |
| 0.50 | 8.57 | 3.35 | 10.18 | 0.33 | 0.44 | 2.56 | 30.39 |

SEQUENCE LISTING

<160> NUMBER OF SEQ ID NOS: 6

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence: T20 Peptide

<400> SEQUENCE: 1

Tyr Thr Ser Leu Ile His Ser Leu Ile Glu Glu Ser Gln Asn Gln Gln
1               5                   10                  15

Glu Lys Asn Glu Gln Gln Leu Leu Glu Leu Asp Lys Trp Ala Ser Leu
            20                  25                  30

Trp Asn Trp Phe
        35

<210> SEQ ID NO 2
<211> LENGTH: 38
<212> TYPE: PRT
<213> ORGANISM: Artificial Sequence
<220> FEATURE:
<223> OTHER INFORMATION: Description of Artificial Sequence: DP107 Peptide

<400> SEQUENCE: 2

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asn Gln
        35

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: N34 Peptide

<400> SEQUENCE: 3

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: C28 Peptide

<400> SEQUENCE: 4

Trp Met Glu Trp Asp Arg Glu Ile Asn Asn Tyr Thr Ser Leu Ile His

```
                1               5              10              15
Ser Leu Ile Glu Glu Ser Gln Asn Gln Gln Glu Lys
                20              25

<210> SEQ ID NO 5
<211> LENGTH: 68
<212> TYPE: PRT
<213> ORGANISM: Artificial Sequence
<220> FEATURE:
<223> OTHER INFORMATION: Description of Artificial Sequence: N34(L6)C28
      Peptide

<400> SEQUENCE: 5

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Ser Gly Gly Arg Gly Gly Trp Met Glu Trp Asp Arg Glu Ile
            35                  40                  45

Asn Asn Tyr Thr Ser Leu Ile His Ser Leu Ile Glu Glu Ser Gln Asn
        50                  55                  60

Gln Gln Glu Leu
65

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: T-1249
      Peptide

<400> SEQUENCE: 6

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
                20                  25                  30

Ala Ser Leu Trp Glu Trp Phe
            35
```

US 7,736,649 B2

METHODS OF INHIBITING HUMAN IMMUNODEFICIENCY VIRUS INFECTION THROUGH THE ADMINISTRATION OF SYNERGISTIC COMBINATIONS OF ANTI-CCR5 MONOCLONAL ANTIBODIES, FUSION INHIBITORS, AND CD4-GP120 BINDING INHIBITORS

This application is a continuation of U.S. Ser. No. 09/912,824, filed Jul. 25, 2001, now U.S. Pat. No. 7,138,119, issued Nov. 21, 2006, which is a continuation-in-part of and claims the benefit of PCT International Application No. PCT/US01/02633, filed Jan. 26, 2001, U.S. Provisional Application No. 60/266,738, filed Feb. 6, 2001, and U.S. Ser. No. 09/663,219, filed Sep. 15, 2000 now abandoned, the contents of which are hereby incorporated by reference into this application.

Throughout this application, various publications are referenced within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

Infection of cells by human immunodeficiency virus type 1 (HIV-1) is mediated by the viral envelope (env) glycoproteins gp120 and gp41, which are expressed as a noncovalent, oligomeric complex on the surface of virus and virally infected cells. HIV-1 entry into target cells proceeds at the cell surface through a cascade of events that include (1) binding of the viral surface glycoprotein gp120 to cell surface CD4, which is the primary receptor for HIV-1, (2) env binding to fusion coreceptors such as CCR5 and CXCR4, and (3) multiple conformational changes in gp41. During fusion, gp41 adopts transient conformations that include a prehairpin fusion intermediate that ultimately folds into a conformation capable of mediating fusion. These events culminate in fusion of the viral and cellular membranes and the subsequent introduction of the viral genome into the target cell. A similar sequence of molecular events is required for infection to spread via fusion of infected and uninfected cells. Each stage of the viral entry process can be targeted for therapeutic intervention.

HIV-1 attachment can be inhibited both by agents that bind the viral envelope glycoproteins and by agents that bind human CD4. Notably, HIV-1 attachment can be inhibited by compounds that incorporate the gp120-binding domains of human CD4 and molecular mimics thereof [1-7]. Because this interaction between gp120 and CD4 is essential for virus infection, CD4-based molecules have the potential to target most if not all strains of HIV-1. In addition, viruses have limited ability to develop resistance to such molecules.

The determinants for gp120 binding map to the first extracellular domain (D1) on CD4 [1], and the amino acids critical for binding center on a loop comprising amino acids 36-47. Potent HIV-1 inhibitory activity has been reproduced in a 27-amino acid peptide that mimics this loop and surrounding structures [7].

A number of recombinant CD4-based molecules have been developed and tested for clinical activity in man. The first of these contained the four extracellular domains (D1-D4) of CD4 but lacked the transmembrane and intracellular regions. This molecule, termed soluble CD4 (sCD4), demonstrated excellent tolerability when administered to humans at doses ranging to 10 mg/kg [8,9]. Transient reductions in plasma levels of infectious HIV-1 were observed in certain patients treated with sCD4. The short half-life of sCD4 in humans (45 minutes following intravenous administration) was identified as one obstacle to using this agent for chronic therapy.

Second-generation CD4-based proteins were developed with increased serum half-life. These CD4-immunoglobulin fusion proteins comprised the D1D2 domains of CD4 genetically fused to the hinge CH2 and CH3 regions of human IgG molecules. These divalent proteins derive HIV-1 neutralizing capacity from their CD4 domains and Fc effector functions from the IgG molecule. A CD4-IgG1 fusion protein was shown to have excellent tolerability and improved pharmacokinetics in Phase I clinical testing [10]. The antiviral evaluations were inconclusive.

More recently, a third-generation tetravalent CD4-IgG2 fusion protein was developed that comprises the D1D2 domains of CD4 genetically fused to the heavy and light chain constant regions of human IgG2. This agent binds the HIV-1 envelope glycoprotein gp120 with nanomolar affinity [5] and may inhibit virus attachment both by receptor blockade and by detaching gp120 from the virion surface, thereby irreversibly inactivating the virus. In standard PBMC-based neutralization assays, CD4-IgG2 neutralized primary HIV-1 isolates derived from all major subtypes and outlier groups. The CD4-IgG2 concentrations required to achieve a 90% reduction in viral infectivity, the in vitro IC90, were approximately 15-20 µg/ml [11], concentrations that are readily achievable in vivo. CD4-IgG2 was similarly effective in neutralizing HIV-1 obtained directly from the plasma of seropositive donors in an ex vivo assay, indicating that this agent is active against the diverse viral quasispecies that are encountered clinically [12]. CD4-IgG2 also provided protection against infection by primary isolates in the hu-PBL-SCID mouse model of HIV-1 infection [13]. Recent analyses have demonstrated that CD4-IgG2's ability to neutralize primary viruses is independent of their coreceptor usage [14].

Compared with mono- or divalent CD4-based proteins, CD4-IgG2 has consistently demonstrated as much as 100-fold greater potency at inhibiting primary HIV-1 isolates [5,12,14,15]. The heightened potency may derive from CD4-IgG2's ability to bind virions with increased valency/avidity and its steric juxtaposition of two gp120 binding sites on each Fab-like arm of the immunoglobulin molecule. The larger Fab-like arms of CD4-IgG2 are also more likely to span HIV-1 envelope spikes on the virion. In a variety of preclinical models, CD4-IgG2's anti-HIV-1 activity has been shown to compare favorably with those of the rare human monoclonal antibodies that broadly and potently neutralize primary HIV-1 isolates [5,11,14,15]. In addition, CD4-IgG2 therapy is in principle less susceptible to the development of drug-resistant viruses than therapies employing anti-env monoclonal antibodies or portions of the highly mutable HIV-1 envelope glycoproteins. These properties suggest that CD4-IgG2 may have clinical utility as an agent that neutralizes cell-free virus before it has the opportunity to establish new rounds of infection. In addition to treatment, CD4-IgG2 may have utility in preventing infection resulting from occupational, perinatal or other exposure to HIV-1.

In Phase I clinical testing, single-dose CD4-IgG2 demonstrated excellent pharmacology and tolerability. In addition, measurable antiviral activity was observed by each of two measures. First, a statistically significant acute reduction in plasma HIV RNA was observed following administration of a single 10 mg/kg dose. In addition, sustained reductions in plasma levels of infectious HIV were observed in each of two patients tested. Taken together, these observations indicate that CD4-IgG2 possesses antiviral activity in humans [16].

In addition to CD4-based proteins and molecular mimics thereof, HIV-1 attachment can also be inhibited by antibodies and nonpeptidyl molecules. Known inhibitors include (1) anti-env antibodies such as IgG1b12 and F105 [17,18], (2) anti-CD4 antibodies such as OKT4A, Leu 3a, and humanized versions thereof [19,20], and (3) nonpeptidyl agents that target either gp120 or CD4 [21], [22-24]. The latter group of compounds includes aurintricarboxylic acids, polyhydroxycarboxylates, sulfonic acid polymers, and dextran sulfates.

Several agents have been identified that block HIV-1 infection by targeting gp41 fusion intermediates. These inhibitors may interact with the fusion intermediates and prevent them from folding into final fusogenic conformations. The first such agents to be identified comprised synthetic or recombinant peptides corresponding to portions of the gp41 ectodomain predicted to form hydrophobic alpha helices. One such region is present in both the amino and carboxy segments of the extracellular portion of gp41, and recent crystallographic evidence suggests that these regions interact in the presumed fusogenic conformation of gp41 [25,26]. HIV-1 infection can be inhibited by agents that bind to either N- or C-terminal gp41 epitopes that are exposed during fusion. These agents include the gp41-based peptides T-20 (formerly known as DP178), T-1249, DP107, N34, C28, and various fusion proteins and analogues thereof [27-33]. Other studies have identified inhibitors that comprise non-natural D-peptides and nonpeptidyl moieties [34,35]. Clinical proof-of-concept for this class of inhibitors has been provided by T-20, which reduced plasma HIV RNA levels by as much as 2 logs in Phase I/II human clinical testing [36]. The broad antiviral activity demonstrated for this class of inhibitors reflects the high degree of gp41 sequence conservation amongst diverse strains of HIV-1.

Recent studies [37] have demonstrated the possibility of raising antibodies against HIV-1 fusion intermediates. This work employed "fusion-competent" HIV vaccine immunogens that capture transient fusion intermediates formed upon interaction of gp120/gp41 with CD4 and fusion coreceptors. The immunogens used in these studies were formalin-fixed cocultures of cells that express HIV-1 gp120/gp41 and cells that express human CD4 and CCR5 but not CXCR4. The antibodies elicited by the vaccines demonstrated unprecedented breadth and potency in inhibiting primary HIV-1 isolates regardless of their coreceptor usage, indicating that the antibodies were raised against structures such as gp41 fusion intermediates that are highly conserved and transiently exposed during HIV-1 entry. This class of antibodies does not include the anti-gp41 monoclonal antibody known as 2F5, which interacts with an epitope that is constitutively presented on virus particles prior to fusion [38].

Previously, synergistic inhibition of HIV-1 entry has been demonstrated using certain anti-env antibodies used in combination with other anti-env antibodies [39-44], anti-CD4 antibodies [45], or CD4-based proteins [6]. Similarly, synergies have been observed using anti-CCR5 antibodies used in combination with other anti-CCR5 antibodies, CC-chemokines, or CD4-based proteins [46]. Our prior studies described in U.S. Ser. No. 09/493,346 examined combinations of fusion inhibitors and attachment inhibitors. Our prior studies described in PCT International Application No. PCT/US99/30345, WO 00/35409, published Jun. 22, 2000 examined combinations of HIV-1 attachment inhibitors and CCR5 coreceptor inhibitors. However, no prior studies have examined the combination of fusion inhibitors and CCR5 coreceptor inhibitors, nor the triple combination of fusion inhibitors, CCR5 coreceptor inhibitors and HIV-1 attachment inhibitors.

SUMMARY OF THE INVENTION

This invention provides a composition which comprises an admixture of two compounds, wherein: (a) one compound is an antibody or portion thereof which binds to a CCR5 receptor; and (b) one compound retards gp41 from adopting a conformation capable of mediating fusion of HIV-1 to a CD4+ cell by binding noncovalently to an epitope on a gp41 fusion intermediate; wherein the relative mass ratio of the compounds in the admixture ranges from about 100:1 to about 1:100, the composition being effective to inhibit HIV-1 infection of the CD4+ cell.

This invention provides a composition which comprises an admixture of three compounds, wherein: (a) one compound is an antibody or portion thereof which binds to a CCR5 receptor; (b) one compound retards attachment of HIV-1 to a CD4+ cell by retarding binding of HIV-1 gp120 envelope glycoprotein to CD4 on the surface of the CD4+ cell; and (c) one compound retards gp41 from adopting a conformation capable of mediating fusion of HIV-1 to a CD4+ cell by binding noncovalently to an epitope on a gp41 fusion intermediate; wherein the relative mass ratio of any two of the compounds in the admixture ranges from about 100:1 to about 1:100, the composition being effective to inhibit HIV-1 infection of the CD4+ cell.

This invention provides a method of inhibiting HIV-1 infection of a CD4+ cell which comprises contacting the CD4+ cell with an amount of the composition of the subject invention effective to inhibit HIV-1 infection of the CD4+ cell so as to thereby inhibit HIV-1 infection of the CD4+ cell.

This invention provides a method of inhibiting HIV-1 infection of a CD4+ cell which comprises contacting the CD4+ cell with (1) an amount of an antibody which binds to a CCR5 receptor and (2) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

This invention provides a method of inhibiting HIV-1 infection of a CD4+ cell which comprises contacting the CD4+ cell with (1) an amount of an antibody which binds to a CCR5 receptor, (2) an amount of a compound which retards attachment of HIV-1 to the CD4+ cell by retarding binding of HIV-1 gp120 envelope glycoprotein to CD4 on the surface of the CD4+ cell effective to inhibit HIV-1 infection of the CD4+ cell, and (3) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

Figure 1:
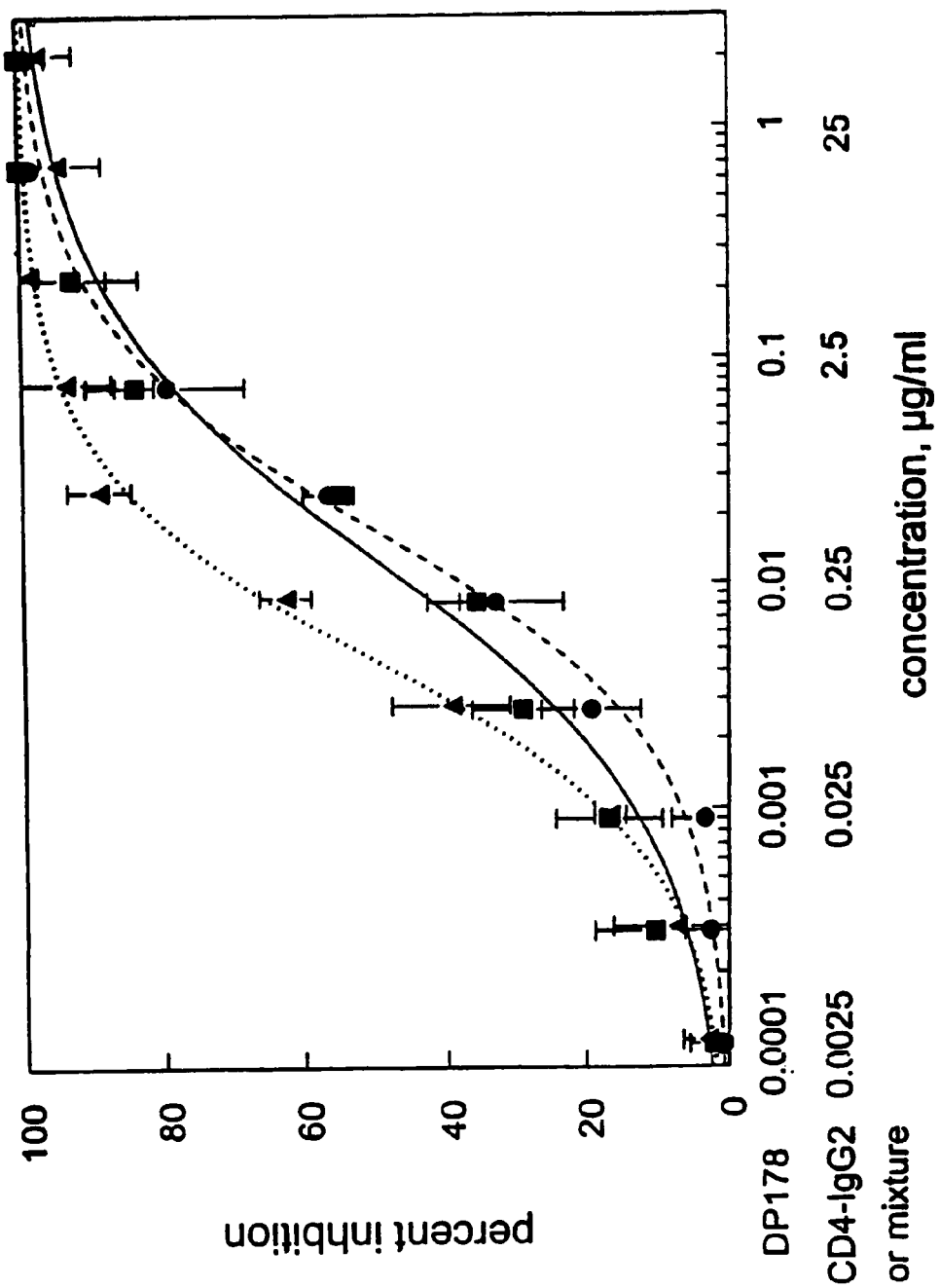
FIG. 1
Figure 5:
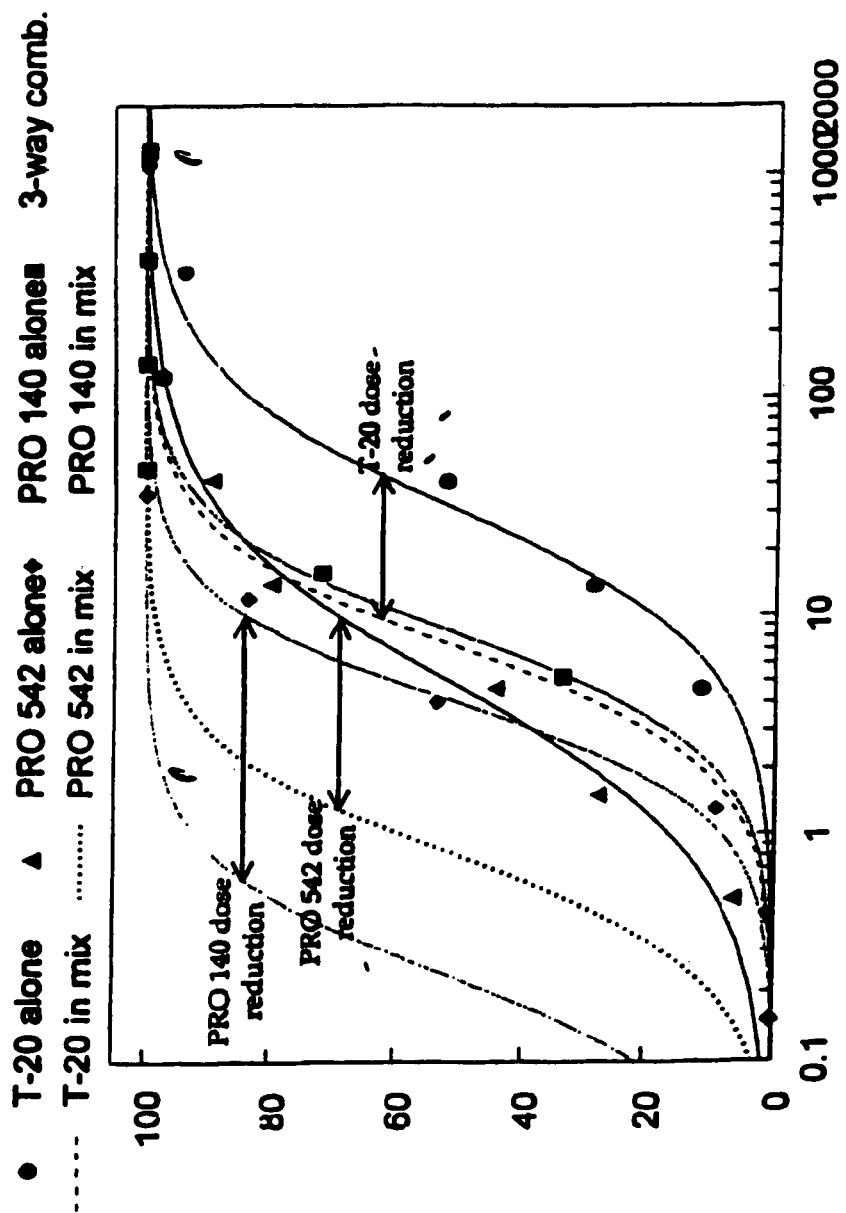

Synergistic inhibition of HIV-1 entry CD4-IgG2 (--■--), T-20 (--●--), and a 25:1 CD4-IgG2:T-20 combination (•••▲•••) were analyzed for inhibition of HIV-1 entry in an env-mediated membrane fusion (RET) assay. Inhibitors were added to a mix of HeLa-Env$_{JR-FL}^+$ and PM1 cells previously labeled with F18 and R18 respectively. Fluorescence RET was measured after 4 h of incubation, and percent inhibition was calculated as described [19]. Results are mean values from three independent experiments. The data were analyzed according to the median effect principle described in Equation (1). The best-fit parameters for K and m are 0.31 μg/ml and 0.73 for CD4-IgG2, 0.017 μg/ml and 0.92 for T-20, and 0.11 μg/ml and 1.0 for their combination. These curves are plotted and indicate a reasonable goodness-of-fit between experiment and theory ($r^2$=0.983, 0.998, and 0.996 for CD4-IgG2, T-20, and their combination, respectively). To normalize for the differences in potencies of the compounds, separate concentrations scales are used for CD4-IgG2 and the 25:1 CD4-IgG2:T-20 mixture and for T-20, as indicated.

FIG. 2

Combination indices for inhibition of HIV-1 entry by combinations of CD4-IgG2 and T-20. CD4-IgG2, T-20 and fixed mass ratios thereof were analyzed in the RET assay for the ability to inhibit env-mediated membrane fusion. The 25:1 (high) combination examined 10 three-fold serial dilutions of 250 μg/ml CD4-IgG2, 10 μg/ml T-20 and their combination. The 25:1 (low) combination examined 10 three-fold serial dilutions of 50 μg/ml CD4-IgG2, 2 μg/ml T-20 and their combination. The 5:1 combination examined 10 three-fold serial dilutions of 50 μg/ml CD4-IgG2, 2 μg/ml T-20, and their combination. The 1:1 combination examined 10 three-fold serial dilutions of 10 μg/ml CD4-IgG2, 10 μg/ml T-20 and their combination. Inhibition data from three or more independent assays were averaged prior to analysis. Dose-response curves for the various inhibitors and combinations were fit to Equation (1), which was then rearranged to calculate the inhibitor concentrations required to effect a given percent inhibition. The concentrations of the individual agents in an inhibitory mixture were calculated from their known mass ratios. These values were then used to calculate the Combination Index (CI) according to Equation (2). CI<1 indicates synergy, CI=1 indicates additive effects, and CI>1 indicates antagonism.

FIG. 3

Dose reductions observed for synergistic combinations of CD4-IgG2 and T-20. CD4-IgG2, T-20 and a 25:1 fixed mass ratio thereof were tested in the RET assay for the ability to inhibit env-mediated membrane fusion. Inhibition data from six independent assays were averaged. K and m were determined by curve-fitting the dose-response curves, and Equation (1) was rearranged to allow calculation of c for a given f for the single agents and their combination. Dose Reduction is the ratio of the inhibitor concentrations required to achieve a given degree of inhibition when the inhibitor is used alone v. in a synergistic combination.

FIG. 4

Dose reductions observed for combinations of CD4-IgG2, PRO 140, PA12 and T-20. The agents were tested individually and in combination for the ability to inhibit HIV env-mediated membrane fusion in the RET assay. a.) CD4-IgG2, PA12, T-20 and a ~1:1:10 fixed molar ratio thereof. b.) CD4-IgG2, PRO 140, T-20 and a ~2:1:20 fixed molar ratio thereof, c.) CD4-IgG2, PRO 140, T-20 and a ~4:1:30 fixed molar ratio thereof, and d.) PRO 140, T-20 and a 1:30 fixed molar ratio thereof where Dose Reduction is the ratio of the inhibitor concentrations required to achieve a given degree of inhibition when the inhibitor is used alone v. in a synergistic combination. 6-8 three-fold serial dilutions of a.) 125 nM CD4-IgG2, 167 nM PA12, 1100 nM T-20 and their combination, b.) 125 nM CD4-IgG2, 67 nM PRO 140, 1100 nM T-20 and their combination, c.) 125 nM CD4-IgG2, 33 nM PRO 140, 1100 nM T-20 and their combination, and d.) 36 nM PRO 140, 1100 nM T-20 and their combination were examined. The inhibitor concentrations required to effect a given percent inhibition were calculated. The concentrations of the individual agents in an inhibitory mixture were calculated from their known molar ratios. These values were then used to calculate the Combination Index (CI) according to Equation (2). CI<1 indicates synergy, CI=1 indicates additive effects, and CI>1 indicates antagonism.

FIG. 5:

Triple combination of PRO 542, PRO 140 and T-20 Synergistically Blocks HIV-1 Entry. PRO 542, PRO 140 and T-20 were used alone and in ~3:1:30 molar combination to inhibit HIV-1$_{JR-FL}$ env-mediated cell-cell fusion. The methodology for this assay is described in Litwin et al. (67).

FIG. 6

Synergistic inhibition of HIV-1 entry CD4-IgG2 (--■--), T-20 (--●--), and a 25:1 CD4-IgG2:T-20 combination (•••▲•••) were analyzed for inhibition of HIV-1 entry in an env-mediated membrane fusion (RET) assay. Inhibitors were added to a mix of HeLa-Env$_{JR-FL}{}^+$ and PM1 cells previously labeled with F18 and R18 respectively. Fluorescence RET was measured after 4 h of incubation, and percent inhibition was calculated as described [19]. Results are mean values from three independent experiments. The data were analyzed according to the median effect principle described in Equation (1). The best-fit parameters for K and m are 0.31 μg/ml and 0.73 for CD4-IgG2, 0.017 μg/ml and 0.92 for T-20, and 0.11 μg/ml and 1.0 for their combination. These curves are plotted and indicate a reasonable goodness-of-fit between experiment and theory ($r^2$=0.983, 0.998, and 0.996 for CD4-IgG2, T-20, and their combination, respectively). To normalize for the differences in potencies of the compounds, separate concentrations scales are used for CD4-IgG2 and the 25:1 CD4-IgG2:T-20 mixture and for T-20, as indicated.

FIG. 7

Combination indices for inhibition of HIV-1 entry by combinations of CD4-IgG2 and T-20. CD4-IgG2, T-20 and fixed mass ratios thereof were analyzed in the RET assay for the ability to inhibit env-mediated membrane fusion. The 25:1 (high) combination examined 10 three-fold serial dilutions of 250 μg/ml CD4-IgG2, 10 μg/ml T-20 and their combination. The 25:1 (low) combination examined 10 three-fold serial dilutions of 50 μg/ml CD4-IgG2, 2 μg/ml T-20 and their combination. The 5:1 combination examined 10 three-fold serial dilutions of 50 μg/ml CD4-IgG2, 2 μg/ml T-20, and their combination. The 1:1 combination examined 10 three-fold serial dilutions of 10 μg/ml CD4-IgG2, 10 μg/ml T-20 and their combination. Inhibition data from three or more independent assays were averaged prior to analysis. Dose-response curves for the various inhibitors and combinations were fit to Equation (1), which was then rearranged to calculate the inhibitor concentrations required to effect a given percent inhibition. The concentrations of the individual agents in an inhibitory mixture were calculated from their known mass ratios. These values were then used to calculate the Combination Index (CI) according to Equation (2). CI<1 indicates synergy, CI=1 indicates additive effects, and CI>1 indicates antagonism.

FIG. 8

Dose reductions observed for synergistic combinations of CD4-IgG2 and T-20. CD4-IgG2, T-20 and a 25:1 fixed mass ratio thereof were tested in the RET assay for the ability to inhibit env-mediated membrane fusion. Inhibition data from six independent assays were averaged. K and m were determined by curve-fitting the dose-response curves, and Equation (1) was rearranged to allow calculation of c for a given f for the single agents and their combination. Dose Reduction is the ratio of the inhibitor concentrations required to achieve a given degree of inhibition when the inhibitor is used alone v. in a synergistic combination.

FIG. 9

Inhibition of HIV-1$_{JR-FL}$ virus-cell fusion (A) and cell-cell fusion (B-D) with PRO 542, T-20 and combinations thereof. The PRO 542:T-20 molar ratio was 1:2 (A and C) or 1:10 (B).

The concentrations of PRO 542 and T-20 in the mixtures are plotted for the purposes of illustrating dose reductions (A and B) or lack thereof (C). In the washout assay (C), the drugs were pre-incubated with HeLa-Env cells for 2 h at 25° C. prior to washing, warming and addition of PM1 cells. In the cell-cell preincubation assay (D), HeLa-Env and PM1 cells were co-incubated for 2 h at 25° C. prior to the addition of drugs and warming to 37° C. The values represent the averages of independent assays performed in triplicate (A,B) or duplicate (C,D).

FIG. 10

Combination index values and dose reductions for inhibition if HIV-1 entry with combinations of PRO542 and T-20.

FIG. 11

HIV-1 entry involves at least three steps that provide targets for therapy: gp120-CD4 attachment; gp120-coreceptor interactions; gp41-mediated fusion.

FIG. 12

PRO 542(CD4-IgG2) attachment inhibitor.

FIG. 13

PRO 140 coreceptor inhibitor

FIG. 14

T20 fusion inhibitor

FIG. 15

HIV-1 virus cell fusion assay

FIG. 16

Synergistic Inhibition of virus-cell fusion with PRO542 and T-20. PRO542 alone (•••▲•••), T-20 alone (--●--), 1:2 mix (--■--); (------) PRO 542 in mix; (❲❘❘❘❘❳❲❘❘❘❘❳❲❘❘❘❘❳❲❘❘❘❘❳❲❘❘❘❘❳❲❘❘❘❘❳) T-20 in mix. The virus used was HIV-1JR-FL.

FIG. 17

Synergistic Inhibition of virus-cell fusion with PRO542 and T-20. PRO542 and T-20 were used in a 1:2 molar ratio

FIG. 18

HIV-1 Cell-Cell Fusion Assay. Resonance Energy Transfer (RET) assay of HIV-1 membrane fusion.

FIG. 19

Synergistic Inhibition of cell-cell fusion with PRO542 and T-20. PRO542 alone (•••▲•••), T-20 alone (--●--), 1:10 mix (--■--); (------) PRO542 in mix; (❲❘❘❘❘❳❲❘❘❘❘❳❲❘❘❘❘❳❲❘❘❘❘❳❲❘❘❘❘❳❲❘❘❘❘❳) T-20 in mix. The virus used was HIV-1JR-FL.

FIG. 20

Synergistic Inhibition of cell-cell fusion with PRO542 and T-20 in 1:2, 1:10 and 1:50 ratios.

FIG. 21

PRO140, PRO542 and T-20 Triple Combination Synergistically Blocks HIV-1 Entry. PRO140 alone (•••♦•••), PRO542 alone (•••▲•••), T-20 alone (--●--), 1:3:30 mix (--■--); (_ _ _ _ _) PRO140 in mix; (❲❘❘❘❘❳❲❘❘❘❘❳❲❘❘❘❘❳❲❘❘❘❘❳❲❘❘❘❘❳❲❘❘❘❘❳) PRO542 in mix; (--------) T-20 in mix.

FIG. 22

PRO140, PRO542 and T-20 Triple Combination Synergistically Blocks HIV-1 Entry. PRO140, PRO542 and T-20 used in a 1:3:30 molar ratio.

FIG. 23

PRO542 does not potentiate T-20 activity in the absence of coreceptor. PRO542 alone (•••▲•••), T-20 alone (--●--), PRO542:T-20 cocktail (--■--); (--------) PRO542 in cocktail.

FIG. 24

Formation of prehairpin intermediate requires CD4, coreceptor and 37° C. (--●--) T-20 standard assay; (--○--) T-20, 25° C. preincubation; (•••▲•••) PRO542 standard assay; (--△--) PRO542, 25° C. preincubation;

FIG. 25

Formation of prehairpin intermediate requires CD4, coreceptor and 37° C. (--●--) T-20 standard assay; (--○--) T-20 temperature shift washout assay.

FIG. 26

Possible mechanism of synergy: PRO542 increases the half-life of the T-20 targets.

FIG. 27

Possible mechanism of synergy: PRO542 increases the half-life of the T-20 targets.

FIG. 28

Synergistic inhibition of HIV-1 entry: PRO 542, T-1249, and a 1:10 molar combination (4:1 mass combination) of PRO 542:T-1249 were analyzed for inhibition of HIV-1 entry in an env-mediated membrane fusion (RET) assay. Inhibitors were added to a mix of HeLa-EnvJR-FL⁺ and PM1 cells previously labeled with F18 and R18 respectively. Fluorescence RET was measured after 4 hours of incubation, and percent inhibition was calculated as described in Litwin, et al. (J. Virol. 70: 6437, 1996). The concentrations of PRO 542 and T-1249 present in the cocktail are derived from the curve fit of the data and are shown for the purposes of illustrating dose reductions.

FIG. 29

Combination indices and dose reductions observed for a 1:10 molar combination of PRO 542 and T-1249. Compounds were analyzed as described in FIG. 28. Combination Index values were calculated according to the median effect principle. Dose Reduction is the ratio of the inhibitor concentrations required to achieve a given degree of inhibition when the inhibitor is used alone verses in combination.

DETAILED DESCRIPTION OF THE INVENTION

The plasmids CD4-IgG2-HC-pRcCMV and CD4-kLC-pRcCMV were deposited pursuant to, and in satisfaction of, the requirements of the Budapest Treaty on the International Recognition of the Deposit of Microorganisms (the "Budapest Treaty") for the Purposes of Patent Procedure with the American Type Culture Collection (ATCC), 10801 University Blvd, Manassas, Va. 20110-2209 under ATCC Accession Nos. 75193 and 75194, respectively. The plasmids were deposited with ATCC on Jan. 30, 1992. The plasmid designated pMA243 was similarly deposited in accordance with the Budapest Treaty with ATCC under Accession No. 75626 on Dec. 16, 1993.

The murine hybridomas PA8, PA9, PA10, PA11, PA12 and PA14 were deposited pursuant to, and in satisfaction of, the requirements of the Budapest Treaty on the International Recognition of the Deposit of Microorganisms (the "Budapest Treaty") for the Purposes of Patent Procedure with the American Type Culture Collection (ATCC), 10801 University Blvd, Manassas, Va. 20110-2209 under the following ATCC Accession Nos.: PA8 (ATCC No. HB-12605), PA9 (ATCC No. HB-12606), PA10 (ATCC No. HB-12607), PA11 (ATCC No. HB-12608), PA12 (ATCC No. HB-12609) and PA14 (ATCC No. HB-12610). The hybridomas were deposited on Dec. 2, 1998.

As used herein, the following standard abbreviations are used throughout the specification to indicate specific amino acids:

| | |
|---|---|
| A = ala = alanine | R = arg = arginine |
| N = asn = asparagine | D = asp = aspartic acid |
| C = cys = cysteine | Q = gln = glutamine |
| E = glu = glutamic acid | G = gly = glycine |
| H = his = histidine | I = ile = isoleucine |
| L = leu = leucine | K = lys = lysine |
| M = met = methionine | F = phe = phenylalanine |
| P = pro = proline | S = ser = serine |
| T = thr = threonine | W = trp = tryptophan |
| Y = tyr = tyrosine | V = val = valine |

This invention provides a composition which comprises an admixture of two compounds, wherein: (a) one compound is an antibody or portion thereof which binds to a CCR5 receptor; and (b) one compound retards gp41 from adopting a conformation capable of mediating fusion of HIV-1 to a CD4+ cell by binding noncovalently to an epitope on a gp41 fusion intermediate; wherein the relative mass ratio of the compounds in the admixture ranges from about 100:1 to about 1:100, the composition being effective to inhibit HIV-1 infection of the CD4+ cell.

This invention provides a composition which comprises an admixture of three compounds, wherein: (a) one compound is an antibody or portion thereof which binds to a CCR5 receptor; (b) one compound retards attachment of HIV-1 to a CD4+ cell by retarding binding of HIV-1 gp120 envelope glycoprotein to CD4 on the surface of the CD4+ cell; and (c) one compound retards gp41 from adopting a conformation capable of mediating fusion of HIV-1 to a CD4+ cell by binding noncovalently to an epitope on a gp41 fusion intermediate; wherein the relative mass ratio of any two of the compounds in the admixture ranges from about 100:1 to about 1:100, the composition being effective to inhibit HIV-1 infection of the CD4+ cell.

This invention provides a composition which comprises an admixture of two compounds, wherein one compound retards attachment of HIV-1 to a CD4+ cell by retarding binding of HIV-1 gp120 envelope glycoprotein to CD4 on the surface of the CD4+ cell and the other compound retards gp41 from adopting a conformation capable of mediating fusion of HIV-1 to a CD4+ cell by binding noncovalently to an epitope on a gp41 fusion intermediate, wherein the relative mass ratio of the compounds in the admixture ranges from about 100:1 to about 1:100, the composition being effective to inhibit HIV-1 infection of the CD4+ cell.

As used herein, "HIV-1" means the human immunodeficiency virus type-1. HIV-1 includes but is not limited to extracellular virus particles and the forms of HIV-1 associated with HIV-1 infected cells. HIV-$1_{JR-FL}$ is a strain that was originally isolated at autopsy from the brain tissue of an AIDS patient [47]. The virus was co-cultured with lectin-stimulated normal human peripheral blood mononuclear cells. The virus has been cloned and the DNA sequences of its envelope glycoproteins are known (Genbank Accession #U63632). In terms of sensitivity to inhibitors of viral entry, HIV-$1_{JR-FL}$ is known to be highly representative of primary HIV-1 isolates [11,14,15,48-50].

As used herein, "gp41 fusion intermediates" includes structures, conformations, and oligomeric states that are preferentially and transiently presented or exposed on the HIV-1 envelope glycoprotein gp41 during the process of HIV-1 env-mediated membrane fusion. These intermediates may form upon interaction of HIV-1 with cellular receptors or may be present in partially or fully occluded states on HIV-1 prior to its interaction with cellular receptors. "gp41 fusion intermediates" do not include fusogenic gp41 conformations that cannot provide targets for therapeutic intervention.

The gp41 fusion intermediates may contain multiple epitopes that are transiently exposed during fusion and can provide targets for therapeutic intervention. As used herein, an "N-terminal gp41 epitope" may comprise all or portions of the sequences from amino acid A541 to Q590. As used herein, a "C-terminal gp41 epitope" may comprise all or portions of the sequences from amino acid W628 to L663. These epitopes have the potential to form coiled-coils of interacting alpha helical segments by virtue of heptad (sequence of seven amino acids) repeats containing hydrophobic amino acids at positions 1 and 4 of the heptad. The amino acid numbering system is for the HxB2 isolate of HIV-1 (Genbank Protein Accession No. AAB50262). Because of the sequence variability of HIV-1 envelope proteins, the composition, size and precise location of such sequences may be different for different viral isolates. The gp41 fusion intermediates may also present other linear or conformational epitopes that are transiently expressed during HIV-1 entry. An inhibitor may target multiple epitopes present on gp41 fusion intermediates. Alternatively, separate inhibitors may be used in combination to target one or more epitopes present on gp41 fusion intermediates.

As used herein, "fusogenic" means capable of mediating membrane fusion. As used herein, "HIV-1 fusion coreceptor" means a cellular receptor that mediates fusion between the target cell expressing the receptor and HIV-1 or an HIV-1 envelope glycoprotein$^+$ cell. HIV-1 fusion co-receptors include but are not limited to CCR5, CXCR4 and other chemokine receptors. As used herein, "fusion" means the joining or union of the lipid bilayer membranes found on mammalian cells or viruses such as HIV-1. This process is distinguished from the attachment of HIV-1 to a target cell. Attachment is mediated by the binding of the HIV-1 exterior glycoprotein to the human CD4 receptor, which is not a fusion co-receptor.

As used herein, "retards" means that the amount is reduced. As used herein, "attachment" means the process that is mediated by the binding of the HIV-1 envelope glycoprotein to the human CD4 receptor, which is not a fusion co-receptor. As used herein, "CD4" means the mature, native, membrane-bound CD4 protein comprising a cytoplasmic domain, a hydrophobic transmembrane domain, and an extracellular domain which binds to the HIV-1 gp120 envelope glycoprotein.

As used herein, "epitope" means a portion of a molecule or molecules that form a surface for binding antibodies or other compounds. The epitope may comprise contiguous or non-contiguous amino acids, carbohydrate or other nonpeptidyl moities or oligomer-specific surfaces.

The compounds of the subject invention have shown to demonstrate a synergistic effect. As used herein, "synergistic" means that the combined effect of the compounds when used in combination is greater than their additive effects when used individually.

In one embodiment of the composition of this invention, the compound which retards attachment of HIV-1 to the CD4+ cell by retarding binding of HIV-1 gp120 envelope glycoprotein to CD4 on the surface of the CD4+ cell is a CD4-based protein. As used herein, "CD4-based protein" means any protein comprising at least one sequence of amino acid residues corresponding to that portion of CD4 which is required for CD4 to form a complex with the HIV-1 gp120 envelope glycoprotein.

In one embodiment the CD4-based protein is a CD4-immunoglobulin fusion protein. In one embodiment the CD4- immunoglobulin fusion protein is CD4-IgG2, wherein the CD4-IgG2 comprises two heavy chains and two lights chains, wherein the heavy chains are encoded by an expression vector designated CD4-IgG2HC-pRcCMV (ATCC Accession No. 75193) and the light chains are encoded by an expression vector designated CD4-kLC-pRcCMV (ATCC Accession No. 75194). As used herein, CD4-IgG2 is also referred to as PRO 542.

In one embodiment of the composition of this invention, the compound which retards attachment of HIV-1 to the CD4+ cell by retarding binding of HIV-1 gp120 envelope glycoprotein to CD4 on the surface of the CD4+ cell is a protein, the amino acid sequence of which comprises that of a protein found in HIV-1 as an envelope glycoprotein. In one embodiment, the protein binds to an epitope of CD4 on the surface of the CD4+ cell. In one embodiment the envelope glycoprotein is selected from the group consisting of gp120, gp160, and gp140.

In one embodiment of the composition of this invention, the compound which retards the attachment of HIV-1 to the CD4+ cell by retarding binding of HIV-1 gp120 envelope glycoprotein to CD4 on the surface of the CD4+ cell is an antibody or portion of an antibody. In one embodiment, the antibody is a monoclonal antibody. In one embodiment, the monoclonal antibody is a human, humanized or chimeric antibody. In one embodiment, the portion of the antibody is a Fab fragment of the antibody. In one embodiment, the portion of the antibody comprises the variable domain of the antibody. In one embodiment, the portion of the antibody comprises a CDR portion of the antibody. In one embodiment, the monoclonal antibody is an IgG, IgM, IgD, IgA, or IgE monoclonal antibody.

As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man. Methods for humanizing antibodies are known to those skilled in the art.

This invention provides humanized forms of the above antibodies. As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody, i.e., in the present invention, the ability to bind CCR5.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 (58) comprise the production of chimeric antibodies having a variable region of one antibody and a constant region of another antibody.

U.S. Pat. No. 5,225,539 (59) describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. No. 5,585,089 (60) and U.S. Pat. No. 5,693,761 (61) and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 (62) also propose four possible criteria which may be used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 Å of the CDRs in a three dimensional model of the antibody and is predicted to be capable of interacting with the CDRs. The above methods are merely illustrative of some of the methods that one skilled in the art could employ to make humanized antibodies.

In one embodiment, the monoclonal antibody binds to an HIV-1 envelope glycoprotein. In one embodiment, the HIV-1 envelope glycoprotein is selected from the group consisting of gp120 and gp160.

In one embodiment, the HIV-1 envelope glycoprotein is gp120 and the monoclonal antibody which binds to gp120 is IgG1b12 or F105. IgG1b12 is listed as item #2640 in the NIH AIDS Research and Reference Reagent Program Catalog.

F105 is listed as item #857 in the NIH AIDS Research and Reference Reagent Program Catalog.

In one embodiment, the antibody binds to an epitope of CD4 on the surface of the CD4+ cell.

In one embodiment of the composition of this invention, the compound which retards attachment of HIV-1 to the CD4+ cell by retarding binding of HIV-1 gp120 envelope glycoprotein to CD4 on the surface of the CD4+ cell is a peptide. In one embodiment of the composition of this invention, the compound which retards attachment of HIV-1 to the CD4+ cell by retarding binding of HIV-1 gp120 envelope glycoprotein to CD4 on the surface of the CD4+ cell is a nonpeptidyl agent. As used herein, "nonpeptidyl" means that the agent does not consist in its entirety of a linear sequence of amino acids linked by peptide bonds. A nonpeptidyl agent may, however, contain one or more peptide bonds.

In one embodiment of the composition of this invention, the compound which retards gp41 from adopting a conformation capable of mediating fusion of HIV-1 to a CD4+ cell by binding noncovalently to an epitope on a gp41 fusion intermediate is an antibody. In one embodiment the antibody is a monoclonal antibody. In one embodiment, the antibody is a polyclonal antibody.

In one embodiment of the composition of this invention, the compound which retards gp41 from adopting a conformation capable of mediating fusion of HIV-1 to a CD4+ cell by binding noncovalently to an epitope on a gp41 fusion intermediate is a peptide.

In one embodiment of the composition of this invention, the compound which retards gp41 from adopting a conformation capable of mediating fusion of HIV-1 to a CD4+ cell by binding noncovalently to an epitope on a gp41 fusion intermediate is a fusion protein which comprises a peptide which includes but is not limited to T-20 (SEQ ID NO: 1), DP107 (SEQ ID NO: 2), N34 (SEQ ID NO: 3), C28 (SEQ ID NO: 4), and N34(L6)C28 (SEQ ID NO: 5). In one embodiment the peptide is selected from the group consisting of T-20 (SEQ ID NO: 1), DP107 (SEQ ID NO: 2), N34 (SEQ ID NO: 3), C28 (SEQ ID NO: 4), N34(L6)C28 (SEQ ID NO: 5), and T-1249 (SEQ ID NO:6). In one embodiment, the peptide is T-20 (SEQ ID NO: 1).

As used herein, "T-20" and "DP178" are used interchangeably to denote a peptide having the following amino acid sequence: YTSLIHSLIEESQNQQEKNEQELLELDK-WASLWNWF (SEQ ID NO:1) and as described [29,32]. DP107 has the following amino acid sequence: NNLL-RAIEAQQHLLQLTVWGIKQLQARILAVERYLKDQ (SEQ ID NO:2). N34 has the following amino acid sequence: SGIVQQQNNLLRAIEAQQHLLQLTVWGIKQLQAR (SEQ ID NO:3). C28 has the following amino acid sequence: WMEWDREINNYTSLIHSLIEESQNQQEK (SEQ ID NO:4). N34(L6)C28 has the following amino acid sequence: SGIVQQQNNLL-RAIEAQQHLLQLTVWGIKQLQARSGGRG-GWMEWDREINNYTSLIHSL IEESQNQQEK (SEQ ID NO:5). T-1249 has the following amino acid sequence: WQEWEQKITALLEQA-QIQQEKNEYELQKLDKWASLWEWF (SEQ ID NO: 6).

In one embodiment of the compositions described herein, the peptide is a mutant peptide which (1) consists of amino acids having a sequence identical to that of a wildtype peptide selected from the group consisting of T-20 (SEQ ID NO: 1), DP-107 (SEQ ID NO: 2), N34 (SEQ ID NO: 3), C28 (SEQ ID NO: 4), N34 (L6)C28 (SEQ ID NO: 5) and T-1249 (SEQ ID NO: 6), except for an addition of at least one glycine residue to a 5' end of the peptide, to a 3' end of the peptide, or to both ends of the peptide and (2) retards gp41 from adopting a conformation capable of mediating fusion of HIV-1 to a CD4+ cell by binding noncovalently to an epitope on a gp41 fusion intermediate.

In one embodiment, the compound which retards gp41 from adopting a conformation capable of mediating fusion of HIV-1 to a CD4+ cell by binding noncovalently to an epitope on a gp41 fusion intermediate is a fusion protein which comprises a peptide selected from the group consisting of T-20 (SEQ ID NO: 1), DP107 (SEQ ID NO: 2), N34 (SEQ ID NO: 3), C28 (SEQ ID NO: 4), N34(L6)C28 (SEQ ID NO: 5), and T-1249 (SEQ ID NO:6).

In one embodiment of the compositions described herein, the peptide is selected from the group consisting of T-20 (SEQ ID NO: 1), DP107 (SEQ ID NO: 2), N34 (SEQ ID NO: 3), C28 (SEQ ID NO: 4), N34(L6)C28 (SEQ ID NO: 5), and T-1249 (SEQ ID NO:6).

In one embodiment of the compositions described herein, the peptide is T-20 (SEQ ID NO: 1). In one embodiment of the compositions described herein, the peptide is T-1249 (SEQ ID NO:6)

In one embodiment of the composition of this invention, the compound which retards gp41 from adopting a conformation capable of mediating fusion of HIV-1 to a CD4+ cell by binding noncovalently to an epitope on a gp41 fusion intermediate is a non-peptidyl agent.

In one embodiment, a non-peptidyl agent of the subject invention is a small molecule. In one embodiment, the non-peptidyl agent is a compound having a molecular weight less than 500 daltons.

In one embodiment of the composition of this invention, the antibody which binds to a CCR5 receptor includes but is not limited to PA8 (ATCC Accession No. HB-12605), PA10 (ATCC Accession No. 12607), PA11 (ATCC Accession No. HB-12608), PA12 (ATCC Accession No. HB-12609), and PA14 (ATCC Accession No. HB-12610). In one embodiment, the antibody is a monoclonal antibody. In one embodiment, the monoclonal antibody is a human, humanized or chimeric antibody. In one embodiment, the portion of the antibody is a Fab fragment of the antibody. In one embodiment, the portion of the antibody comprises the variable domain of the antibody. In one embodiment, the portion of the antibody comprises a CDR portion of the antibody. In one embodiment, the monoclonal antibody is an IgG, IgM, IgD, IgA, or IgE monoclonal antibody.

In one embodiment of the composition of this invention, the relative mass ratio of each such compound in the admixture ranges from about 25:1 to about 1:1. In one embodiment, the mass ratio is about 25:1. In one embodiment, the mass ratio is about 5:1. In one embodiment, the mass ratio is about 1:1.

In one embodiment of the composition of this invention, the composition is admixed with a carrier. The carriers of the subject invention include but are not limited to aerosol, intravenous, oral or topical carriers. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a method of inhibiting HIV-1 infection of a CD4+ cell which comprises contacting the CD4+ cell with an amount of the composition of the subject invention effective to inhibit HIV-1 infection of the CD4+ cell so as to thereby inhibit HIV-1 infection of the CD4+ cell.

In one embodiment, the CD4+ cell is present in a subject and the contacting is effected by administering the composition to the subject.

As used herein, "subject" includes any animal or artificially modified animal capable of becoming HIV-infected. Artificially modified animals include, but are not limited to, SCID mice with human immune systems. The animals include but are not limited to mice, rats, dogs, cats, guinea pigs, ferrets, rabbits, and primates. In the preferred embodiment, the subject is a human.

As used herein, "administering" may be effected or performed using any of the methods known to one skilled in the art, which includes intralesional, intraperitoneal, intramuscular, subcutaneous, intravenous, liposome mediated delivery, transmucosal, intestinal, topical, nasal, oral, anal, ocular or otic delivery. The compounds may be administered separately (e.g., by different routes of administration, sites of injection, or dosing schedules) so as to combine in synergistically effective amounts in the subject.

The dose of the composition of the invention will vary depending on the subject and upon the particular route of administration used. Dosages can range from 0.1 to 100,000 µg/kg. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

As used herein, "effective dose" means an amount in sufficient quantities to either treat the subject or prevent the subject from becoming infected with HIV-1. A person of ordinary skill in the art can perform simple titration experiments to determine what amount is required to treat the subject.

In one embodiment, the effective amount of the composition comprises from about 0.000001 mg/kg body weight to about 100 mg/kg body weight of the subject.

This invention provides a method of inhibiting HIV-1 infection of a CD4+ cell which comprises contacting the CD4+ cell with (1) an amount of an antibody which binds to a CCR5 receptor and (2) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

This invention provides a method of inhibiting HIV-1 infection of a CD4+ cell which comprises contacting the CD4+ cell with (1) an amount of an antibody which binds to a CCR5 receptor, (2) an amount of a compound which retards attachment of HIV-1 to the CD4+ cell by retarding binding of HIV-1 gp120 envelope glycoprotein to CD4 on the surface of the CD4+ cell effective to inhibit HIV-1 infection of the CD4+ cell, and (3) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

This invention provides a method of inhibiting HIV-1 infection of a CD4+ cell which comprises contacting the CD4+ cell with (1) an amount of a compound which retards attachment of HIV-1 to the CD4+ cell by retarding binding of HIV-1 gp120 envelope glycoprotein to CD4 on the surface of the CD4+ cell effective to inhibit HIV-1 infection of the CD4+ cell and (2) an amount of a compound which retards gp41 from adopting a conformation capable of mediating fusion of HIV-1 to a CD4+ cell by binding noncovalently to an epitope on a gp41 fusion intermediate so as to thereby inhibit HIV-1 infection of the CD4+ cell.

In one embodiment, the CD4+ cell is present in a subject and the contacting is effected by administering the compounds to the subject. In one embodiment, the compounds are administered to the subject simultaneously. In one embodiment, the compounds are administered to the subject at different times. In one embodiment, the compounds are administered to the subject by different routes of administration.

The subject invention has various applications which includes HIV treatment such as treating a subject who has become afflicted with HIV. As used herein, "afflicted with HIV-1" means that the subject has at least one cell which has been infected by HIV-1. As used herein, "treating" means either slowing, stopping or reversing the progression of an HIV-1 disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV-1. Another application of the subject invention is to prevent a subject from contracting HIV. As used herein, "contracting HIV-1" means becoming infected with HIV-1, whose genetic information replicates in and/or incorporates into the host cells. Another application of the subject invention is to treat a subject who has become infected with HIV-1. As used herein, "HIV-1 infection" means the introduction of HIV-1 genetic information into a target cell, such as by fusion of the target cell membrane with HIV-1 or an HIV-1 envelope glycoprotein cell. The target cell may be a bodily cell of a subject. In the preferred embodiment, the target cell is a bodily cell from a human subject. Another application of the subject invention is to inhibit HIV-1 infection. As used herein, "inhibiting HIV-1 infection" means reducing the amount of HIV-1 genetic information introduced into a target cell population as compared to the amount that would be introduced without said composition.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

First Series of Experiments

A. Materials and Methods

1) Reagents

Purified recombinant CD4-IgG2 protein was produced by Progenics Pharmaceuticals, Inc. from plasmids CD4-IgG2-HC-pRcCMV and CD4-kLC-pRcCMV (ATCC Accession Nos. 75193 and 75194, respectively) as described [5]. HeLa-env cells were prepared by transfecting HeLa cells (ATCC Catalog # CCL-2) with HIV-1 gp120/gp41 env-expressing plasmid pMA243 as described [51]. PM1 cells are available from the National Institutes of Health AIDS Reagent Program (Catalog #3038). The T-20 peptide was synthesized using standard solid-phase Fmoc chemistry and purified and characterized as described [31,32].

2) Inhibition of HIV-1 env-Mediated Membrane Fusion

HIV-1 envelope-mediated fusion between HeLa-Env$_{JR-FL}$ and PM1 cells was detected using a Resonance Energy Transfer (RET) assay. Equal numbers ($2 \times 10^4$) of fluorescein octadecyl ester (F18)-labeled envelope-expressing cells and octadecyl rhodamine (R18)-labeled PM1 cells were plated in 96-well plates in 15% fetal calf serum in phosphate buffered saline and incubated for 4 h at 37 (C in the presence of varying concentrations of CD4-IgG2, T-20 or combinations thereof. Fluorescence RET was measured with a Cytofluor platereader (PerSeptive Biosystems) and % RET was determined as previously described [19].

3) Quantitative Analysis of the Synergistic, Additive or Antagonistic Effects of Combining the Agents HIV-1 inhibition data were analyzed according to the Combination Index method of Chou and Talay [52,53]. The data are modeled according to the median-effect principle, which can be written $$f=1/[1+(K/c)^m] \qquad (1)$$

where f is the fraction affected/inhibited, c is concentration, K is the concentration of agent required to produce the median effect, and m is an empirical coefficient describing the shape of the dose-response curve. Equation (1) is a generalized form of the equations describing Michaelis-Menton enzyme kinetics, Langmuir adsorption isotherms, and Henderson-Hasselbalch ionization equilibria, for which m=1 in all cases. In the present case, K is equal to the $IC_{50}$ value. K and m are determined by curve-fitting the dose-response curves.

After the best-fit parameters for K and m are obtained for the experimental agents and their combination, Equation (1) is rearranged to allow for calculation of c for a given f. The resulting table of values (e.g., Figure X) is used to calculate the Combination Index (CI) using the equation $$CI=c_{1m}/c_1+c_{2m}/c_2+c_{1m}c_{2m}/c_1c_2 \qquad (2)$$

where $c_1$=concentration of compound 1 when used alone
$c_2$=concentration of compound 2 when used alone
$C_{1m}$=concentration of compound 1 in the mixture
$C_{2m}$=concentration of compound 2 in the mixture All concentrations are those required to achieve a given degree of inhibition. Equation (2) is used when the molecules are mutually nonexclusive, i.e., have different sites of action. Since this is the likely scenario for inhibitors of HIV-1 attachment and gp41 fusion intermediates, Equation (2) was used for all Combination Index calculations. Mutually nonexclusive calculations provide a more conservative estimate of the degree of synergy that mutually exclusive calculations, for which the $c_{1m}c_{2m}/c_1c_2$ term is dropped. CI<1 indicates synergy, CI=1 indicates purely additive effects, and CI>1 indicates antagonism. In general, CI values are most relevant at the higher levels of inhibition that are required to achieve a measurable clinical benefit.

B. Results and Discussion

Combinations of inhibitors of HIV-1 attachment and gp41 fusion intermediates were first tested for the ability to inhibit HIV-1 env-mediated membrane fusion in the RET assay. This assay has proven to be a highly successful model of the HIV-1 entry process. In this assay, env-dependent coreceptor usage patterns and cellular tropisms of the parental viruses are accurately reproduced [19]. Indeed, the assay was instrumental in demonstrating that CCR5 functions as a requisite fusion coreceptor and acts at the level of viral entry [54]. The fusion assay and infectious virus are similarly sensitive to inhibition by metal chelators and agents that target the full complement of viral and cellular receptors [19,46,55].

Dose-response curves were obtained for the agents used individually and in combination in both assays. Data were analyzed using the median effect principle [52,53]. The concentrations of single-agents or their mixtures required to produce a given effect were quantitatively compared in a term known as the Combination Index (CI). CI>1 indicates antagonism, CI=1 indicates a purely additive effect, and CI<1 indicates a synergistic effect wherein the presence of one agent enhances the effect of another.

Combinations of CD4-IgG2 and T-20 were observed to be potently synergistic in inhibiting env-mediated membrane fusion. FIG. 1 illustrates representative dose-response curves obtained in the membrane fusion assay for CD4-IgG2, T-20, and combinations of the two. The curve for the combination is highly displaced towards lower inhibitor concentrations and provides qualitative evidence that CD4-IgG2 and T-20 act in a synergistic manner.

To quantitatively calculate the degree of synergy observed between CD4-IgG2 and T-20, we analyzed the dose-response curves according to the Combination Index method [52,53]. The analysis included data obtained at 25:1, 5:1, and 1:1 CD4-IgG2:T-20 mass ratios. At the 25:1 mass ratio, both high (0-250 µg/ml CD4-IgG2 and 0-10 µg/ml T-20) and low (0-50 µg/ml CD4-IgG2 and 0-2 µg/ml T-20) concentration ranges were evaluated. As indicated in FIG. 2, potent synergies were observed over these broad ranges of inhibitor ratios and concentrations, with CI values as low as 0.20 under optimal conditions. This degree of synergy is remarkable since CI values of 0.2 are rarely observed for combinations involving anti-HIV-1 antibodies [41-44], reverse transcriptase inhibitors [56], or protease inhibitors [57]. The observed synergies indicate that HIV-1 attachment and formation of gp41 fusion intermediates are inter-dependent steps. One possibility is that attachment inhibitors, when used at suboptimal concentrations, may slow but not abrogate the binding of gp120 to CD4. In this case, gp41 fusion intermediates may be formed and persist on the virus (or infected cell) for longer periods of time at levels below that required for membrane fusion and thus provide better targets for inhibitory agents.

The observed synergies translate into significant reductions in the amounts of CD4-IgG2 and T-20 needed for inhibition. These reductions are illustrated in FIG. 3 for CD4-IgG2 and T-20 used in a 25:1 mass ratio. By way of example, inhibition of viral entry by 95% requires 0.21 µg/ml of T-20 used alone, 19 µg/ml of CD4-IgG2 used alone and 1.14 µg/ml of a combination containing 0.044 µg/ml of T-20 and 1.1 µg/ml of CD4-IgG2. The combination reduces the respective doses of T-20 and CD4-IgG2 by 5- and 17-fold, respectively. Still greater dose reductions are observed at higher levels of inhibition.

Second Series of Experiments

HIV-1 entry proceeds via a cascade of at least three sequential events: (1) the attachment of the HIV-1 surface glycoprotein gp120 to CD4, which is the primary cellular receptor for HIV-1, (2) the interaction of the gp120-CD4 complex with fusogenic coreceptors such as CCR5 and CXCR4, and (3) membrane fusion mediated by the HIV-1 transmembrane glycoprotein gp41. PRO 542 (CD4-IgG2) is an antibody-like molecule that binds to gp120 and thereby inhibits attachment of the virus to host cells via CD4. PRO 140 (PA14) and PA12 are monoclonal antibodies to CCR5 that block its function as an HIV-1 coreceptor. Lastly, T-20 is a 36-mer peptide derived from the highly conserved C-terminal ectodomain of gp41. T-20 blocks gp41-mediated membrane fusion events. PRO 542 is thus an attachment inhibitor that blocks the first step of HIV-1 entry; PRO 140 and PA12 are both CCR5 coreceptor inhibitors that block the second step; and T-20 is a fusion inhibitor that blocks the third step. Attachment, coreceptor and fusion inhibitors are all members of a broad category of antiviral agents collectively know as HIV-1 entry inhibitors. CCR5 coreceptor inhibitors and CXCR4 coreceptor inhibitors constitute two distinct subclasses of coreceptor inhibitors.

When used individually, each of these compounds inhibit HIV-1 infection in vitro. PRO 542 and T-20 have also both demonstrated significant antiviral activity when used individually in human clinical trials, providing clinical proof-of-concept for inhibitors of HIV-1 entry (1,2).

The multi-step, inter-dependent nature of HIV-1 entry suggests that combinations of entry inhibitors may act in a non-additive or cooperative manner that either enhances (synergizes) or diminishes (antagonizes) the antiviral effect. Significant synergies have been observed for certain 2-way combinations of entry inhibitors, including attachment inhibitors used with CCR5 coreceptor inhibitors, attachment inhibitors used with fusion inhibitors, CCR5 coreceptor inhibitors used with other CCR5 coreceptor inhibitors, and CXCR4 coreceptor inhibitors used with fusion inhibitors (3,4).

However, whereas synergies are observed with certain members of a given class of inhibitor, purely additive or even antagonistic effects are seen when other members of the same class are used (3), highlighting the complexity of the HIV-1 entry process and the difficulty of predicting synergistic combinations. No prior study has examined either 2-way combinations of CCR5 coreceptor inhibitors and fusion inhibitors or triple or higher combinations that include members of all three classes of HIV-1 entry inhibitors. We have discovered that synergistic inhibition of HIV-1 can be obtained using the CCR5 coreceptor inhibitor PRO 140 in combination with the fusion inhibitor T-20. See FIG. 4D. In addition, remarkable synergies are observed using a triple combination containing an attachment inhibitor (PRO 542), a CCR5 coreceptor inhibitor (either PRO 140 or PA12) and a fusion inhibitor (T-20). See FIGS. 4A-C and FIG. 5. The synergies observed with the triple combination are surprisingly potent and translate into dose reductions ranging to 260-fold.

REFERENCES FOR FIRST SERIES OF EXPERIMENTS

1. Arthos J, Deen K C, Chaikin M A et al. Identification of the residues in human CD4 critical for the binding of HIV. Cell 1989; 57:469-481.
2. Clapham P R., Weber J N., Whitby D. et al. Soluble CD4 blocks the infectivity of diverse strains of HIV and SIV for T cells and monocytes but not for brain and muscle cells. Nature 1989; 337:368-370.
3. Deen K C., McDougal JS., Inacker R. et al. A soluble form of CD4 (T4) protein inhibits AIDS virus infection. Nature 1988; 331:82-84.
4. Capon D J, Chamow S M, Mordenti J et al. Designing CD4 immunoadhesins for AIDS therapy. Nature 1989; 337:525-531.
5. Allaway G P, Davis-Bruno K L, Beaudry G A et al. Expression and characterization of CD4-IgG2, a novel heterotetramer which neutralizes primary HIV-1 isolates. AIDS Research and Human Retroviruses 1995; 11:533-539.
6. Allaway G P, Ryder A M, Beaudry G A, Maddon P J. Synergistic inhibition of HIV-1 envelope-mediated cell fusion by CD4-based molecules in combination with antibodies to gp120 or gp41. AIDS Research & Human Retroviruses 1993; 9:581-587.
7. Vita C, Drakopoulou E, Vizzavona J et al. Rational engineering of a miniprotein that reproduces the core of the CD4 site interacting with HIV-1 envelope glycoprotein. Proc Natl Acad Sci USA 1999; 96:13091-13096.
8. Schacker T., Coombs R W., Collier A C. et al. The effects of high-dose recombinant soluble CD4 on human immunodeficiency virus type 1 viremia. Journal of Infectious Diseases 1994; 169:37-40.
9. Schacker T, Collier A C, Coombs R et al. Phase I study of high-dose, intravenous rsCD4 in subjects with advanced HIV-1 infection. J Acquir Immune Defic Syndr Hum Retrovirol 1995; 9:145-152.
10. Collier A C, Coombs R W, Katzenstein D et al. Safety, pharmacokinetics, and antiviral response of CD4-immunoglobulin G by intravenous bolus in AIDS and AIDS-related complex. J Acquir Immune Defic Syndr Hum Retrovirol 1995; 10:150-156.
11. Trkola A., Pomales A P., Yuan H. et al. Cross-clade neutralization of primary isolates of human immunodeficiency virus type 1 by human monoclonal antibodies and tetrameric CD4-IgG2. Journal of Virology 1995; 69:6609-6617.
12. Gauduin M-C., Allaway G P., Maddon P J., Barbas CF3, Burton D R, Koup R A. Effective ex vivo neutralization of plasma HIV-1 by recombinant immunoglobulin molecules. Journal of Virology 1996; 70:2586-2592.
13. Gauduin M-C., Allaway G P, Olson W C, Weir R., Maddon P J, Koup R A. CD4-immunoglobulin G2 protects Hu-PBL-SCID mice against challenge by primary human immunodeficiency virus type 1 isolates. Journal of Virology 1998; 72:3475-3478.
14. Trkola A, Ketas T, KewalRamani V N et al. Neutralization sensitivity of human immunodeficiency virus type 1 primary isolates to antibodies and CD4-based reagents is independent of coreceptor usage. J Virol 1998; 72:1876-1885.
15. Fouts T R, Binley J M, Trkola A, Robinson J E, Moore J P. Neutralization of the human immunodeficiency virus type 1 primary isolate JR-FL by human monoclonal antibodies correlates with antibody binding to the oligomeric form of the envelope glycoprotein complex. Journal of Virology 1997; 71:2779-2785.
16. Jacobson J, Lowy I, Trkola A et al. Results of a Rhase I Trial of Single-Dose PRO542, a Novel Inhibitor of HIV Entry. Abstracts of the 39th Interscience Conference on Antimicrobial Agents and Chemotherapy 1999; 14.
17. Burton D R, Pyati J, Koduri R et al. Efficient neutralization of primary isolates of HIV-1 by a recombinant human monoclonal antibody. Science 1994; 266:1024-1027.
18. Posner M R., Cavacini L A., Emes C L., Power J., Byrn R. Neutralization of HIV-1 by E105, a human monoclonal antibody to the CD4 binding site of gp120. Journal of Acquired Immune Deficiency Syndromes 1993; 6:7-14.
19. Litwin V, Nagashima K A, Ryder A M et al. Human immunodeficiency virus type 1 membrane fusion mediated by a laboratory-adapted strain and a primary isolate analyzed by resonance energy transfer. Journal of Virology 1996; 70:6437-6441.
20. Poignard P, Peng T, Sabbe R, Newman W, Mosier D E, Burton D R. Blocking of HIV-1 Co-receptor CCR5 in the hu-PBL-SCID Mouse Leads to a Co-receptor Switch. 6th Conference on Retroviruses and Opportunistic Infections 1999;
21. Cushman M, Wang P L, Chang S H et al. Preparation and anti-HIV activities of aurintricarboxylic acid fractions and analogues: direct correlation of antiviral potency with molecular weight. J Med Chem 1991; 34:329-337.
22. Mohan P, Schols D, Baba M, De Clercq E. Sulfonic acid polymers as a new class of human immunodeficiency virus inhibitors. Antiviral Res 1992; 18:139-150.
23. Schols D, Pauwels R, Desmyter J, De Clercq E. Dextran sulfate and other polyanionic anti-HIV compounds specifically interact with the viral gp120 glycoprotein expressed by T-cells persistently infected with HIV-1. Virology 1990; 175:556-561.
24. Schols D, Wutzler P, Klocking R, Helbig B, De Clercq E. Selective inhibitory activity of polyhydroxycarboxylates derived from phenolic compounds against human immunodeficiency virus replication. J Acquir Immune Defic Syndr 1991; 4:677-685.
25. Weissenhorn W, Dessen A, Harrison S C, Skehel J J, Wiley D C. Atomic structure of the ectodomain from HIV-1 gp41. Nature 1997; 387:426-430.
26. Chan D C, Fass D, Berger J M, Kim P S. Core Structure of gp41 from the HIV Envelope Glycoprotein. Cell 1997; 89:263-273.
27. Ji H, Shu W, Burling F T, Jiang S, Lu M. Inhibition of human immunodeficiency virus type 1 infectivity by the gp41 core: role of a conserved hydrophobic cavity in membrane fusion. Journal of Virology 1999; 73:8578-8586.
28. Jiang S, Lin K, Strick N, Neurath A R. HIV-1 inhibition by a peptide. Nature 1993; 365:113.
29. Wild C, Greenwell T, Matthews T. A synthetic peptide from HIV-1 gp41 is a potent inhibitor of virus-mediated cell-cell fusion. AIDS Res Hum Retroviruses 1993; 9:1051-1053.
30. Wild C, Greenwell T, Shugars D, Rimsky-Clarke L, Matthews T. The inhibitory activity of an HIV type 1 peptide correlates with its ability to interact with a leucine zipper structure. AIDS Res Hum Retroviruses 1995; 11:323-325.
31. Wild C, Oas T, McDanal C, Bolognesi D, Matthews T. A synthetic peptide inhibitor of human immunodeficiency virus replication: correlation between solution structure and viral inhibition. Proc Natl Acad Sci U S A 1992; 89:10537-10541.
32. Wild C T, Shugars D C, Greenwell T K, McDanal C B, Matthews T J. Peptides corresponding to a predictive alpha-helical domain of human immunodeficiency virus type 1 gp41 are potent inhibitors of virus infection. Proc Natl Acad Sci USA 1994; 91:9770-9774.
33. Chan D C, Chutkowski C T, Kim P S. Evidence that a prominent cavity in the coiled coil of HIV type 1 gp41 is an attractive drug target. Proc Natl Acad Sci USA 1998; 95:15613-15617.
34. Ferrer M, Kapoor T M, Strassmaier T et al. Selection of gp41-mediated HIV-1 cell entry inhibitors from biased combinatorial libraries of non-natural binding elements. Nat Struct Biol 1999; 6:953-960.
35. Eckert D M, Malashkevich V N, Hong L H, Carr P A, Kim P S. Inhibiting HIV-1 entry: discovery of D-peptide inhibitors that target the gp41 coiled-coil pocket. Cell 1999; 99:103-115.
36. Kilby J M, Hopkins S, Venetta T M et al. Potent suppression of HIV-1 replication in humans by T-20, a peptide inhibitor of gp41-mediated virus entry. Nat Med 1998; 4:1302-1307.
37. LaCasse R A, Follis K E, Trahey M, Scarborough J D, Littman D R, Nunberg J H. Fusion-competent vaccines: broad neutralization of primary isolates of HIV. Science 1999; 283:357-362.
38. Neurath A R, Strick N, Lin K, Jiang S. Multifaceted consequences of anti-gp41 monoclonal antibody 2F5 binding to HIV type 1 virions. AIDS Res Hum Retroviruses 1995; 11:687-696.
39. Thali M, Furman C, Wahren B et al. Cooperativity of neutralizing antibodies directed against the V3 and CD4 binding regions of the human immunodeficiency virus gp120 envelope glycoprotein. J Acquir Immune Defic Syndr 1992; 5:591-599.
40. Tilley S A, Honnen W J, Racho M E, Chou T C, Pinter A. Synergistic neutralization of HIV-1 by human monoclonal antibodies against the V3 loop and the CD4-binding site of gp120. AIDS Res Hum Retroviruses 1992; 8:461-467.
41. Laal S, Burda S, Gorny M K, Karwowska S, Buchbinder A, Zolla-Pazner S. Synergistic neutralization of human immunodeficiency virus type 1 by combinations of human monoclonal antibodies. Journal of Virology 1994; 68:4001-4008.
42. Vijh-Warrier S, Pinter A, Honnen W J, Tilley S A. Synergistic neutralization of human immunodeficiency virus type 1 by a chimpanzee monoclonal antibody against the V2 domain of gp120 in combination with monoclonal antibodies against the V3 loop and the CD4-binding site. Journal of Virology 1996; 70:4466-4473.
43. Li A, Baba T W, Sodroski J et al. Synergistic neutralization of a chimeric SIV/HIV type 1 virus with combinations of human anti-HIV type 1 envelope monoclonal antibodies or hyperimmune globulins. AIDS Res Hum Retroviruses 1997; 13:647-656.
44. Li A, Katinger H, Posner M R et al. Synergistic neutralization of simian-human immunodeficiency virus SHIV-vpu+ by triple and quadruple combinations of human monoclonal antibodies and high-titer anti-human immunodeficiency virus type 1 immunoglobulins. Journal of Virology 1998; 72:3235-3240.
45. Burkly L, Mulrey N, Blumenthal R, Dimitrov D S. Synergistic inhibition of human immunodeficiency virus type 1 envelope glycoprotein-mediated cell fusion and infection by an antibody to CD4 domain 2 in combination with anti-gp120 antibodies. Journal of Virology 1995; 69:4267-4273.
46. Olson W C, Rabut G E, Nagashima K A et al. Differential inhibition of human immunodeficiency virus type 1 fusion, gp120 binding, and CC-chemokine activity by monoclonal antibodies to CCR5. J Virol 1999; 73:4145-4155.
47. O'Brien W A., Koyanagi Y., Namazie A. et al. HIV-1 tropism for mononuclear phagocytes can be determined by regions of gp120 outside the CD4-binding domain. Nature 1990; 348:69-73.
48. Trkola A, Matthews J, Gordon C, Ketas T, Moore J P. A cell line-based neutralization assay for primary human immunodeficiency virus type 1 isolates that use either the CCR5 or the CXCR4 coreceptor. J Virol 1999; 73:8966-8974.
49. Fouts T R, Trkola A, Fung M S, Moore J P. Interactions of polyclonal and monoclonal anti-glycoprotein 120 antibodies with oligomeric glycoprotein 120-glycoprotein 41 complexes of a primary HIV type 1 isolate: relationship to neutralization. AIDS Res Hum Retroviruses 1998; 14:591-597.
50. Dreyer K, Kallas E G, Planelles V, Montefiori D, McDermott M P, Hasan M S. Primary isolate neutralization by HIV type 1-infected patient sera in the era of highly active antiretroviral therapy. AIDS Research and Human Retroviruses 1999; 15:1563-1571.
51. Allaway G P, Litwin V M, Maddon P J. Progenics Pharmaceuticals, Inc. Methods for using resonance energy transfer-based assay of HIV-1 envelope glycoprotein-mediated membrane fusion, and kits for practicing same. International Filing Date Jun. 7, 1996. International Patent Application No. PCT/US96/09894. 1996;
52. Chou T C. The median effect principle and the combination index for quantitation of synergism and antagonism. Synergism and Antagonism in Chemotherapy 1991; 61-102.
53. Chou T C, Talalay P. Quantitative analysis of dose-effect relationships: the combined effects of multiple drugs or enzyme inhibitors. Advances in Enzyme Regulation 1984; 22:27-55.
54. Dragic T., Litwin V., Allaway G P. et al. HIV-1 entry into CD4+ cells is mediated by the chemokine receptor CC-CKR-5. Nature 1996; 381:667.
55. Donzella G A, Schols D, Lin S W et al. AMD3100, a small molecule inhibitor of HIV-1 entry via the CXCR4 co-receptor. Nature Medicine 1998; 4:72-77.
56. Johnson V A, Merrill D P, Videler J A et al. Two-drug combinations of zidovudine, didanosine, and recombinant interferon-alpha A inhibit replication of zidovudine-resistant human immunodeficiency virus type 1 synergistically in vitro. Journal of Infectious Diseases 1991; 164:646-655.
57. Merrill D P, Manion D J, Chou T C, Hirsch M S. Antagonism between human immunodeficiency virus type 1 protease inhibitors indinavir and saquinavir in vitro. Journal of Infectious Diseases 1997; 176:265-268.
58. U.S. Pat. No. 4,816,567, issued Mar. 28, 1989 to Cabilly et al.
59. U.S. Pat. No. 5,225,539, issued Jul. 6, 1993 to Gregory Winter.
60. U.S. Pat. No. 5,585,089, issued Dec. 17, 1996 to Queen et al.
61. U.S. Pat. No. 5,693,761, issued Dec. 2, 1997 to Queen et al.
62. PCT International Application No. PCT/US89/05857, filed Dec. 28, 1989, published Jul. 26, 1990, WO 90/07861.
63. Jacobson, J. M. et al. Single-dose safety, pharmacology and antiviral activity of the human immunodeficiency virus (HIV) type 1 entry inhibitor PRO 542 in HIV-infected adults. J. Infect. Dis 182:326-329.
64. Kilby, J. M. et al. 1998 Potent suppression of HIV-1 replication in humans by T-20, a peptide inhibitor of gp-41 mediated virus entry. Nat. Med 4:1302-1307.
65. Olson. W. C. et al. 1999. Differential inhibition of human immunodeficiency virus type 1 fusion, gp120 binding, and CC-chemokine activity by monoclonal antibodies to CCR5. J. Virol 73:4145-4155.
66. Tremblay, C. et al. 2000. Strong in vitro synergy observed between the fusion inhibitor T-20 and a CxCR4 blocker AMD-3100. 7$^{th}$ Conference on Retroviruses and Opportunistic Infections, San Francisco.
67. Litwin, V. et al 1996, J. Virol 70:6437-6441.

Second Series of Experiments

Infection of cells by human immunodeficiency virus type 1 (HIV-1) is mediated by the viral envelope (env) glycoproteins gp120 and gp41, which are expressed as a noncovalent, oligomeric complex on the surface of virus and virally infected cells. HIV-1 entry into target cells proceeds at the cell surface through a cascade of events that include (1) binding of the viral surface glycoprotein gp120 to cell surface CD4, which is the primary receptor for HIV-1, (2) env binding to fusion coreceptors such as CCR5 and CXCR4, and (3) multiple conformational changes in gp41. During fusion, gp41 adopts transient conformations that include a prehairpin fusion intermediate that ultimately folds into a conformation capable of mediating fusion. These events culminate in fusion of the viral and cellular membranes and the subsequent introduction of the viral genome into the target cell. A similar sequence of molecular events is required for infection to spread via fusion of infected and uninfected cells. Each stage of the viral entry process can be targeted for therapeutic intervention.

HIV-1 attachment can be inhibited both by agents that bind the viral envelope glycoproteins and by agents that bind human CD4. Notably, HIV-1 attachment can be inhibited by compounds that incorporate the gp120-binding domains of human CD4 and molecular mimics thereof [1-7]. Because this interaction between gp120 and CD4 is essential for virus infection, CD4-based molecules have the potential to target most if not all strains of HIV-1. In addition, viruses have limited ability to develop resistance to such molecules.

The determinants for gp120 binding map to the first extracellular domain (D1) on CD4 [1], and the amino acids critical for binding center on a loop comprising amino acids 36-47. Potent HIV-1 inhibitory activity has been reproduced in a 27-amino acid peptide that mimics this loop and surrounding structures [7].

A number of recombinant CD4-based molecules have been developed and tested for clinical activity in man. The first of these contained the four extracellular domains (D1-D4) of CD4 but lacked the transmembrane and intracellular regions. This molecule, termed soluble CD4 (sCD4), demonstrated excellent tolerability when administered to humans at doses ranging to 10 mg/kg [8,9]. Transient reductions in plasma levels of infectious HIV-1 were observed in certain patients treated with sCD4. The short half-life of sCD4 in humans (45 minutes following intravenous administration) was identified as one obstacle to using this agent for chronic therapy.

Second-generation CD4-based proteins were developed with increased serum half-life. These CD4-immunoglobulin fusion proteins comprised the D1D2 domains of CD4 genetically fused to the hinge CH2 and CH3 regions of human IgG molecules. These divalent proteins derive HIV-1 neutralizing capacity from their CD4 domains and Fc effector functions from the IgG molecule. A CD4-IgG1 fusion protein was shown to have excellent tolerability and improved pharmacokinetics in Phase I clinical testing [10]. The antiviral evaluations were inconclusive.

More recently, a third-generation tetravalent CD4-IgG2 fusion protein was developed that comprises the D1D2 domains of CD4 genetically fused to the heavy and light chain constant regions of human IgG2. This agent binds the HIV-1 envelope glycoprotein gp120 with nanomolar affinity [5] and may inhibit virus attachment both by receptor blockade and by detaching gp120 from the virion surface, thereby irreversibly inactivating the virus. In standard PBMC-based neutralization assays, CD4-IgG2 neutralized primary HIV-1 isolates derived from all major subtypes and outlier groups. The CD4-IgG2 concentrations required to achieve a 90% reduction in viral infectivity, the in vitro IC90, were approximately 15-20 µg/ml [11], concentrations that are readily achievable in vivo. CD4-IgG2 was similarly effective in neutralizing HIV-1 obtained directly from the plasma of seropositive donors in an ex vivo assay, indicating that this agent is active against the diverse viral quasispecies that are encountered clinically [12]. CD4-IgG2 also provided protection against infection by primary isolates in the hu-PBL-SCID mouse model of HIV-1 infection [13]. Recent analyses have demonstrated that CD4-IgG2's ability to neutralize primary viruses is independent of their coreceptor usage [14].

Compared with mono- or divalent CD4-based proteins, CD4-IgG2 has consistently demonstrated as much as 100-fold greater potency at inhibiting primary HIV-1 isolates [5,12,14,15]. The heightened potency may derive from CD4-IgG2's ability to bind virions with increased valency/avidity and its steric juxtaposition of two gp120 binding sites on each Fab-like arm of the immunoglobulin molecule. The larger Fab-like arms of CD4-IgG2 are also more likely to span HIV-1 envelope spikes on the virion. In a variety of preclinical models, CD4-IgG2's anti-HIV-1 activity has been shown to compare favorably with those of the rare human monoclonal antibodies that broadly and potently neutralize primary HIV-1 isolates [5,11,14,15]. In addition, CD4-IgG2 therapy is in principle less susceptible to the development of drug-resistant viruses than therapies employing anti-env monoclonal antibodies or portions of the highly mutable HIV-1 envelope glycoproteins. These properties suggest that CD4-IgG2 may have clinical utility as an agent that neutralizes cell-free virus before it has the opportunity to establish new rounds of infection. In addition to treatment, CD4-IgG2 may have utility in preventing infection resulting from occupational, perinatal or other exposure to HIV-1.

In Phase I clinical testing, single-dose CD4-IgG2 demonstrated excellent pharmacology and tolerability. In addition, measurable antiviral activity was observed by each of two measures. First, a statistically significant acute reduction in plasma HIV RNA was observed following administration of a single 10 mg/kg dose. In addition, sustained reductions in plasma levels of infectious HIV were observed in each of two patients tested. Taken together, these observations indicate that CD4-IgG2 possesses antiviral activity in humans [16].

In addition to CD4-based proteins and molecular mimics thereof, HIV-1 attachment can also be inhibited by antibodies and nonpeptidyl molecules. Known inhibitors include (1) anti-env antibodies such as IgG1b12 and F105 [17,18], (2) anti-CD4 antibodies such as OKT4A, Leu 3a, and humanized versions thereof [19,20], and (3) nonpeptidyl agents that target either gp120 or CD4 [21], [22-24]. The latter group of compounds includes aurintricarboxylic acids, polyhydroxycarboxylates, sulfonic acid polymers, and dextran sulfates.

Several agents have been identified that block HIV-1 infection by targeting gp41 fusion intermediates. These inhibitors may interact with the fusion intermediates and prevent them from folding into final fusogenic conformations. The first such agents to be identified comprised synthetic or recombinant peptides corresponding to portions of the gp41 ectodomain predicted to form hydrophobic alpha helices. One such region is present in both the amino and carboxy segments of the extracellular portion of gp41, and recent crystallographic evidence suggests that these regions interact in the presumed fusogenic conformation of gp41 [25,26]. HIV-1 infection can be inhibited by agents that bind to either N- or C-terminal gp41 epitopes that are exposed during fusion. These agents include the gp41-based peptides T-20 (formerly known as DP178), T-1249, DP107, N34, C28, and various fusion proteins and analogues thereof [27-33]. Other studies have identified inhibitors that comprise non-natural D-peptides and nonpeptidyl moieties [34,35]. Clinical proof-of-concept for this class of inhibitors has been provided by T-20, which reduced plasma HIV RNA levels by as much as 2 logs in Phase I/II human clinical testing [36]. The broad antiviral activity demonstrated for this class of inhibitors reflects the high degree of gp41 sequence conservation amongst diverse strains of HIV-1.

Recent studies [37] have demonstrated the possibility of raising antibodies against HIV-1 fusion intermediates. This work employed "fusion-competent" HIV vaccine immunogens that capture transient fusion intermediates formed upon interaction of gp120/gp41 with CD4 and fusion coreceptors. The immunogens used in these studies were formalin-fixed cocultures of cells that express HIV-1 gp120/gp41 and cells that express human CD4 and CCR5 but not CXCR4. The antibodies elicited by the vaccines demonstrated unprecedented breadth and potency in inhibiting primary HIV-1 isolates regardless of their coreceptor usage, indicating that the antibodies were raised against structures such as gp41 fusion intermediates that are highly conserved and transiently exposed during HIV-1 entry. This class of antibodies does not include the anti-gp41 monoclonal antibody known as 2F5, which interacts with an epitope that is constitutively presented on virus particles prior to fusion [38].

Previously, synergistic inhibition of HIV-1 entry has been demonstrated using certain anti-env antibodies used in combination with other anti-env antibodies [39-44], anti-CD4 antibodies [45], or CD4-based proteins [6]. Similarly, synergies have been observed using anti-CCR5 antibodies used in combination with other anti-CCR5 antibodies, CC-chemokines, or CD4-based proteins [46]. However, no prior studies have examined the potential synergistic effects of combining inhibitors of gp41 fusion intermediates with inhibitors of other stages of HIV-1 entry. In particular, no studies have examined combinations of inhibitors of gp41 fusion intermediates and HIV-1 attachment.

A. Materials and Methods

1) Reagents

Purified recombinant CD4-IgG2 protein was produced by Progenics Pharmaceuticals, Inc. from plasmids CD4-IgG2-HC-pRcCMV and CD4-kLC-pRcCMV (ATCC Accession Nos. 75193 and 75194, respectively) as described [5]. HeLa-env cells were prepared by transfecting HeLa cells (ATCC Catalog # CCL-2) with HIV-1 gp120/gp41 env-expressing plasmid pMA243 as described [51]. PM1 cells are available from the National Institutes of Health AIDS Reagent Program (Catalog #3038). The T-20 peptide was synthesized using standard solid-phase Fmoc chemistry and purified and characterized as described [31,32].

2) Inhibition of HIV-1 env-Mediated Membrane Fusion

HIV-1 envelope-mediated fusion between HeLa-Env$_{JR-FL}$ and PM1 cells was detected using a Resonance Energy Transfer (RET) assay. Equal numbers (2×10$^4$) of fluorescein octadecyl ester (F18)-labeled envelope-expressing cells and octadecyl rhodamine (R18)-labeled PM1 cells were plated in 96-well plates in 15% fetal calf serum in phosphate buffered saline and incubated for 4 h at 37 (C in the presence of varying concentrations of CD4-IgG2, T-20 or combinations thereof. Fluorescence RET was measured with a Cytofluor plate-reader (PerSeptive Biosystems) and % RET was determined as previously described [19].

3) Quantitative Analysis of the Synergistic, Additive or Antagonistic Effects of Combining the Agents HIV-1 inhibition data were analyzed according to the Combination Index method of Chou and Talay [52,53]. The data are modeled according to the median-effect principle, which can be written $$f=1/[1+(K/c)^m] \quad (1)$$

where f is the fraction affected/inhibited, c is concentration, K is the concentration of agent required to produce the median effect, and m is an empirical coefficient describing the shape of the dose-response curve. Equation (1) is a generalized form of the equations describing Michaelis-Menton enzyme kinetics, Langmuir adsorption isotherms, and Henderson-Hasselbalch ionization equilibria, for which m=1 in all cases. In the present case, K is equal to the $IC_{50}$ value. K and m are determined by curve-fitting the dose-response curves.

After the best-fit parameters for K and m are obtained for the experimental agents and their combination, Equation (1) is rearranged to allow for calculation of c for a given f. The resulting table of values (e.g., Figure X) is used to calculate the Combination Index (CI) using the equation $$CI = c_{1m}/c_1 + c_{2m}/c_2 + c_{1m}c_{2m}/c_1c_2 \qquad (2)$$

where $c_1$=concentration of compound 1 when used alone
$c_2$ concentration of compound 2 when used alone
$c_{1m}$=concentration of compound 1 in the mixture
$c_{2m}$=concentration of compound 2 in the mixture All concentrations are those required to achieve a given degree of inhibition. Equation (2) is used when the molecules are mutually nonexclusive, i.e., have different sites of action. Since this is the likely scenario for inhibitors of HIV-1 attachment and gp41 fusion intermediates, Equation (2) was used for all Combination Index calculations. Mutually nonexclusive calculations provide a more conservative estimate of the degree of synergy that mutually exclusive calculations, for which the $c_{1m}c_{2m}/c_1c_2$ term is dropped. CI<1 indicates synergy, CI=1 indicates purely additive effects, and CI>1 indicates antagonism. In general, CI values are most relevant at the higher levels of inhibition that are required to achieve a measurable clinical benefit.

B. Results and Discussion

Combinations of inhibitors of HIV-1 attachment and gp41 fusion intermediates were first tested for the ability to inhibit HIV-1 env-mediated membrane fusion in the RET assay. This assay has proven to be a highly successful model of the HIV-1 entry process. In this assay, env-dependent coreceptor usage patterns and cellular tropisms of the parental viruses are accurately reproduced [19]. Indeed, the assay was instrumental in demonstrating that CCR5 functions as a requisite fusion coreceptor and acts at the level of viral entry [54]. The fusion assay and infectious virus are similarly sensitive to inhibition by metal chelators and agents that target the full complement of viral and cellular receptors [19,46,55].

Dose-response curves were obtained for the agents used individually and in combination in both assays. Data were analyzed using the median effect principle [52,53]. The concentrations of single-agents or their mixtures required to produce a given effect were quantitatively compared in a term known as the Combination Index (CI). CI>1 indicates antagonism, CI=1 indicates a purely additive effect, and CI<1 indicates a synergistic effect wherein the presence of one agent enhances the effect of another.

Figure 6:
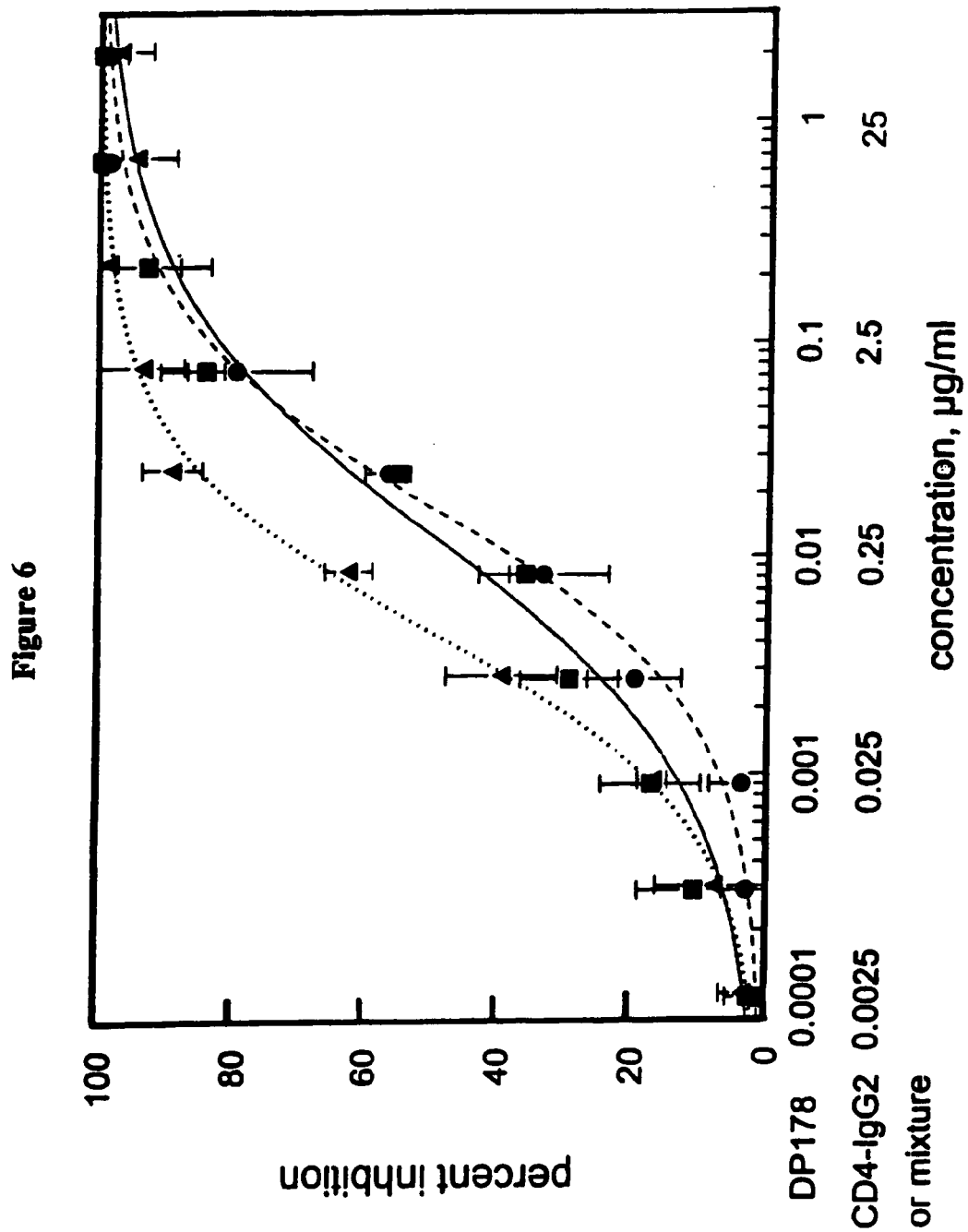

Combinations of CD4-IgG2 and T-20 were observed to be potently synergistic in inhibiting env-mediated membrane fusion. FIG. 6 illustrates representative dose-response curves obtained in the membrane fusion assay for CD4-IgG2, T-20, and combinations of the two. The curve for the combination is highly displaced towards lower inhibitor concentrations and provides qualitative evidence that CD4-IgG2 and T-20 act in a synergistic manner.

To quantitatively calculate the degree of synergy observed between CD4-IgG2 and T-20, we analyzed the dose-response curves according to the Combination Index method [52,53]. The analysis included data obtained at 25:1, 5:1, and 1:1 CD4-IgG2:T-20 mass ratios. At the 25:1 mass ratio, both high (0-250 μg/ml CD4-IgG2 and 0-10 μg/ml T-20) and low (0-50 μg/ml CD4-IgG2 and 0-2 μg/ml T-20) concentration ranges were evaluated. As indicated in FIG. 7, potent synergies were observed over these broad ranges of inhibitor ratios and concentrations, with CI values as low as 0.20 under optimal conditions. This degree of synergy is remarkable since CI values of 0.2 are rarely observed for combinations involving anti-HIV-1 antibodies [41-44], reverse transcriptase inhibitors [56], or protease inhibitors [57]. The observed synergies indicate that HIV-1 attachment and formation of gp41 fusion intermediates are inter-dependent steps. One possibility is that attachment inhibitors, when used at suboptimal concentrations, may slow but not abrogate the binding of gp120 to CD4. In this case, gp41 fusion intermediates may be formed and persist on the virus (or infected cell) for longer periods of time at levels below that required for membrane fusion and thus provide better targets for inhibitory agents.

The observed synergies translate into significant reductions in the amounts of CD4-IgG2 and T-20 needed for inhibition. These reductions are illustrated in FIG. 8 for CD4-IgG2 and T-20 used in a 25:1 mass ratio. By way of example, inhibition of viral entry by 95% requires 0.21 μg/ml of T-20 used alone, 19 μg/ml of CD4-IgG2 used alone and 1.14 μg/ml of a combination containing 0.044 μg/ml of T-20 and 1.1 μg/ml of CD4-IgG2. The combination reduces the respective doses of T-20 and CD4-IgG2 by 5- and 17-fold, respectively. Still greater dose reductions are observed at higher levels of inhibition.

REFERENCES FOR SECOND SERIES OF EXPERIMENTS

1. Arthos J, Deen K C, Chaikin M A et al. Identification of the residues in human CD4 critical for the binding of HIV. Cell 1989; 57:469-481.
2. Clapham P R., Weber J N., Whitby D. et al. Soluble CD4 blocks the infectivity of diverse strains of HIV and SIV for T cells and monocytes but not for brain and muscle cells. Nature 1989; 337:368-370.
3. Deen K C., McDougal JS., Inacker R. et al. A soluble form of CD4 (T4) protein inhibits AIDS virus infection. Nature 1988; 331:82-84.
4. Capon D J, Chamow S M, Mordenti J et al. Designing CD4 immunoadhesins for AIDS therapy. Nature 1989; 337:525-531.
5. Allaway G P, Davis-Bruno K L, Beaudry G A et al. Expression and characterization of CD4-IgG2, a novel heterotetramer which neutralizes primary HIV-1 isolates. AIDS Research and Human Retroviruses 1995; 11:533-539.
6. Allaway G P, Ryder A M, Beaudry G A, Maddon P J. Synergistic inhibition of HIV-1 envelope-mediated cell fusion by CD4-based molecules in combination with antibodies to gp120 or gp41. AIDS Research & Human Retroviruses 1993; 9:581-587.
7. Vita C, Drakopoulou E, Vizzavona J et al. Rational engineering of a miniprotein that reproduces the core of the CD4 site interacting with HIV-1 envelope glycoprotein. Proc Natl Acad Sci USA 1999; 96:13091-13096.
8. Schacker T., Coombs R W., Collier A C. et al. The effects of high-dose recombinant soluble CD4 on human immunodeficiency virus type 1 viremia. Journal of Infectious Diseases 1994; 169:37-40.

9. Schacker T, Collier A C, Coombs R et al. Phase I study of high-dose, intravenous rsCD4 in subjects with advanced HIV-1 infection. J Acquir Immune Defic Syndr Hum Retrovirol 1995; 9:145-152.
10. Collier A C, Coombs R W, Katzenstein D et al. Safety, pharmacokinetics, and antiviral response of CD4-immunoglobulin G by intravenous bolus in AIDS and AIDS-related complex. J Acquir Immune Defic Syndr Hum Retrovirol 1995; 10:150-156.
11. Trkola A., Pomales A P., Yuan H. et al. Cross-clade neutralization of primary isolates of human immunodeficiency virus type 1 by human monoclonal antibodies and tetrameric CD4-IgG2. Journal of Virology 1995; 69:6609-6617.
12. Gauduin M-C., Allaway G P., Maddon P J., Barbas CF3, Burton D R, Koup R A. Effective ex vivo neutralization of plasma HIV-1 by recombinant immunoglobulin molecules. Journal of Virology 1996; 70:2586-2592.
13. Gauduin M-C., Allaway G P, Olson W C, Weir R., Maddon P J, Koup R A. CD4-immunoglobulin G2 protects Hu-PBL-SCID mice against challenge by primary human immunodeficiency virus type 1 isolates. Journal of Virology 1998; 72:3475-3478.
14. Trkola A, Ketas T, KewalRamani V N et al. Neutralization sensitivity of human immunodeficiency virus type 1 primary isolates to antibodies and CD4-based reagents is independent of coreceptor usage. J Virol 1998; 72:1876-1885.
15. Fouts T R, Binley J M, Trkola A, Robinson J E, Moore J P. Neutralization of the human immunodeficiency virus type 1 primary isolate JR-FL by human monoclonal antibodies correlates with antibody binding to the oligomeric form of the envelope glycoprotein complex. Journal of Virology 1997; 71:2779-2785.
16. Jacobson J, Lowy I, Trkola A et al. Results of a Rhase I Trial of Single-Dose PRO 542, a Novel Inhibitor of HIV Entry. Abstracts of the 39th Interscience Conference on Antimicrobial Agents and Chemotherapy 1999; 14.
17. Burton D R, Pyati J, Koduri R et al. Efficient neutralization of primary isolates of HIV-1 by a recombinant human monoclonal antibody. Science 1994; 266:1024-1027.
18. Posner M R., Cavacini L A., Emes C L., Power J., Byrn R. Neutralization of HIV-1 by F105, a human monoclonal antibody to the CD4 binding site of gp120. Journal of Acquired Immune Deficiency Syndromes 1993; 6:7-14.
19. Litwin V, Nagashima K A, Ryder A M et al. Human immunodeficiency virus type 1 membrane fusion mediated by a laboratory-adapted strain and a primary isolate analyzed by resonance energy transfer. Journal of Virology 1996; 70:6437-6441.
20. Poignard P, Peng T, Sabbe R, Newman W, Mosier D E, Burton D R. Blocking of HIV-1 Co-receptor CCR5 in the hu-PBL-SCID Mouse Leads to a Co-receptor Switch. 6th Conference on Retroviruses and Opportunistic Infections 1999;
21. Cushman M, Wang P L, Chang S H et al. Preparation and anti-HIV activities of aurintricarboxylic acid fractions and analogues: direct correlation of antiviral potency with molecular weight. J Med Chem 1991; 34:329-337.
22. Mohan P, Schols D, Baba M, De Clercq E. Sulfonic acid polymers as a new class of human immunodeficiency virus inhibitors. Antiviral Res 1992; 18:139-150.
23. Schols D, Pauwels R, Desmyter J, De Clercq E. Dextran sulfate and other polyanionic anti-HIV compounds specifically interact with the viral gp120 glycoprotein expressed by T-cells persistently infected with HIV-1. Virology 1990; 175:556-561.
24. Schols D, Wutzler P, Klocking R, Helbig B, De Clercq E. Selective inhibitory activity of polyhydroxycarboxylates derived from phenolic compounds against human immunodeficiency virus replication. J Acquir Immune Defic Syndr 1991; 4:677-685.
25. Weissenhorn W, Dessen A, Harrison S C, Skehel J J, Wiley D C. Atomic structure of the ectodomain from HIV-1 gp41. Nature 1997; 387:426-430.
26. Chan D C, Fass D, Berger J M, Kim P S. Core Structure of gp41 from the HIV Envelope Glycoprotein. Cell 1997; 89:263-273.
27. Ji H, Shu W, Burling F T, Jiang S, Lu M. Inhibition of human immunodeficiency virus type 1 infectivity by the gp41 core: role of a conserved hydrophobic cavity in membrane fusion. Journal of Virology 1999; 73:8578-8586.
28. Jiang S, Lin K, Strick N, Neurath A R. HIV-1 inhibition by a peptide. Nature 1993; 365:113.
29. Wild C, Greenwell T, Matthews T. A synthetic peptide from HIV-1 gp41 is a potent inhibitor of virus-mediated cell-cell fusion. AIDS Res Hum Retroviruses 1993; 9:1051-1053.
30. Wild C, Greenwell T, Shugars D, Rimsky-Clarke L, Matthews T. The inhibitory activity of an HIV type 1 peptide correlates with its ability to interact with a leucine zipper structure. AIDS Res Hum Retroviruses 1995; 11:323-325.
31. Wild C, Oas T, McDanal C, Bolognesi D, Matthews T. A synthetic peptide inhibitor of human immunodeficiency virus replication: correlation between solution structure and viral inhibition. Proc Natl Acad Sci U S A 1992; 89:10537-10541.
32. Wild C T, Shugars D C, Greenwell T K, McDanal C B, Matthews T J. Peptides corresponding to a predictive alpha-helical domain of human immunodeficiency virus type 1 gp41 are potent inhibitors of virus infection. Proc Natl Acad Sci USA 1994; 91:9770-9774.
33. Chan D C, Chutkowski C T, Kim P S. Evidence that a prominent cavity in the coiled coil of HIV type 1 gp41 is an attractive drug target. Proc Natl Acad Sci USA 1998; 95:15613-15617.
34. Ferrer M, Kapoor T M, Strassmaier T et al. Selection of gp41-mediated HIV-1 cell entry inhibitors from biased combinatorial libraries of non-natural binding elements. Nat Struct Biol 1999; 6:953-960.
35. Eckert D M, Malashkevich V N, Hong L H, Carr P A, Kim P S. Inhibiting HIV-1 entry: discovery of D-peptide inhibitors that target the gp41 coiled-coil pocket. Cell 1999; 99:103-115.
36. Kilby J M, Hopkins S, Venetta T M et al. Potent suppression of HIV-1 replication in humans by T-20, a peptide inhibitor of gp41-mediated virus entry. Nat Med 1998; 4:1302-1307.
37. LaCasse R A, Follis K E, Trahey M, Scarborough J D, Littman D R, Nunberg J H. Fusion-competent vaccines: broad neutralization of primary isolates of HIV. Science 1999; 283:357-362.
38. Neurath A R, Strick N, Lin K, Jiang S. Multifaceted consequences of anti-gp41 monoclonal antibody 2F5 binding to HIV type 1 virions. AIDS Res Hum Retroviruses 1995; 11:687-696.
39. Thali M, Furman C, Wahren B et al. Cooperativity of neutralizing antibodies directed against the V3 and CD4 binding regions of the human immunodeficiency virus gp120 envelope glycoprotein. J Acquir Immune Defic Syndr 1992; 5:591-599.
40. Tilley S A, Honnen W J, Racho M E, Chou T C, Pinter A. Synergistic neutralization of HIV-1 by human monoclonal antibodies against the V3 loop and the CD4-binding site of gp120. AIDS Res Hum Retroviruses 1992; 8:461-467.

41. Laal S, Burda S, Gorny M K, Karwowska S, Buchbinder A, Zolla-Pazner S. Synergistic neutralization of human immunodeficiency virus type 1 by combinations of human monoclonal antibodies. Journal of Virology 1994; 68:4001-4008.

42. Vijh-Warrier S, Pinter A, Honnen W J, Tilley S A. Synergistic neutralization of human immunodeficiency virus type 1 by a chimpanzee monoclonal antibody against the V2 domain of gp120 in combination with monoclonal antibodies against the V3 loop and the CD4-binding site. Journal of Virology 1996; 70:4466-4473.

43. Li A, Baba T W, Sodroski J et al. Synergistic neutralization of a chimeric SIV/HIV type 1 virus with combinations of human anti-HIV type 1 envelope monoclonal antibodies or hyperimmune globulins. AIDS Res Hum Retroviruses 1997; 13:647-656.

44. Li A, Katinger H, Posner M R et al. Synergistic neutralization of simian-human immunodeficiency virus SHIV-vpu+ by triple and quadruple combinations of human monoclonal antibodies and high-titer anti-human immunodeficiency virus type 1 immunoglobulins. Journal of Virology 1998; 72:3235-3240.

45. Burkly L, Mulrey N, Blumenthal R, Dimitrov D S. Synergistic inhibition of human immunodeficiency virus type 1 envelope glycoprotein-mediated cell fusion and infection by an antibody to CD4 domain 2 in combination with anti-gp120 antibodies. Journal of Virology 1995; 69:4267-4273.

46. Olson W C, Rabut G E, Nagashima K A et al. Differential inhibition of human immunodeficiency virus type 1 fusion, gp120 binding, and CC-chemokine activity by monoclonal antibodies to CCR5. J Virol 1999; 73:4145-4155.

47. O'Brien W A., Koyanagi Y., Namazie A. et al. HIV-1 tropism for mononuclear phagocytes can be determined by regions of gp120 outside the CD4-binding domain. Nature 1990; 348:69-73.

48. Trkola A, Matthews J, Gordon C, Ketas T, Moore J P. A cell line-based neutralization assay for primary human immunodeficiency virus type 1 isolates that use either the CCR5 or the CXCR4 coreceptor. J Virol 1999; 73:8966-8974.

49. Fouts T R, Trkola A, Fung M S, Moore J P. Interactions of polyclonal and monoclonal anti-glycoprotein 120 antibodies with oligomeric glycoprotein 120-glycoprotein 41 complexes of a primary HIV type 1 isolate: relationship to neutralization. AIDS Res Hum Retroviruses 1998; 14:591-597.

50. Dreyer K, Kallas E G, Planelles V, Montefiori D, McDermott M P, Hasan M S. Primary isolate neutralization by HIV type 1-infected patient sera in the era of highly active antiretroviral therapy. AIDS Research and Human Retroviruses 1999; 15:1563-1571.

51. Allaway G P, Litwin V M, Maddon P J. Progenics Pharmaceuticals, Inc. Methods for using resonance energy transfer-based assay of HIV-1 envelope glycoprotein-mediated membrane fusion, and kits for practicing same. International Filing Date Jun. 7, 1996. International Patent Application No. PCT/US96/09894. 1996;

52. Chou T C. The median effect principle and the combination index for quantitation of synergism and antagonism. Synergism and Antagonism in Chemotherapy 1991; 61-102.

53. Chou T C, Talalay P. Quantitative analysis of dose-effect relationships: the combined effects of multiple drugs or enzyme inhibitors. Advances in Enzyme Regulation 1984; 22:27-55.

54. Dragic T., Litwin V., Allaway G P. et al. HIV-1 entry into CD4+ cells is mediated by the chemokine receptor CC-CKR-5. Nature 1996; 381:667.

55. Donzella G A, Schols D, Lin S W et al. AMD3100, a small molecule inhibitor of HIV-1 entry via the CXCR4 co-receptor. Nature Medicine 1998; 4:72-77.

56. Johnson V A, Merrill D P, Videler J A et al. Two-drug combinations of zidovudine, didanosine, and recombinant interferon-alpha A inhibit replication of zidovudine-resistant human immunodeficiency virus type 1 synergistically in vitro. Journal of Infectious Diseases 1991; 164:646-655.

57. Merrill D P, Manion D J, Chou T C, Hirsch M S. Antagonism between human immunodeficiency virus type 1 protease inhibitors indinavir and saquinavir in vitro. Journal of Infectious Diseases 1997; 176:265-268.

Third Series of Experiments

HIV-1 entry proceeds via a cascade of events that afford promising targets for therapy. PRO 542 neutralizes HIV-1 by blocking its attachment to CD4, and T-20 blocks gp41-mediated fusion. Both drugs have shown promise in Phase I/II clinical trials. Here the drugs were tested individually and in combination in preclinical models of HIV-1 infection, and inhibition data were analyzed for cooperativity using the Combination Index method. Synergistic inhibition of virus-cell and cell-cell fusion was observed for phenotypically diverse viruses over a broad range of drug concentrations, often resulting in 10-fold or greater dose reductions in vitro. Additional mechanism-of-action studies probed the molecular basis of the synergies. The markedly enhanced activity observed for the PRO 542:T-20 combination indicates that the multi-step nature of HIV-1 entry leaves the virus particularly vulnerable to combinations of entry inhibitors. These findings provide a strong rationale for evaluating combinations of these agents for therapy in vivo.

Despite recent advances, present therapies for human immunodeficiency virus type 1 (HIV-1) infection are limited by their failure to eradicate HIV-1, the emergence of multi-drug resistant variants, and significant toxicities. Accordingly, there is an urgent need for new therapies that target additional stages of the HIV-1 replicative cycle, such as viral entry.

HIV-1 entry comprises three steps that provide promising targets for therapy: (1) the attachment of the HIV-1 surface glycoprotein gp120 to CD4, (2) the interaction of the gp120-CD4 complex with a coreceptor, and (3) membrane fusion mediated by the HIV-1 transmembrane glycoprotein gp41. Attachment, coreceptor, and fusion inhibitors are broadly referred to as entry inhibitors and are currently in clinical development [1-4].

The attachment inhibitor PRO 542 (CD4-IgG2) is a tetravalent CD4-immunoglobulin fusion protein that potently neutralizes primary HIV-1 isolates [5]. In Phase I/II testing, PRO 542 has demonstrated excellent tolerability and pharmacology and has reduced viral loads as measured by plasma HIV RNA, plasma viremia, and cell-associated virus [1,2]. PRO 542 is currently in Phase II clinical testing.

The fusion inhibitor T-20 is a peptide derived from the C-terminal ectodomain of gp41. T-20 possesses broad-spectrum antiviral activity mediated by its ability to act upon transient gp41 fusion intermediates [6,7]. Although the precise structures of the fusion intermediates are not known, they are known as "pre-hairpin" intermediates based on the post-fusion conformation of gp41. T-20 mediated 1-2 $\log_{10}$ reductions in HIV RNA when used as a single agent in Phase I/II trials and has been associated with prolonged viral suppression when used with FDA-approved antiretrovirals [3,4]. T-20 has entered Phase III clinical testing.

Combinations of antiretroviral medications are required for durable suppression of HIV-1 replication. PRO 542 and T-20 are attractive candidates for combination use because they are well-tolerated, "first-in-class" agents that target distinct stages of HIV-1 entry. Moreover, the multi-step, interdependent nature of HIV-1 entry suggests that these drugs might act in a non-additive manner. In this study, we evaluated these agents individually and in combination in vitro and analyzed the results for cooperative effects. The PRO 542:T-20 combination potently and synergistically inhibited entry of phenotypically diverse HIV-1 isolates over a broad range of experimental conditions. Additional studies shed light on the molecular basis for the enhanced antiviral activity.

Materials and Methods

Compounds PRO 542 was expressed in Chinese hamster ovary cells and purified by column chromatography by Progenics [5]. T-20 was synthesized by solid-phase fluroenylmethoxycarbonyl chemistry, purified by reversed phase chromatography and analyzed for purity and size by HPLC and mass spectroscopy by Progenics. PRO 542 and T-20 were formulated in phosphate buffered saline and stored at $-95°$ C.

HIV-1 virus-cell fusion assays NLluc$^+$env$^-$ viruses were complemented in trans by the envelope glycoproteins (Env) from HIV-1$_{JR-FL}$ (R5) or HIV-1$_{DH123}$ (R5X4) [8]. HeLa-CD4$^+$CCR5$^+$ cells were infected with chimeric reporter viruses containing 50-100 ng/ml of p24 in the presence or absence of drugs. Cells were washed and fed fresh drug-containing media at 2 h and drug-free media at 12 h. After 72 h, cell lysates were assayed for luciferase activity [9].

HIV-1 cell-cell fusion assays Cell-cell fusion mediated by the envelope glycoproteins of HIV-1$_{JR-FL}$ and HIV-1$_{LAI}$ was measured using a fluorescence resonance energy transfer (RET) assay [10], which measures fusion between HeLa cells expressing HIV-1 envelope glycoproteins and CD4$^+$ target cells. The T cell lines PM1 and SupT1 were used as target cells in this study. PM1 endogenously express CCR5 and CXCR4. Cells are membrane-labeled with fluorescent dyes that possess overlapping excitation and emission spectra, such that RET occurs when the dyes are placed in the same membrane following fusion. The RET signal is directly related to the extent of membrane fusion.

Quantitative analysis of drug interactions Inhibition data from three independent assays were averaged and analyzed for cooperative effects using the Combination Index (CI) method [11]. In all analyses, PRO 542 and T-20 were assumed to act non-competitively, which leads to a more conservative estimate of synergy. CI values of <0.9 (or >1.1) were taken to represent meaningful synergy (or antagonism). Dose reductions were calculated as the ratio of drug concentrations required for inhibition when the drug is used, alone or in combination [11].

Results

Inhibition of HIV-1 virus-cell fusion PRO 542, T-20 and 1:2 molar combinations thereof were used to inhibit HIV-1$_{JR-FL}$ and HIV-1$_{DH123}$ entry. For HIV-1$_{JR-FL}$ (FIG. 9a), the concentration required for 90% inhibition (IC$_{90}$) was 12 nM for PRO 542, 45 nM for T-20 and 4.1 nM for the combination (1.5 nM PRO 542 and 2.6 nM T-20). Favorable drug-drug interactions are evident from the fact that the IC$_{90}$ of the combination is substantially lower than that of either compound alone.

Figure 10:
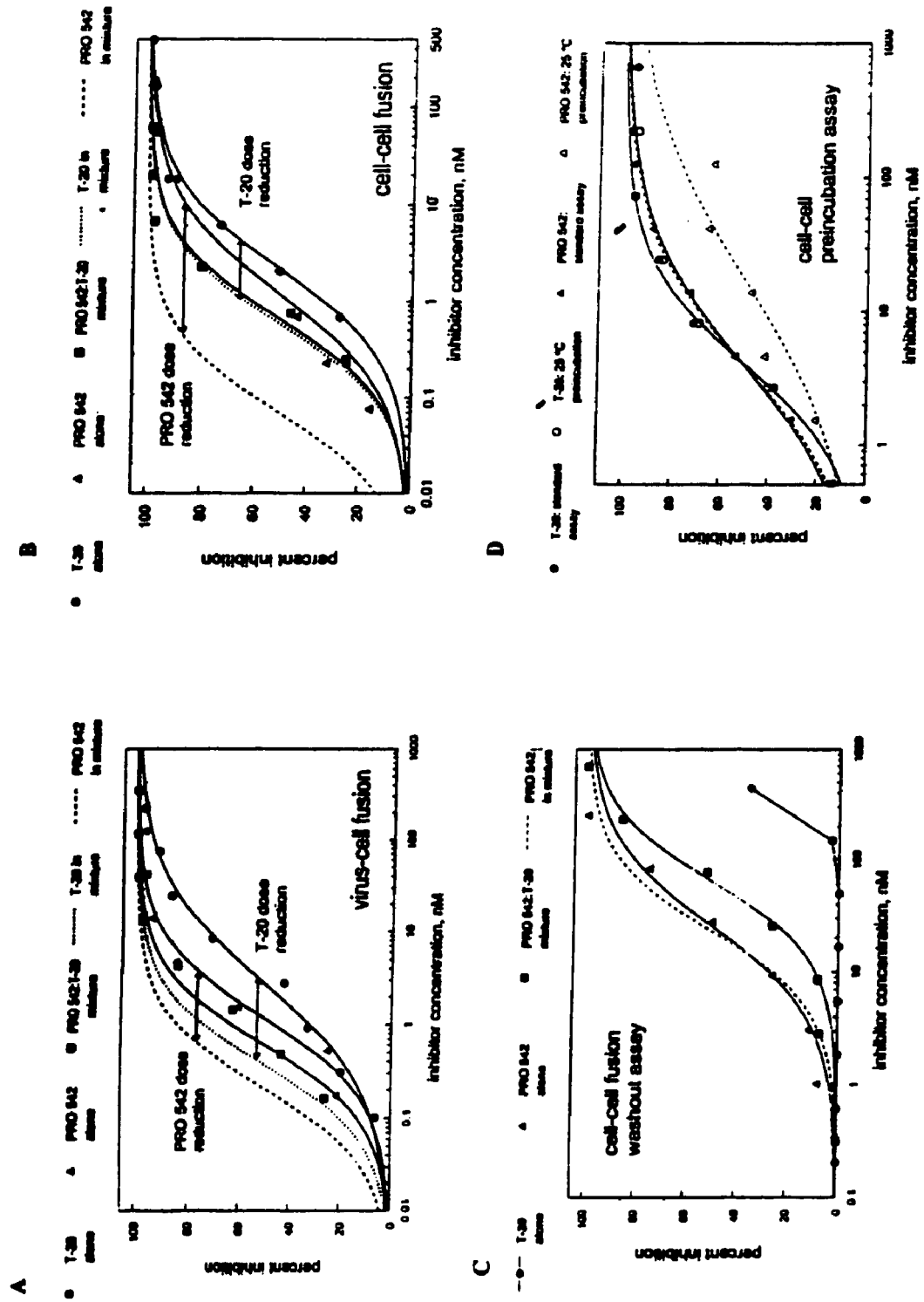

Combination Index analyses (FIG. 10) demonstrated that potent PRO 542:T-20 synergy was observed for both HIV-1$_{JR-FL}$ and HIV-1$_{DH123}$ Over the range of 50-95% inhibition, CI values ranged from 0.39-0.14 for HIV-1$_{JR-FL}$ and 1.1-0.36 for HIV-1$_{DH123}$. Approximately 10-fold less PRO 542 and 20-fold less T-20 was needed to inhibit HIV-1$_{JR-FL}$ entry by 90-95%. Significant dose reductions were also observed for HIV-1$_{DH123}$ (FIG. 10).

Inhibition of HIV-1 Env-mediated cell-cell fusion PRO 542, T-20 and 1:10 molar combinations thereof were used to inhibit HIV-1$_{JR-FL}$ Env-mediated cell-cell fusion in the RET assay (FIG. 9b). IC$_{90}$ values were 11 nM for PRO 542, 22 nM for T-20 and 5.5 nM for the combination (0.55 nM PRO 542 and 4.9 nM T-20). CI values ranged from 0.34-0.27 over the range of 50-95% inhibition (FIG. 10). Robust synergies were also observed using PRO 542:T-20 molar ratios of 1:2 and 1:50 and translated into dose reductions ranging to 50-fold (FIG. 10).

PRO 542 and T-20 also synergistically inhibited HIV-1$_{LAI}$ (X4) Env-mediated fusion. At a 1:10 PRO 542:T-20 ratio, CI values ranged from 0.45-0.28 at 50-95% inhibition. The dose reductions ranged from 12-fold to 30-fold for PRO 542 and from 2.5-fold to 5.4-fold for T-20. Synergy was also observed when the SupT1 T cell line was used instead of PM1 (data not shown).

Mechanistic studies of PRO 542:T-20 synergy T-20 does not interact with Env in its pre-fusion conformation but rather targets transient gp41 structures [7]. PRO 542, on the other hand, neutralizes free virus and triggers Env conformational changes that are required for entry [12]. PRO 542 could conceivably trigger formation of gp41 fusion intermediates, enabling T-20 to act on free virus. To evaluate this hypothesis, PRO 542 and T-20 were pre-incubated alone and in combination for 1 h at 37° C. with HeLa-Env cells prior to washing and the addition of PM1 cells (FIG. 9c). Whereas PRO 542 demonstrated 6-fold lower but nonetheless significant potency, T-20 was essentially inactive in this setting. The potency of the PRO 542:T-20 mixture mirrored that of its PRO 542 content, indicating that T-20 was inactive in the mixture and suggesting that PRO 542 does not trigger formation of the pre-hairpin intermediate. This result also indicates that PRO 542:T-20 synergy does not reflect direct binding between the compounds. Neither drug demonstrated activity when pre-incubated with PM1 cells prior to washing (data not shown).

Further experiments explored the conditions required to form the pre-hairpin intermediate. HeLa-Env and PM1 cells were co-incubated for 2 h at 25° C., a temperature that is not permissive for HIV-1 fusion [13]. Inhibitor was added, and the cells were warmed to 37° C. Whereas PRO 542 was measurably less potent in blocking fusion under these conditions, T-20 was fully active (FIG. 1d). Thus at 25° C., HIV-1 fusion can proceed past gp120-CD4 attachment but is arrested at or before the formation of the pre-hairpin intermediate. Similar results were obtained when the cells were incubated 16 h at 25° C. prior to the addition of inhibitor (data not shown).

Lastly, HeLa-Env cells, PM1 cells, and inhibitor (PRO 542, T-20 or a 1:10 combination) were co-incubated for 2 h at 25° C. prior to washing and warming to 37° C. Under these conditions, PRO 542 demonstrated ~12-fold lower but nonetheless significant activity; T-20 was essentially inactive (>250-fold increase in $IC_{50}$); and the combination possessed activity consistent with its PRO 542 content (data not shown). Taken together, the results indicate that the pre-hairpin intermediate forms only when Env, CD4 and coreceptor interact at a fusion-permissive temperature.

Discussion

HIV-1 entry is a promising target for a new generation of antiretroviral therapies, and PRO 542 and T-20 are "first-in-class" investigational agents that block distinct stages of this highly cooperative process. Recognizing that combinations of entry inhibitors may emerge as a new paradigm for HIV-1 therapy, this study explored PRO 542:T-20 combinations in two preclinical models of HIV-1 infection. Potent synergy was observed for both virus-cell and cell-cell fusion, for phenotypically diverse virus isolates, and over a broad range of drug concentrations. In many instances, the synergy translated into 10-fold or greater dose reductions for PRO 542 and T-20 in vitro. Thus the multi-step nature of HIV-1 entry appears to leave the virus particularly vulnerable to cooperative inhibition. The findings provide a strong rationale for combination clinical trials designed to maximize the therapeutic potential of each compound.

If borne out in vivo, these findings could translate into a number of important clinical benefits. First, more potent therapies reduce the emergence of drug-resistant virus and thereby preserve a patient's therapeutic options. In addition, by reducing the amount of PRO 542 and T-20 required for therapy, the synergy could enable simplified dosing regimens. Dose-sparing regimens are in general also toxicity-sparing, although this may be of less concern for PRO 542 and T-20, which have been well-tolerated in clinical testing to date.

For virus-cell fusion, larger dose reductions were seen for T-20 than for PRO 542, whereas the reverse was true for cell-cell fusion. The relative dose reductions reflect the complementary mechanisms of action of the two products: PRO 542 but not T-20 neutralizes cell-free virus, and T-20 is particularly effective in blocking cell-cell fusion [6-8]. By exploiting the in vitro abilities of each agent to potently block the two major modes of HIV-1 transmission, PRO 542:T-20 combinations may prove to be particularly effective in vivo.

PRO 542 and T-20 synergistically inhibited fusion mediated by R5, X4 and R5X4 virus envelopes. While the activity of PRO 542 against primary viruses is independent of their coreceptor usage [8], T-20's ability to block virus-cell fusion reportedly varies according coreceptor usage [14]. Additional studies with a broader panel of viruses are needed to determine if PRO 542:T-20 synergy is subtly affected by coreceptor usage.

PRO 542 alone was not able to trigger formation of the gp41 pre-hairpin intermediate, which formed only when Env, CD4 and coreceptor interacted at a fusion-permissive temperature. Thus synergy may derive from subtler events, such as the clustering of multiple gp120/gp41 trimers to form the fusion pore [13]. At sub-neutralizing doses, PRO 542 may block a subset of Envs from interacting with target cells, while perhaps allowing other Envs to proceed to the pre-hairpin intermediate. The fusion intermediates may remain exposed and susceptible to T-20 for significantly longer periods of time, as required to recruit a critical number of free Envs to the site of the fusion pore. In a recent study, T-20 mediated 100% inhibition when added within the first 15 minutes of cell mixing but was essentially inactive (<10% inhibition) at 75 minutes [15]. Ongoing studies are examining the effects of PRO 542 during this time period.

Additional studies are exploring higher combinations of attachment, coreceptor and fusion inhibitors. Also, the present study employed only subtype B viruses. It will be important to determine if the combination inhibits HIV-1 in a genetic subtype-independent manner, as do PRO 542 and T-20 individually. Lastly, further studies will explore combinations of PRO 542 and T-20 against replication-competent viruses in primary cells both in vitro and in animal models of HIV-1 infection.

In summary, PRO 542 and T-20 were potently synergistic when used to inhibit HIV-1 entry in vitro. Cooperative inhibition of virus-cell and cell-cell fusion was observed for phenotypically diverse viruses and translated into meaningful dose reductions. These findings provide a strong rationale for evaluating combinations of these agents in vivo.

REFERENCES FOR THIRD SERIES OF EXPERIMENTS

1. Jacobson J M, Lowy I, Fletcher C V et al. Single-dose safety, pharmacology and antiviral activity of the human immunodeficiency virus (HIV) type 1 entry inhibitor PRO 542 in HIV-infected adults. Journal of Infectious Diseases 2000; 182:326-329.

2. Shearer W T, Israel R J, Starr S et al. Recombinant CD4-IgG2 in HIV-1 infected children: Phase I/II study. Journal of Infectious Diseases 2000; 182:1774-1779.

3. Kilby J M, Hopkins S, Venetta T M et al. Potent suppression of HIV-1 replication in humans by T-20, a peptide inhibitor of gp41-mediated virus entry. Nat Med 1998; 4:1302-1307.

4. Pilcher C D, Eron J J, Ngo L et al. Prolonged therapy with the fusion inhibitor T-20 in combination with oral antiretroviral agents in an HIV-infected individual. AIDS 1999; 13:2171-2173.

5. Allaway G P, Davis-Bruno K L, Beaudry G A et al. Expression and characterization of CD4-IgG2, a novel heterotetramer which neutralizes primary HIV-1 isolates. AIDS Research and Human Retroviruses 1995; 11:533-539.

6. Wild C T, Shugars D C, Greenwell T K, McDanal C B, Matthews T J. Peptides corresponding to a predictive alpha-helical domain of human immunodeficiency virus type 1 gp41 are potent inhibitors of virus infection. Proc Natl Acad Sci USA 1994; 91:9770-9774.

7. Chan D C, Kim P S. HIV entry and its inhibition. Cell 1998; 93:681-684.

8. Trkola A, Ketas T, KewalRamani V N et al. Neutralization sensitivity of human immunodeficiency virus type 1 primary isolates to antibodies and CD4-based reagents is independent of coreceptor usage. J Virol 1998; 72:1876-1885.

9. Dragic T, Litwin V, Allaway G P et al. HIV-1 entry into CD4+ cells is mediated by the chemokine receptor CC-CKR-5. Nature 1996; 381:667-673.

10. Litwin V, Nagashima K A, Ryder A M et al. Human immunodeficiency virus type 1 membrane fusion mediated by a laboratory-adapted strain and a primary isolate analyzed by resonance energy transfer. Journal of Virology 1996; 70:6437-6441.

11. Chou T C, Talalay P. Quantitative analysis of dose-effect relationships: the combined effects of multiple drugs or enzyme inhibitors. Advances in Enzyme Regulation 1984; 22:27-55.

12. Trkola A, Dragic T, Arthos J et al. CD4-dependent, antibody-sensitive interactions between HIV-1 and its co-receptor CCR-5. Nature 1996; 384:184-187.
13. Fu Y K et al., Physiochemical dissociation of CD4-mediated syncytium formation and shedding of human immunodeficiency virus type 1 gp120. Journal of Virology 1993, 67:3838-3825.
14. Derdeyn C A, Decker J M, Sfakianos J N et al. Sensitivity of human immunodeficiency virus type 1 to the fusion inhibitor T-20 is modulated by coreceptor specificity defined by the V3 loop of gp120. Journal of Virology 2000; 74:8358-8367.
15. Munoz-Barroso I, Durell S, Sakaguchi K, Appella E, Blumenthal R. Dilation of the human immunodeficiency virus-1 envelope glycoprotein fusion pore revealed by the inhibitory action of a synthetic peptide from gp41. J Cell Biol 1998; 140:315-323.

Fourth Series of Experiments

Mechanisms of Synergy Between HIV-1 Attachment, Coreceptor and Fusion Inhibitors HIV-1 entry proceeds via a cascade of events that provide promising targets for a new generation of antiviral therapies, including the gp120-CD4 attachment inhibitor PRO542, the gp120-coreceptor inhibitor PRO140, and the gp41 fusion inhibitors T-20 and T-1249. The multi-step nature of HIV-1 entry leaves the virus highly susceptible to inhibition by combinations of drugs that act at distinct stages of this process. It has been shown that double and triple drug cocktails of attachment, coreceptor and the fusion inhibitors potently and synergistically block HIV-1 entry over a wide range of experimental conditions in vitro.

The present study was performed in order to identify the molecular basis of the observed synergistic interactions. HIV-1 membrane fusion was monitored in real time using a semi-automatic fluorometric assay, and the inhibitory activities of the individual drugs and drug cocktails were evaluated in time-of-addition, washout, and stepwise temperature-controlled studies. The data were consistent with a model wherein the drugs act cooperatively to delay the recruitment of a critical number of fusion-active HIV-1 envelope glycoproteins to the site of the fusion pore. These findings have important implications for the combination use of HIV-1 entry inhibitors in vivo, which may emerge as an important new paradigm for antiviral therapy.

Figure 11:
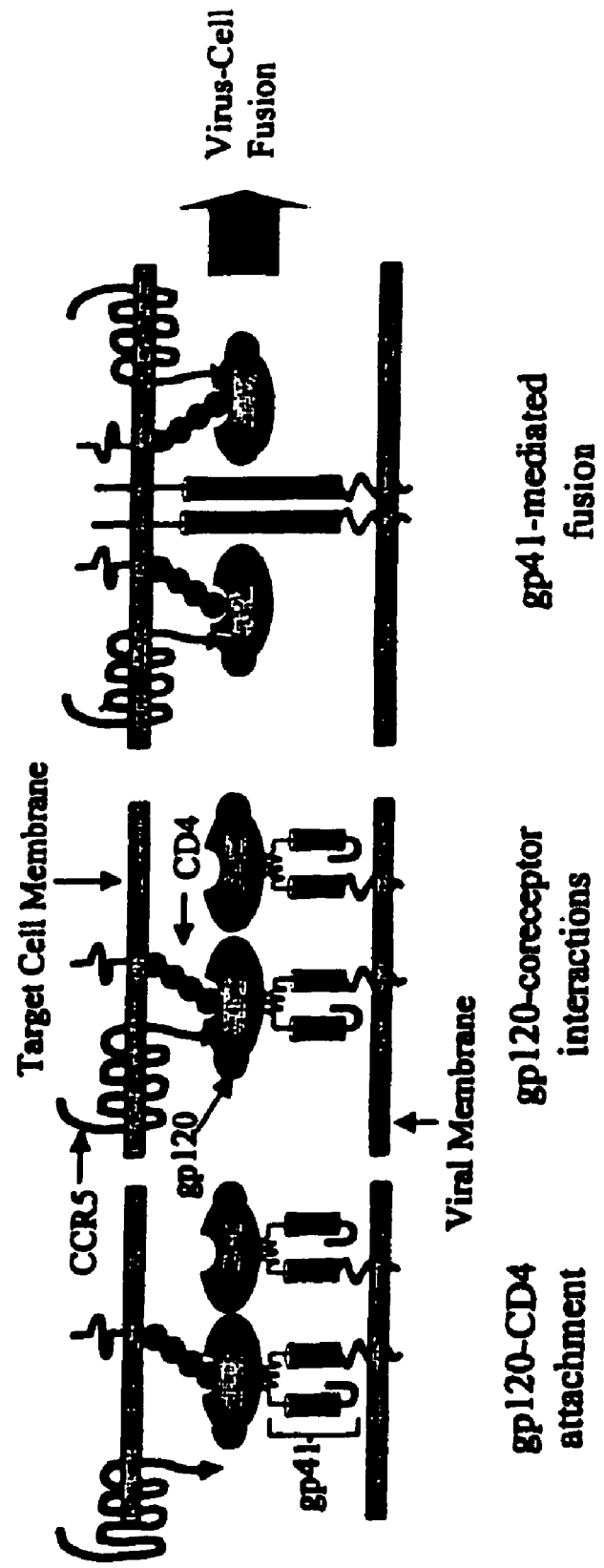

As shown in FIG. 11, HIV-1 entry involves at least three steps that provide targets for therapy: (1) gp120-CD4 attachment; (2) gp120-coreceptor interactions; and (3) gp41-mediated fusion.

Figure 12:
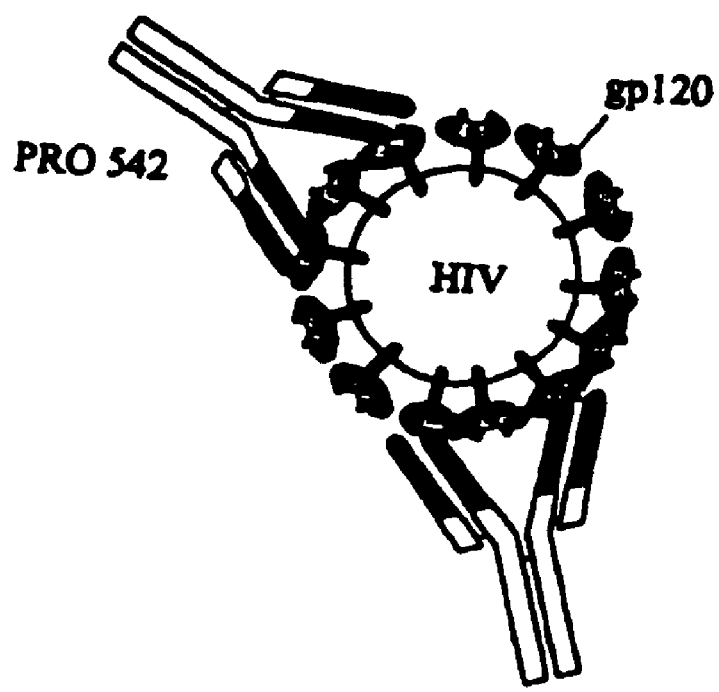

The CD4-IgG2 attachment inhibitor (PRO 542), as shown in FIG. 12. Is a tetravalent CD4-based protein. It broadly and potently neutralizes primary HIV isolates in vitro, ex vivo and in vivo, and acts prior to fusion. PRO542 has completed two phase I/II clinical trials, showing (1) excellent safety and pharmacokinetic profiles and that it is non-immunogenic; (2) statistically significant reductions in viral load with a single dose; and (3) sustained reductions in free and cell-associated infectious virus. PRO 542 is in Phase II testing.

Figure 13:
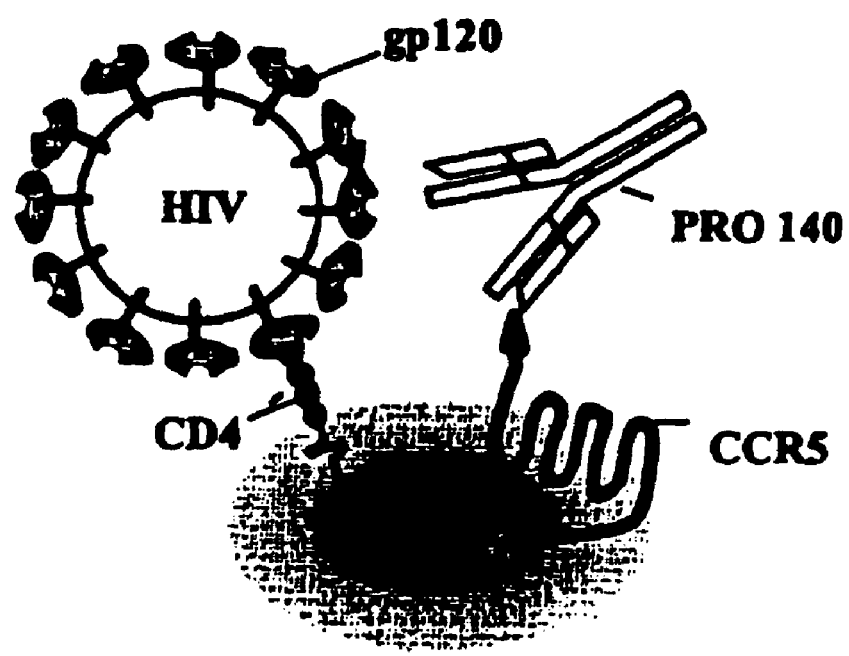
Figure 14:
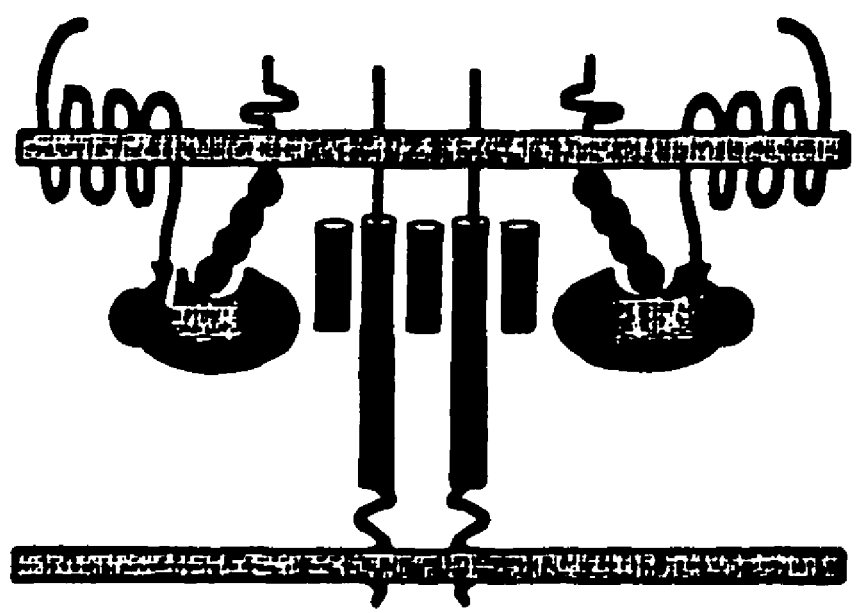

The PRO 140 coreceptor inhibitor, as shown in FIG. 13, is a monoclonal antibody to CCR5. It potently neutralizes CCR5-using virus. It protects primary T cells and macrophages, and its inhibition is genetic subtype-independent. It selectively blocks HIV entry without affecting chemokine-induced signaling. There has been no emergence of HIV resistance following 31 weeks in vitro culture.

The T-20 fusion inhibitor, as shown in 14, is a peptide derived from HIV-1 gp41. It broadly and potently blocks HIV-1 cell-cell and cell-virus fusion in vitro. It has completed Phase I/II clinical trials, showing (1) good tolerability; (2) pK supports twice daily subcutaneous dosing; and (3) clinically significant dose-dependent reductions in viral load.

Combination Use of Entry Inhibitors

Combination therapy may be required to control HIV in vivo. HIV entry inhibitors may represent the next major advance in therapy. It is critical to determine drug-drug interactions earlier rather than later in clinical development to avoid antagonistic combinations and identify synergistic combinations. The clinical benefits of synergistic combinations include more potent antiviral effects and more durable antiviral effects.

Figure 15:
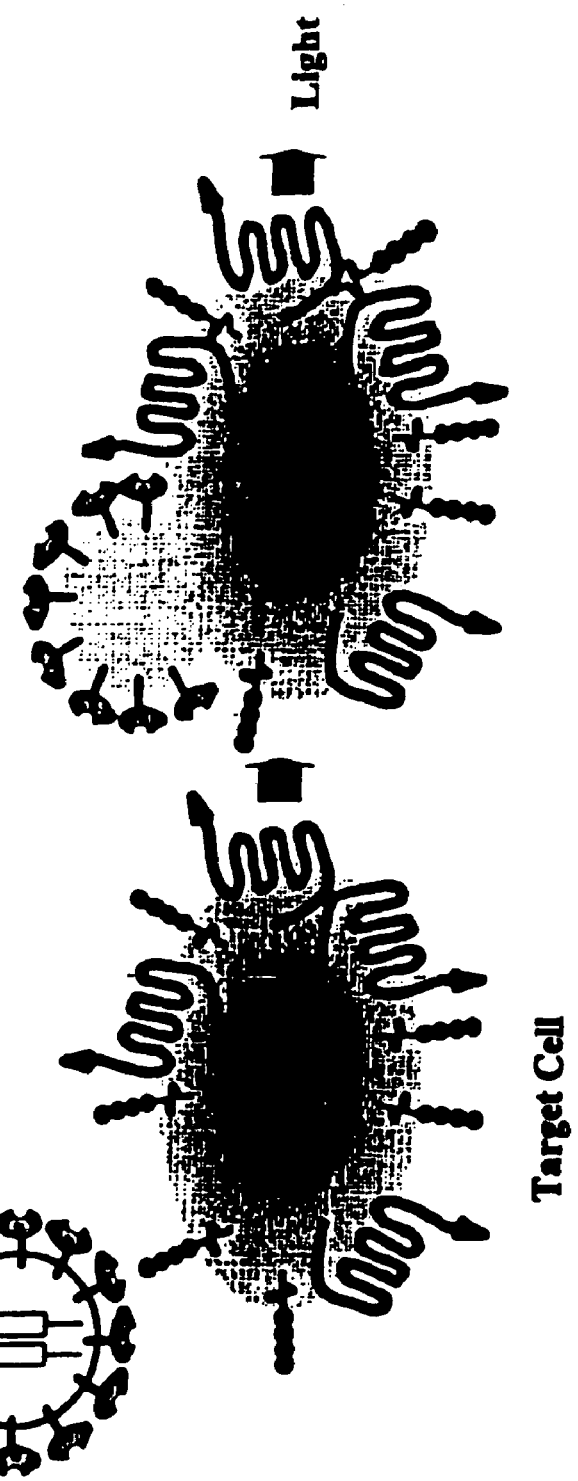

An HIV-1 virus-cell fusion assay is described in FIG. 15. In a single-cycle HIV-1 entry assay, Env-Luc+ HIV reporter viruses were prepared as described [1]. The viruses are complemented with gp120/gp41 from an HIV strain of interest and thus are capable of fusing with target cells that express CD4 and fusion coreceptors, resulting in the introduction of the viral genes into the cell. Because the viruses encode the luciferase reporter enzyme rather than HIVenv, infection leads to the production of luciferase rather than new viral particles. The amount of luciferase is measured 72 hours post-infection using standard methods.

Figure 16:
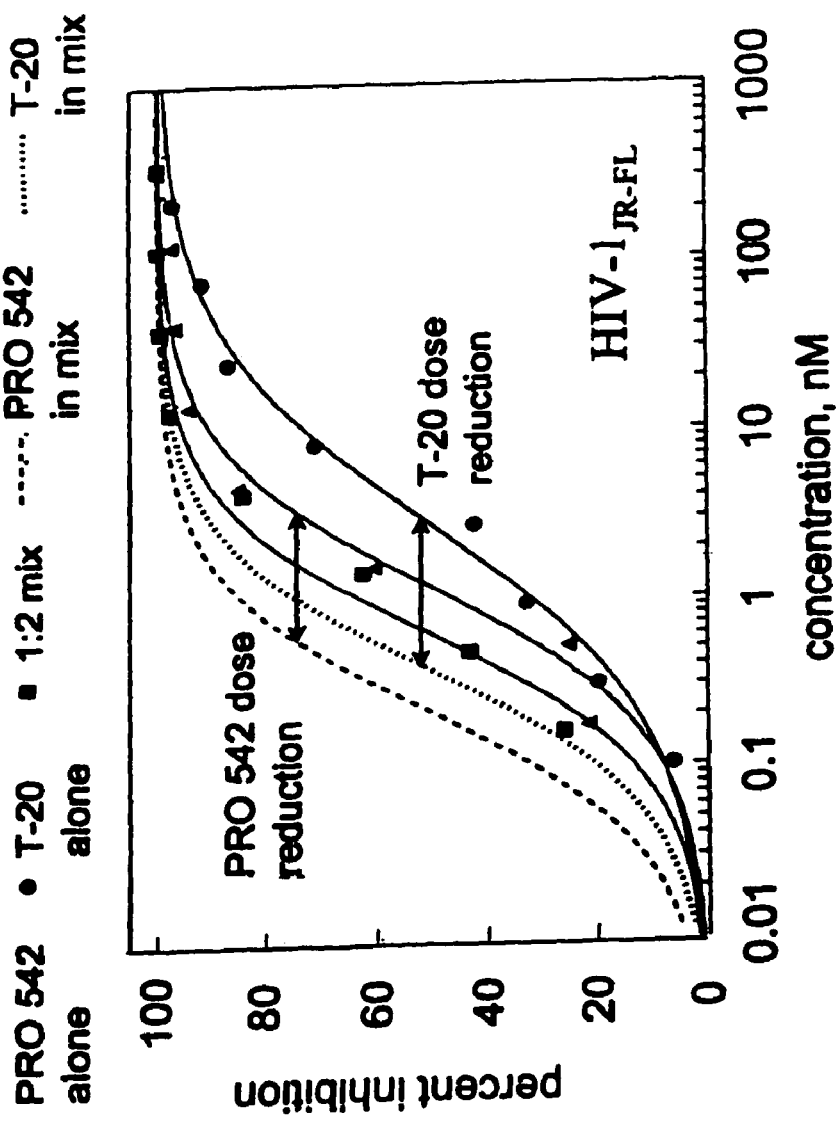

FIGS. 16 and 17 demonstrate the synergistic inhibition of virus-cell fusion with PRO542 and T-20.

Figure 18:
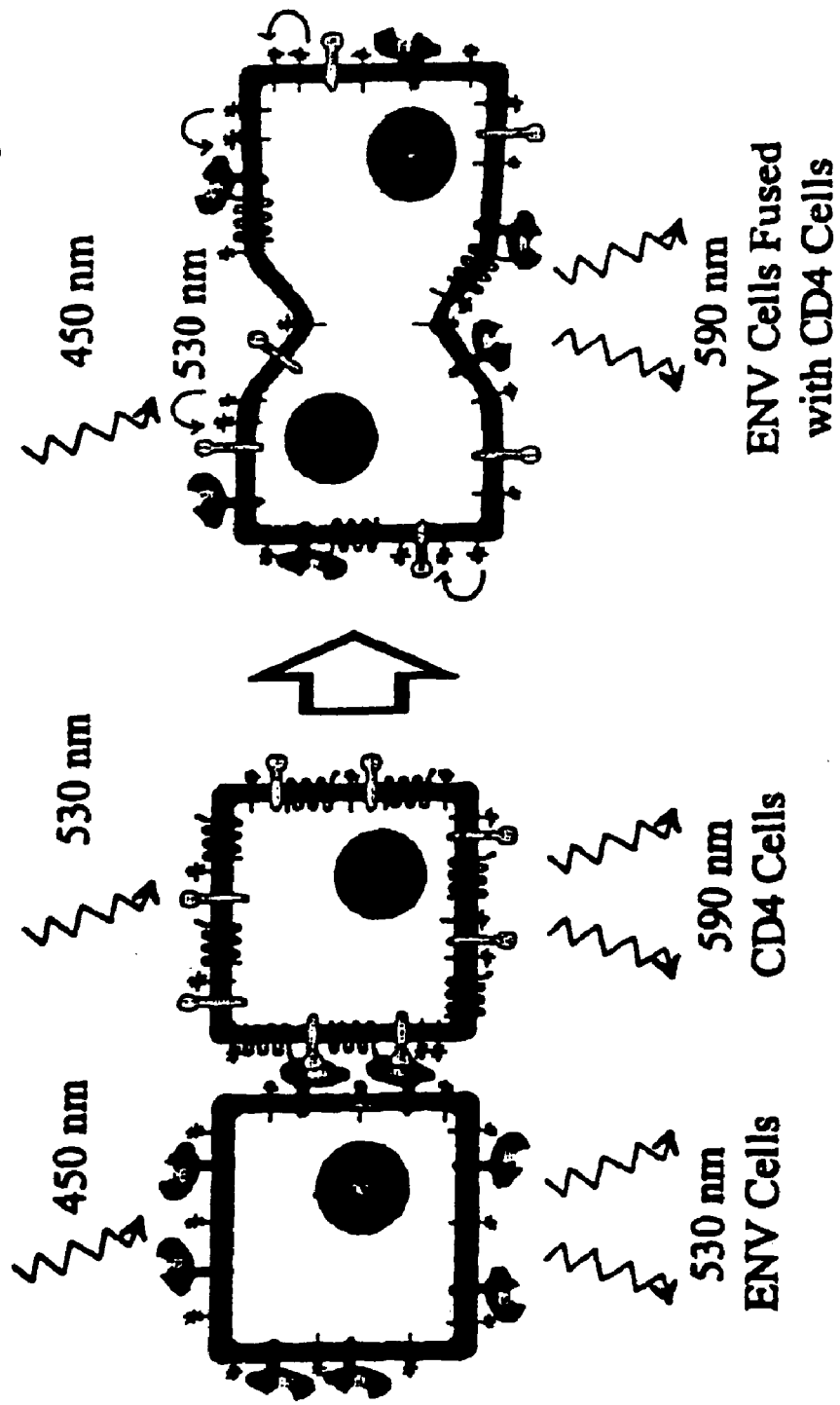

An HIV-1 cell-cell fusion assay is described in FIG. 18. Such assay is a Resonance Energy Transfer (RET) assay of HIV-1 membrane fusion. Cells expressing gp120/gp41 (ENV cells) are labeled with the fluorescent dye octadecyl fluorescsin (F18), while T cell that express CD4 and fusion coreceptors (CD4 cells) are labeled with octadecyl rhodamine (R18). The emission spectrum of F18 overlaps with the excitation spectrum of R18, allowing fluorescence RET to occur when the dyes are placed in the same membrane following fusion. RET is measured by stimulating F18 at 450 nm and measuring the R18 emission at 590 nm. The RET signal is directly related to the amount of HIV-1 fusion [2].

Figure 19:
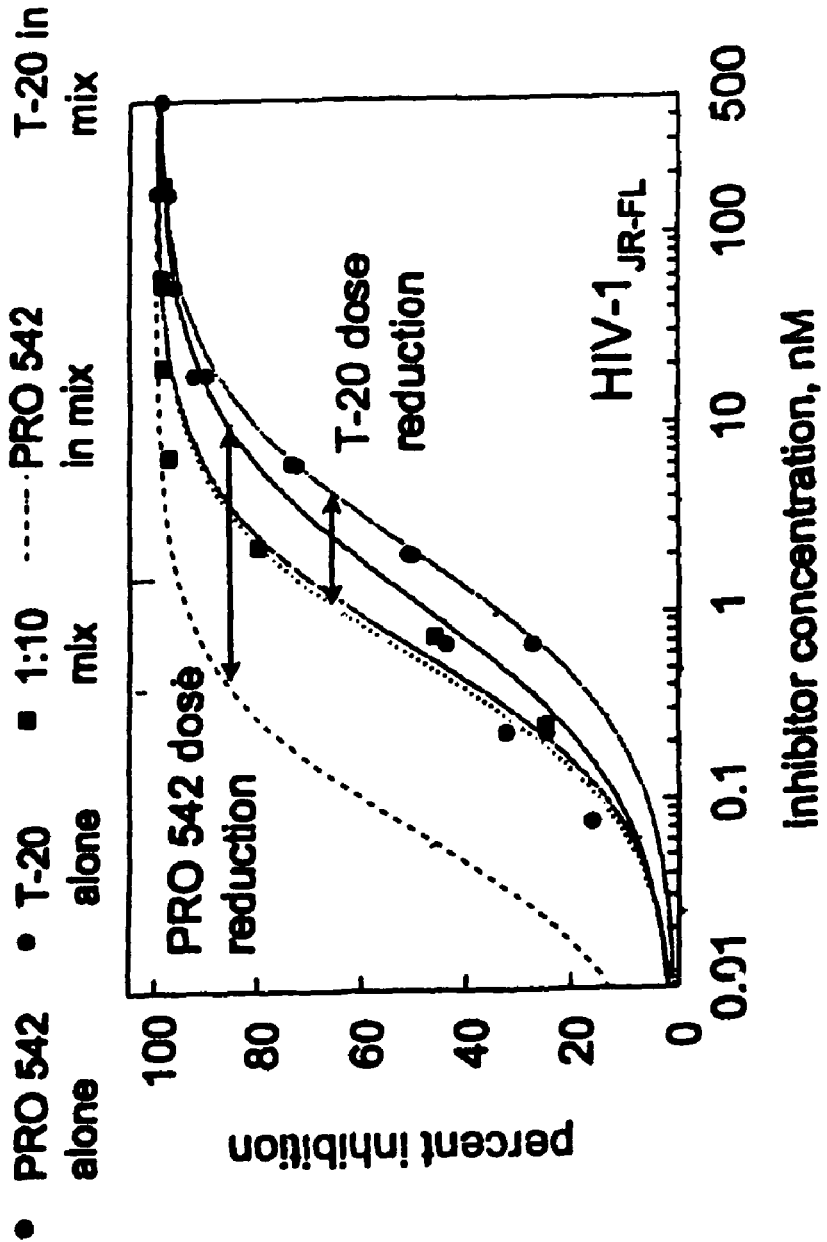

FIGS. 19 and 20 demonstrate the synergistic inhibition of cell-cell fusion with PRO542 and T-20.

Figure 21:
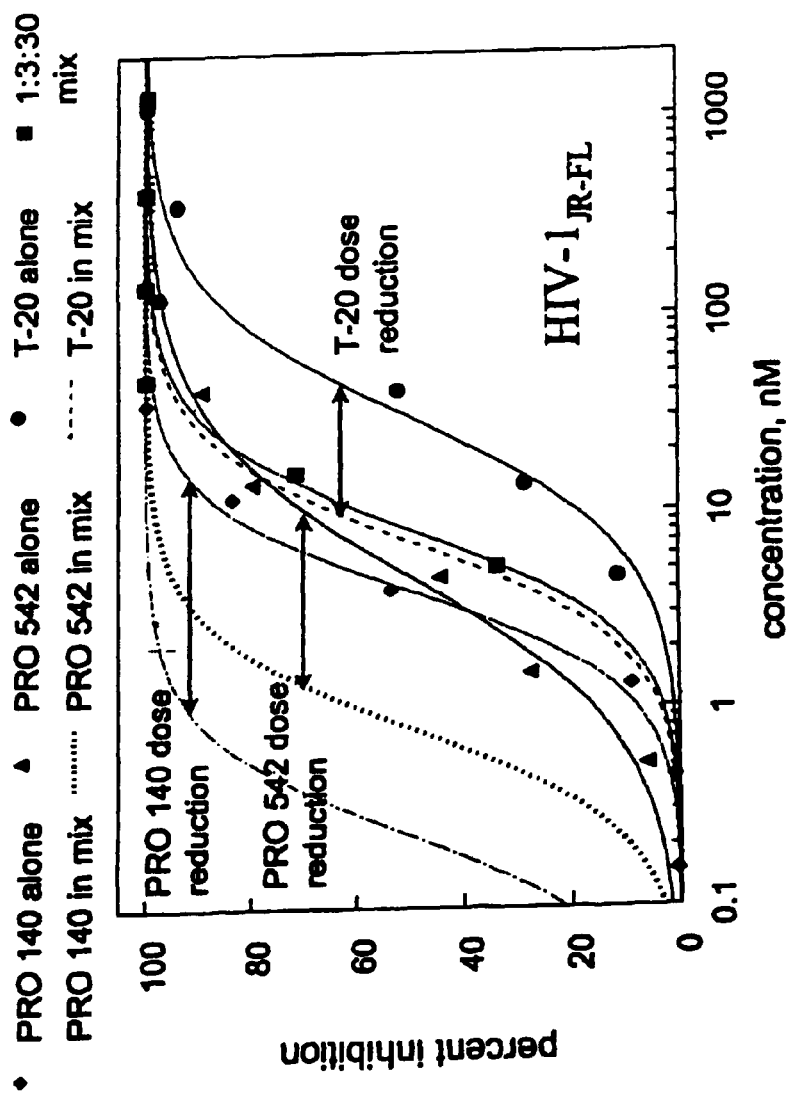

FIGS. 21 and 22 demonstrates that the PRO140, PRO542 and T-20 triple combination synergistically blocks HIV-1 entry.

Figure 23:
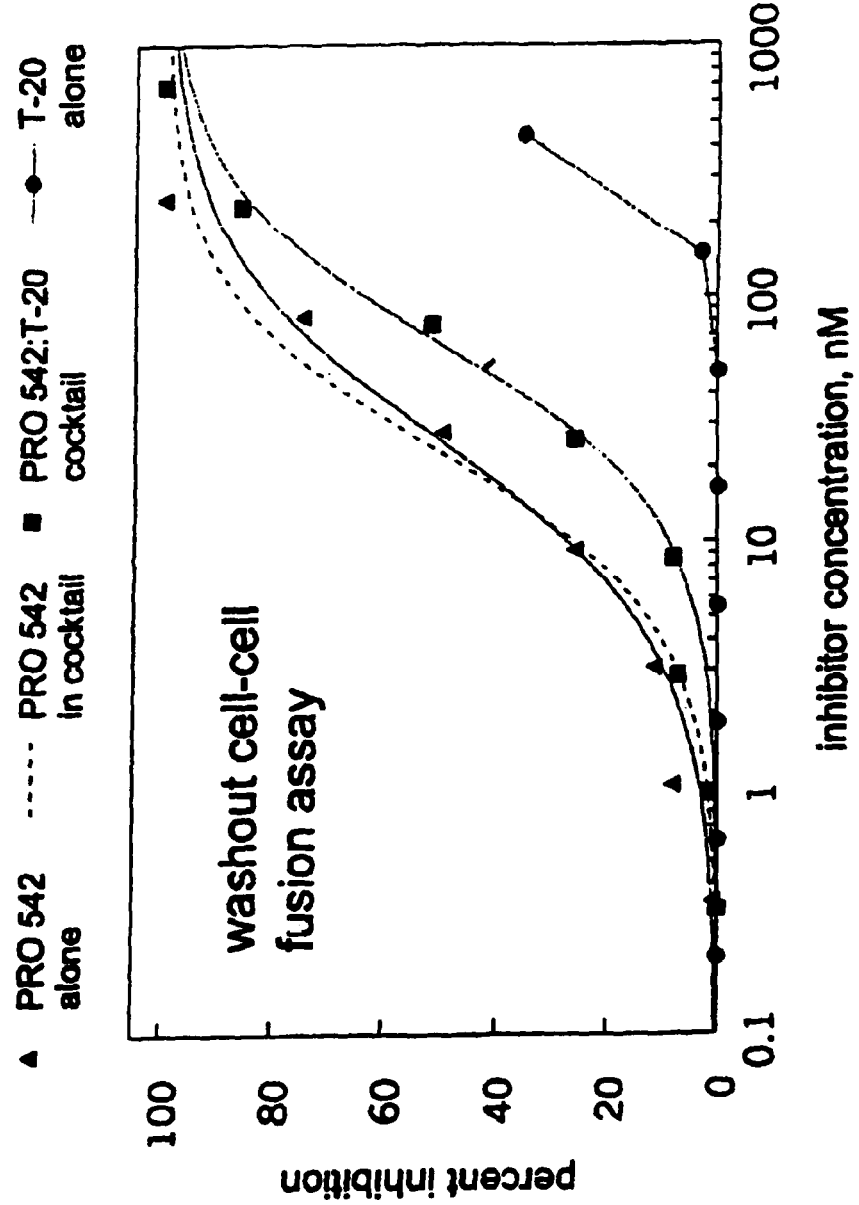

FIG. 23 demonstrates that PRO542 does not potentiate T-20 activity in the absence of coreceptor. PRO542, T-20 or a 1:2 mixture were pre-incubated with HeLa-ENVJR-FL cells for 2 hours at 37° C. prior to washing, addition of PM1 target cells, and completion of the fusion assay.

Figure 24:
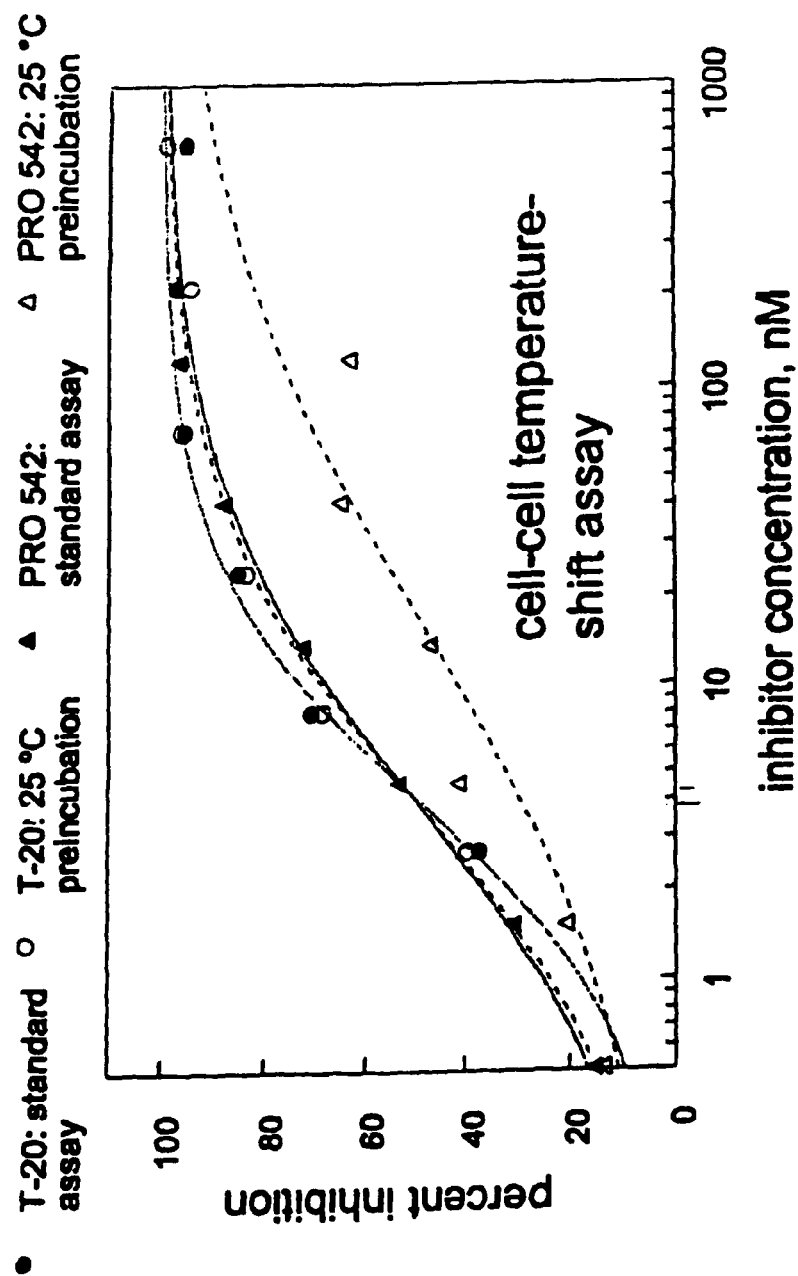
Figure 25:
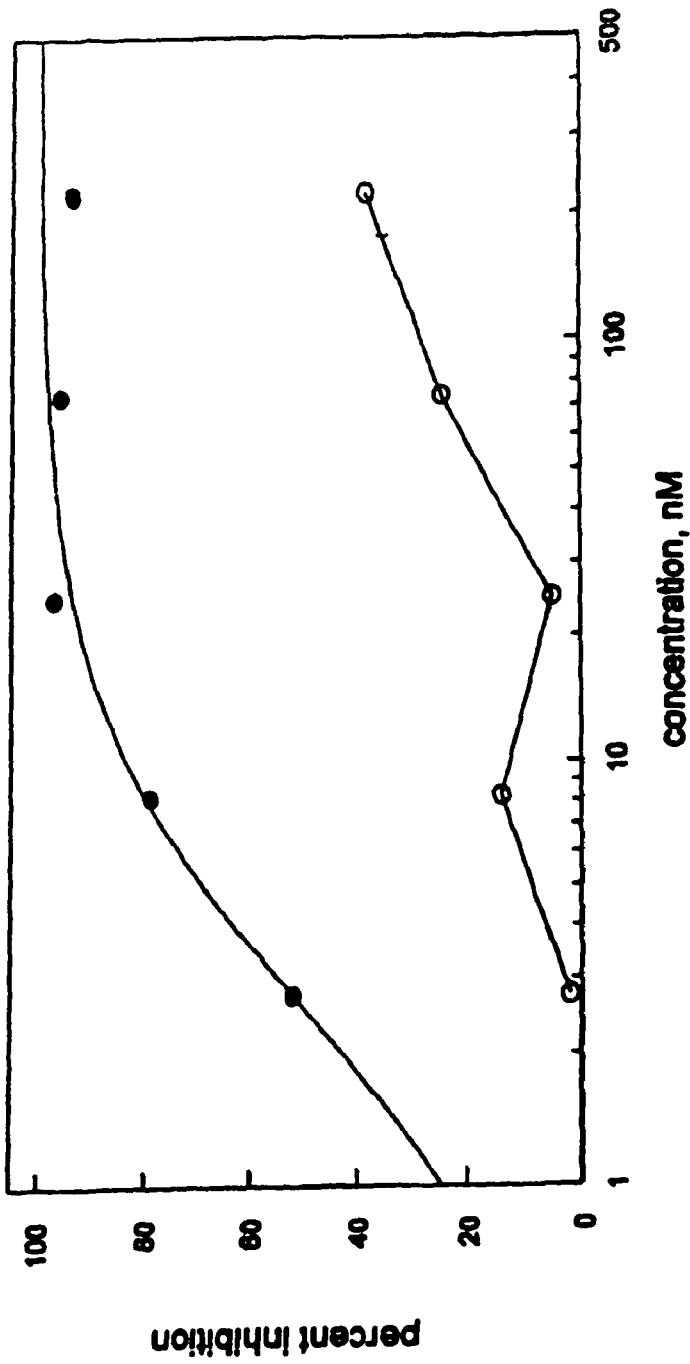

Formation of the prehairpin intermediates may need CD4, coreceptor and 37° C., as demonstrated in FIGS. 24 and 25.

Figure 26:
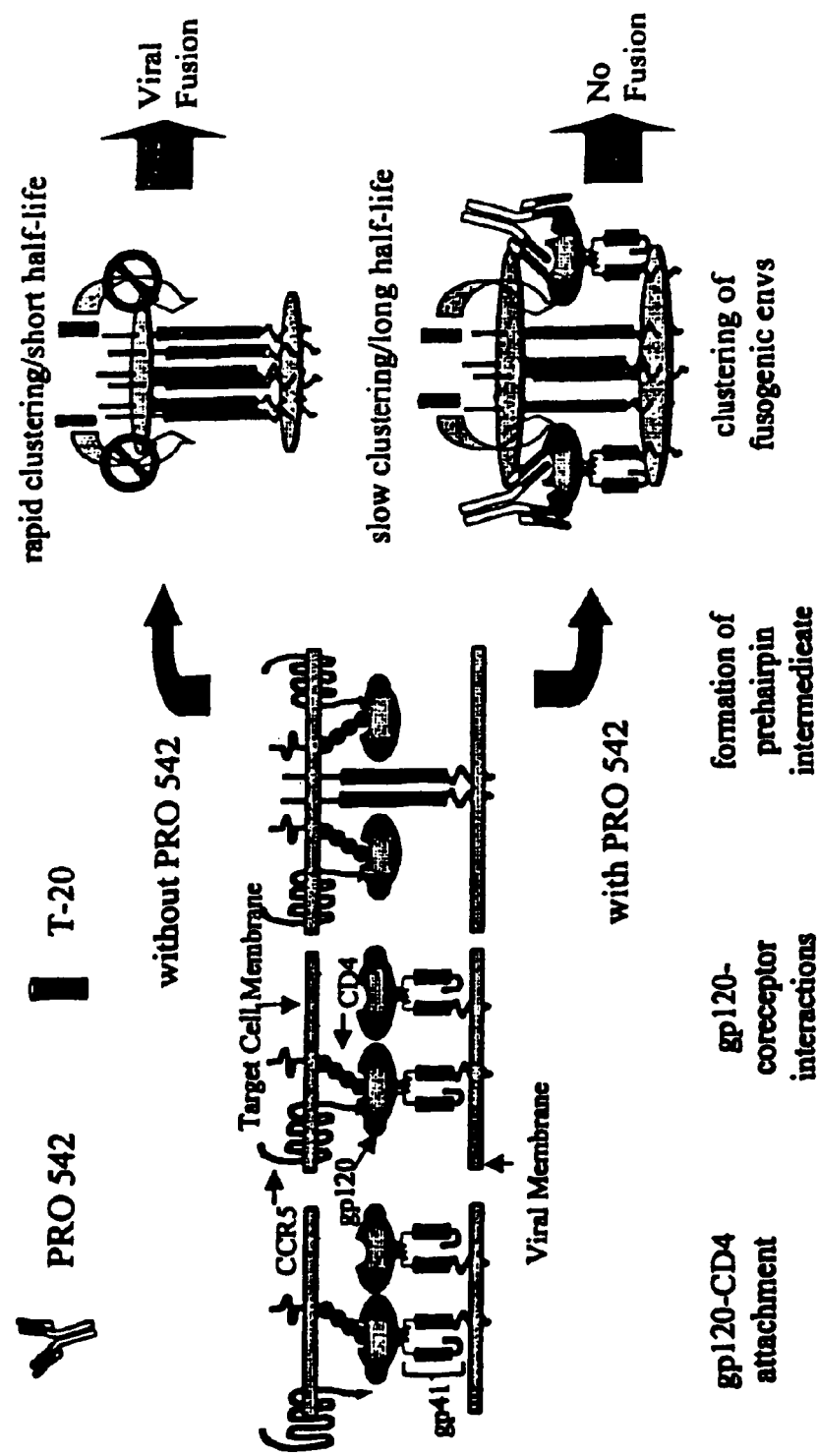
Figure 27:
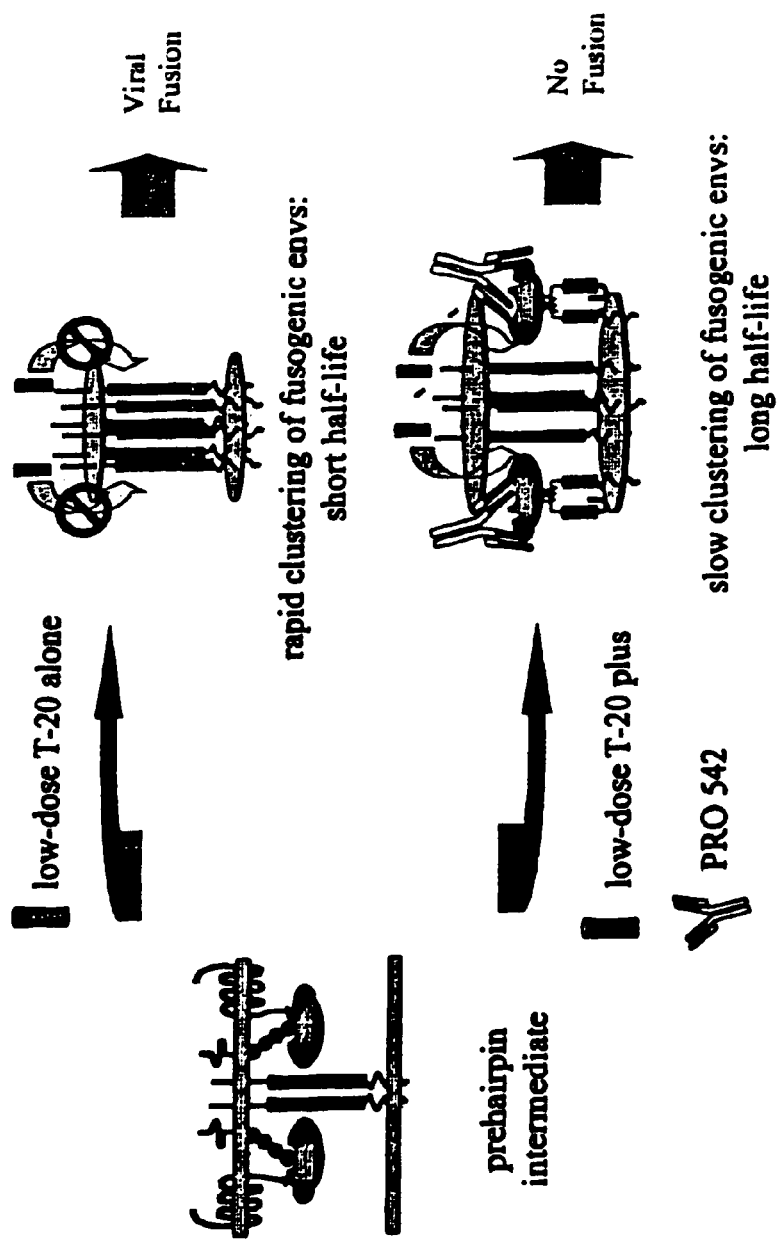

FIGS. 26 and 27 describe a possible mechanism of synergy, wherein PRO542 increases the half-life of the T-20 targets.

Figure 28:
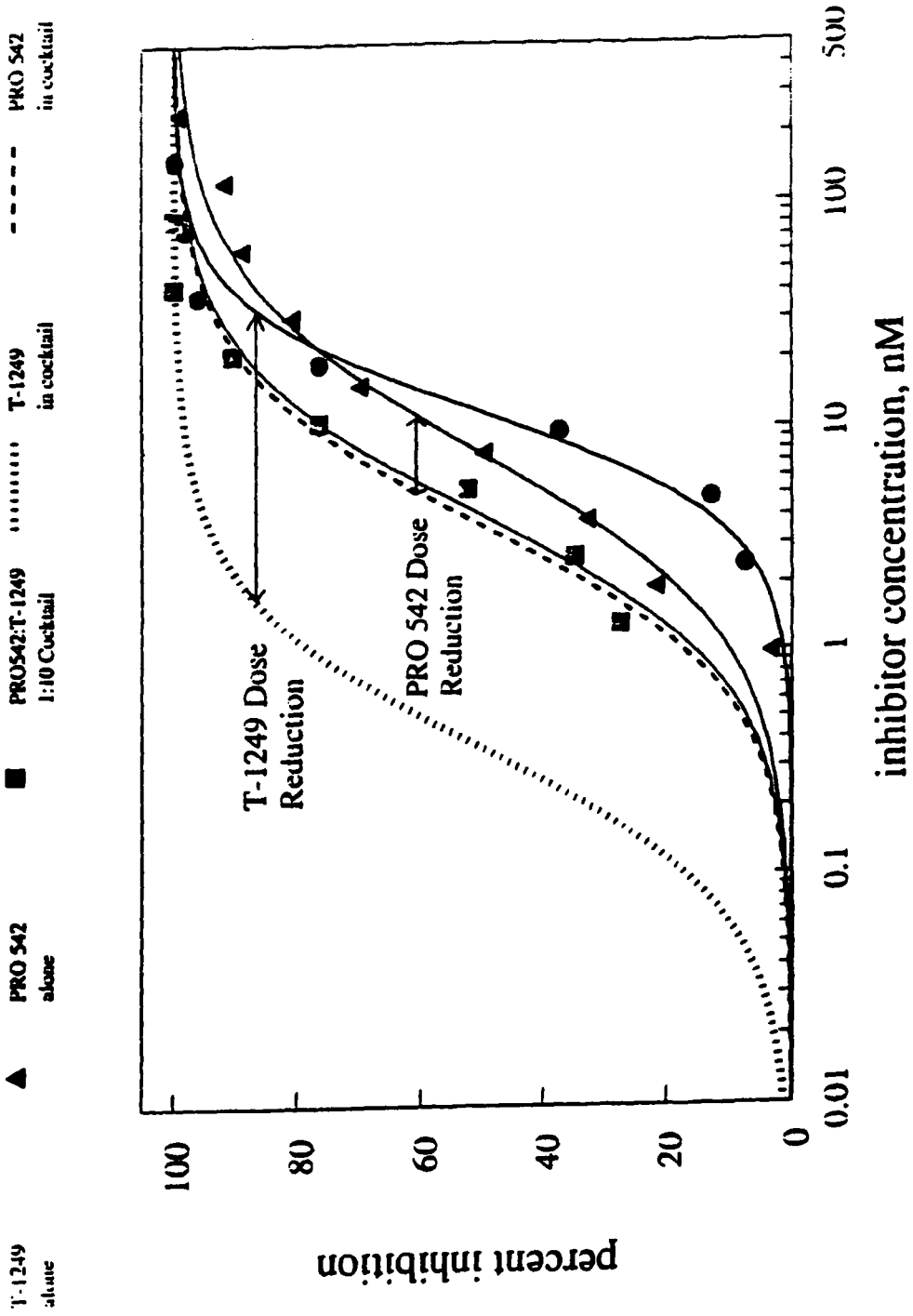

FIG. 28 demonstrates synergistic inhibition of HIV-1 entry using PRO542, T-1249 and in a 1:10 molar combination in an env-medicated membrane fusion (RET) assay. FIG. 29 demonstrates the combination indices and dose reductions for a 1:10 molar combination of PRO542 and T-1249.

REFERENCES FOR FOURTH SERIES OF EXPERIMENTS

1. Dragic et al, Nature 381:667.
2. Litwin et al., J. Virol. 70:6437.

---

What is claimed:

1. A method of inhibiting HIV-1 infection of a CD4+ cell in a subject which comprises administering to the subject a first compound which is a monoclonal antibody PA14 (produced by hybridoma PA14 having ATCC Accession No. HB-12610) or a portion thereof which binds to a CCR5 receptor, or a humanized PA14 antibody or a portion of thereof which binds to a CCR5 receptor, or a chimeric PA14 antibody or a portion thereof which binds to a CCR5 receptor; and (b) administering to the subject a second compound which is T-20 having the amino-acid sequence set forth in SEQ ID NO:1, so as to thereby inhibit HIV-1 infection of the CD4+ cell in the subject.

2. The method of claim 1, wherein the first and second compounds are administered to the subject separately.

3. The method of claim 1, wherein the first and second compounds are administered to the subject simultaneously.

4. The method of claim 1, wherein the first and second compounds are administered to the subject at different times.

5. The method of claim 4, wherein the first compound is administered to the subject following the administration of the second compound.

6. The method of claim 1, wherein the first and second compounds are administered to the subject by different routes of administration.

7. The method of claim 1, wherein the first compound is a humanized PA14 antibody or portion thereof.

8. The method of claim 1, wherein the first compound is a chimeric PA14 antibody or portion thereof.

9. The method of claim 1, wherein the relative mass ratio of the first compound to the second compound ranges from 100:1 to 1:100.

10. A method of inhibiting HIV-1 infection of a CD4+ cell in a subject which comprises (a) administering to the subject a first compound which is a monoclonal antibody PA14 (produced by hybridoma PA14 having ATCC Accession No. HB-12610) or a portion thereof which binds to a CCR5 receptor, or a humanized PA14 antibody or a portion of thereof which binds to a CCR5 receptor, or a chimeric PA14 antibody or a portion thereof which binds to a CCR5 receptor; (b)

administering to the subject a second compound which is a CD4-IgG2 chimeric heterotetramer comprising two heavy chains and two light chains, wherein the heavy chains are encoded by expression vector CD4-IgG2HC-pRcCMV having ATCC Accession No. 75193 and the light chains are encoded by expression vector CD4-kLC-pRcCMV having ATCC Accession No. 75194; and (c) administering to the subject a third compound which is T-20 having the amino-acid sequence set forth in SEQ ID NO:1, so as to thereby inhibit HIV-1 infection of the CD4+ cell.

11. The method of claim 10, wherein the first and second compounds are administered to the subject separately.

12. The method of claim 10, wherein the compounds are administered to the subject simultaneously.

13. The method of claim 10, wherein the compounds are administered to the subject at different times.

14. The method of claim 13, wherein the first compound is administered to the subject following the administration of the third compound.

15. The method of claim 13, wherein the first and second compounds are administered to the subject following the administration of the third compound.

16. The method of claim 10, wherein the compounds are administered to the subject by different routes of administration.

17. The method of claim 10, wherein the first compound is a humanized PA14 antibody or portion thereof, or is a chimeric PA14 antibody or portion thereof.

18. The method of claim 10, wherein the relative mass ratio of any two of the compounds of (a)-(c) ranges from 100:1 to 1:100.

19. A method of inhibiting HIV-1 infection of a CD4+ cell in a subject who is receiving or has recently received treatment with a compound T-20 having the amino acid sequence set forth in SEQ ID NO:1, comprising administering to the subject a second compound which is a monoclonal antibody PA14 (produced by hybridoma PA14 having ATCC Accession No. HB-12610), or a portion thereof which binds to a CCR5 receptor, or a humanized PA14 antibody or a portion of thereof which binds to a CCR5 receptor, or a chimeric PA14 antibody or a portion thereof which binds to a CCR5 receptor, in an amount effective to inhibit HIV-1 infection of the CD4+ cell in the subject.

20. The method of claim 19, wherein the second compound is a humanized PA14 antibody or a portion of thereof which binds to a CCR5 receptor, or a chimeric PA14 antibody or a portion thereof which binds to a CCR5 receptor.

21. The method of claim 1, wherein the first compound is monoclonal antibody PA14 (produced by hybridoma PA14 having ATCC Accession No. HB-12610) or a portion thereof.

22. The method of claim 10, wherein the first compound is monoclonal antibody PA14 (produced by hybridoma PA14 having ATCC Accession No. HB-12610) or a portion thereof.

23. The method of claim 19, wherein the second compound is monoclonal antibody PA14 (produced by hybridoma PA14 having ATCC Accession No. HB-12610) or a portion thereof.

* * * * *